US010799533B2

(12) United States Patent
Corash et al.

(10) Patent No.: US 10,799,533 B2
(45) Date of Patent: Oct. 13, 2020

(54) PLASMA COMPOSITIONS AND METHODS OF USE THEREOF

(71) Applicant: Cerus Corporation, Concord, CA (US)

(72) Inventors: Laurence Corash, Concord, CA (US); Richard Benjamin, Concord, CA (US); Johannes Vermeij, Concord, CA (US); Elan Weiner, Vernon Hills, IL (US)

(73) Assignee: Cerus Corporation, Concord, CA (US)

( * ) Notice: Subject to any disclaimer, the term of this patent is extended or adjusted under 35 U.S.C. 154(b) by 221 days.

(21) Appl. No.: 15/770,186

(22) PCT Filed: Oct. 21, 2016

(86) PCT No.: PCT/US2016/058318
§ 371 (c)(1),
(2) Date: Apr. 20, 2018

(87) PCT Pub. No.: WO2017/070619
PCT Pub. Date: Apr. 27, 2017

(65) Prior Publication Data

US 2018/0318348 A1 Nov. 8, 2018

Related U.S. Application Data

(60) Provisional application No. 62/354,653, filed on Jun. 24, 2016, provisional application No. 62/268,462, filed on Dec. 16, 2015, provisional application No. 62/245,926, filed on Oct. 23, 2015.

(51) Int. Cl.
*A61K 35/16* (2015.01)
*A61P 7/00* (2006.01)
*A61K 9/00* (2006.01)

(52) U.S. Cl.
CPC ............ *A61K 35/16* (2013.01); *A61K 9/0019* (2013.01); *A61P 7/00* (2018.01)

(58) Field of Classification Search
None
See application file for complete search history.

(56) References Cited

U.S. PATENT DOCUMENTS

| | | | |
|---|---|---|---|
| 5,167,656 | A | 12/1992 | Lynn |
| 5,288,605 | A | 2/1994 | Lin et al. |
| 5,399,719 | A | 3/1995 | Wollowitz et al. |
| 5,405,343 | A | 4/1995 | Mohr |
| 5,459,030 | A | 10/1995 | Lin et al. |
| 5,482,828 | A | 1/1996 | Lin et al. |
| 5,556,993 | A | 9/1996 | Wollowitz et al. |
| 5,559,250 | A | 9/1996 | Cook |
| 5,578,736 | A | 11/1996 | Wollowitz et al. |
| 5,585,503 | A | 12/1996 | Wollowitz et al. |
| 5,589,462 | A | 12/1996 | Patat et al. |
| 5,593,823 | A | 1/1997 | Wollowitz et al. |
| 5,618,662 | A | 4/1997 | Lin et al. |
| 5,625,079 | A | 4/1997 | Wollowitz et al. |
| 5,654,443 | A | 8/1997 | Wollowitz et al. |
| 5,691,132 | A | 11/1997 | Wollowitz et al. |
| 5,712,085 | A | 1/1998 | Wollowitz et al. |
| 5,871,900 | A | 2/1999 | Wollowitz et al. |
| 5,908,742 | A | 6/1999 | Lin et al. |
| 5,965,349 | A | 10/1999 | Lin |
| 5,972,593 | A | 10/1999 | Wollowitz et al. |
| 6,004,741 | A | 12/1999 | Wollowitz et al. |
| 6,004,742 | A | 12/1999 | Wollowitz et al. |
| 6,017,691 | A | 1/2000 | Wollowitz et al. |
| 6,093,725 | A | 7/2000 | Cook et al. |
| 6,099,734 | A | 8/2000 | Mclarty |
| 6,133,460 | A | 10/2000 | Wollowitz et al. |
| 6,143,490 | A | 11/2000 | Cook et al. |
| 6,171,777 | B1 | 1/2001 | Cook |
| 6,177,441 | B1 | 1/2001 | Cook et al. |
| 6,194,139 | B1 | 2/2001 | Wollowitz et al. |
| 6,218,100 | B1 | 4/2001 | Wollowitz et al. |
| 6,251,580 | B1 | 6/2001 | Lin |
| 6,270,952 | B1 | 8/2001 | Cook et al. |
| 6,281,225 | B1 | 8/2001 | Hearst et al. |
| 6,364,864 | B1 | 4/2002 | Mohiuddin |
| 6,410,219 | B1 | 6/2002 | Cook et al. |
| 6,420,570 | B1 | 7/2002 | Wollowitz |
| 6,433,343 | B1 | 8/2002 | Cimino et al. |
| 6,455,286 | B1 | 9/2002 | Wollowitz |
| 6,469,052 | B2 | 10/2002 | Wollowitz |
| 6,503,699 | B1 | 1/2003 | Wollowitz et al. |
| 6,514,987 | B1 | 2/2003 | Cook et al. |
| 6,544,727 | B1 | 4/2003 | Hei |
| 6,548,242 | B2 | 4/2003 | Horowitz et al. |

(Continued)

FOREIGN PATENT DOCUMENTS

| | | | |
|---|---|---|---|
| GB | 1516698 | A | 7/1978 |
| WO | WO-1993/00005 | A1 | 1/1993 |

(Continued)

OTHER PUBLICATIONS

Anonymous. (Nov. 17, 2005). "Guideline on the Core SPC for Human Albumin Solution (CPMP/PhVWP/BPWG/2231/99 rev. 2)," Committee for Medicinal Products for Human Use (CHMP) pp. 1-10.
Asselta, R. et al. (2006). "The Molecular Basis of Quantitative Fibrinogen Disorders," Journal of Thrombosis and Haemostasis 4:2115-2129.
Aznar, J.A. et al. (Jan. 1, 2000). "Influence of Methylene Blue Photoinactivation Treatment on Coagulation Factors from Fresh Frozen Plasma, Cryoprecipitates and Cryosupernatants," Vox Sanguinis 78:156-160.
Burnouf, T. et al. (Feb. 2011). "Pathogen Reduction Technique for Fresh-Frozen Plasma Fraction Minipools Prepared in Disposable Processing Bag Systems," Transfusion 51:446-447.
Circular of Information for the Use of Human Blood and Blood Components (Apr. 2013)., AABB, American Cross, American's Red Blood Centers, and Armed Services Blood Program, 42 pages.

(Continued)

*Primary Examiner* — Qiuwen Mi
(74) *Attorney, Agent, or Firm* — Morrison & Foerster LLP

(57) ABSTRACT

Provided herein are pathogen-inactivated plasma compositions and methods for treating a disease or condition using pathogen-inactivated plasma compositions.

16 Claims, 11 Drawing Sheets

(56) References Cited

U.S. PATENT DOCUMENTS

| | | | |
|---|---|---|---|
| 6,565,802 | B1 | 5/2003 | Hanley |
| 6,586,749 | B2 | 7/2003 | Cimino |
| 6,686,480 | B2 | 2/2004 | Wollowitz |
| 6,709,810 | B2 | 3/2004 | Cook |
| 6,936,413 | B1 | 8/2005 | Bischof |
| 6,949,753 | B2 | 9/2005 | Cimino |
| 6,951,713 | B2 | 10/2005 | Hei et al. |
| 7,025,877 | B1 | 4/2006 | Gheldere et al. |
| 7,037,642 | B2 | 5/2006 | Hei |
| 7,068,361 | B2 | 6/2006 | Cimino |
| 7,105,093 | B2 | 9/2006 | De Gheldere |
| 7,264,608 | B2 | 9/2007 | Bischof |
| 7,293,985 | B2 | 11/2007 | Cook |
| 7,425,304 | B2 | 9/2008 | De Gheldere |
| 7,445,756 | B2 | 11/2008 | Moore |
| 7,534,348 | B2 | 5/2009 | Reitz |
| 7,611,831 | B2 | 11/2009 | Hei |
| 7,655,392 | B2 | 2/2010 | Stassinopoulos |
| 8,296,071 | B2 | 10/2012 | Edrich et al. |
| 8,439,889 | B2 | 5/2013 | Sano |
| 8,900,805 | B2 | 12/2014 | Mufti et al. |
| 9,259,525 | B2 | 2/2016 | Hei |
| 9,713,627 | B2 | 7/2017 | Mufti |
| 10,357,516 | B2 | 7/2019 | Mufti |
| 2001/0009756 | A1 | 7/2001 | Hei |
| 2001/0018179 | A1 | 8/2001 | Hei |
| 2002/0006393 | A1 | 1/2002 | Wollowitz |
| 2002/0028432 | A1 | 3/2002 | Cook |
| 2002/0042043 | A1 | 4/2002 | Stassinopoulos |
| 2002/0115585 | A1 | 8/2002 | Hei |
| 2002/0192632 | A1 | 12/2002 | Hei et al. |
| 2003/0062483 | A1 | 4/2003 | Cimino |
| 2003/0105339 | A1 | 6/2003 | Wollowitz |
| 2003/0113704 | A1 | 6/2003 | Stassinopoulos |
| 2003/0207247 | A1 | 11/2003 | Stassinopoulos |
| 2004/0029897 | A1 | 2/2004 | Cook |
| 2004/0180321 | A1 | 9/2004 | Cook |
| 2004/0185544 | A9 | 9/2004 | Hei |
| 2004/0185553 | A9 | 9/2004 | Hei |
| 2004/0197343 | A1 | 10/2004 | Dubensky et al. |
| 2004/0228877 | A1 | 11/2004 | Dubensky et al. |
| 2005/0142542 | A1 | 6/2005 | Hei |
| 2005/0175625 | A1 | 8/2005 | Jaffee et al. |
| 2005/0202395 | A1 | 9/2005 | Edrich et al. |
| 2005/0249748 | A1 | 11/2005 | Dubensky et al. |
| 2005/0281783 | A1 | 12/2005 | Kinch et al. |
| 2006/0009399 | A1 | 1/2006 | Davis |
| 2006/0115466 | A1 | 6/2006 | Stassinopoulos |
| 2007/0031457 | A1 | 2/2007 | Dubensky et al. |
| 2007/0190029 | A1 | 8/2007 | Pardoll et al. |
| 2007/0190063 | A1 | 8/2007 | Bahjat et al. |
| 2007/0207170 | A1 | 9/2007 | Dubensky et al. |
| 2007/0207171 | A1 | 9/2007 | Dubensky et al. |
| 2010/0133160 | A1 | 6/2010 | Hei |
| 2011/0033554 | A1* | 2/2011 | Burnouf ................ A61L 2/0017 424/529 |
| 2011/0286987 | A1 | 11/2011 | Mufti |
| 2013/0143198 | A1 | 6/2013 | Sailliol |
| 2015/0157665 | A1 | 6/2015 | Mufti |
| 2016/0354533 | A1 | 12/2016 | Hei |
| 2017/0027986 | A1 | 2/2017 | Corash et al. |
| 2017/0202882 | A1 | 7/2017 | Vermeij |
| 2017/0304363 | A1 | 10/2017 | Corash |
| 2018/0008639 | A1 | 1/2018 | Mufti |
| 2018/0185484 | A1 | 7/2018 | Greenman et al. |
| 2018/0289873 | A1 | 10/2018 | David |
| 2019/0085289 | A1 | 3/2019 | Greenman |
| 2019/0209718 | A1 | 7/2019 | Church |

FOREIGN PATENT DOCUMENTS

| | | | |
|---|---|---|---|
| WO | WO-1993/17553 | A1 | 9/1993 |
| WO | WO-1994/03054 | A1 | 2/1994 |
| WO | WO-1994/27433 | A1 | 12/1994 |
| WO | WO-1995/00141 | A1 | 1/1995 |
| WO | WO-1995/12973 | A1 | 5/1995 |
| WO | WO-1995/19705 | A1 | 7/1995 |
| WO | WO-1996/08965 | A1 | 3/1996 |
| WO | WO-1996/14737 | A1 | 5/1996 |
| WO | WO-1996/14739 | A1 | 5/1996 |
| WO | WO-1996/14740 | A1 | 5/1996 |
| WO | WO-1996/39815 | A1 | 12/1996 |
| WO | WO-1996/39820 | A1 | 12/1996 |
| WO | WO-1996/40857 | A1 | 12/1996 |
| WO | WO199639818 | A1 | 12/1996 |
| WO | WO-1997/21346 | A1 | 6/1997 |
| WO | WO-1998/18908 | A1 | 5/1998 |
| WO | WO-1998/30327 | A1 | 7/1998 |
| WO | WO199830545 | A1 | 7/1998 |
| WO | WO-1999/03976 | A2 | 1/1999 |
| WO | WO-1999/03976 | A3 | 1/1999 |
| WO | WO-1999/26476 | A1 | 6/1999 |
| WO | WO-1999/34839 | A1 | 7/1999 |
| WO | WO-1999/34914 | A1 | 7/1999 |
| WO | WO-1999/34915 | A1 | 7/1999 |
| WO | WO199934839 | A1 | 7/1999 |
| WO | WO-1999/63981 | A2 | 12/1999 |
| WO | WO-1999/63981 | A3 | 12/1999 |
| WO | WO-2001/91775 | A2 | 12/2001 |
| WO | WO-2001/91775 | A3 | 12/2001 |
| WO | WO-2003/047650 | A2 | 6/2003 |
| WO | WO-2003/047650 | A3 | 6/2003 |
| WO | WO-2003/049784 | A2 | 6/2003 |
| WO | WO-2003/049784 | A3 | 6/2003 |
| WO | WO-2003/061379 | A2 | 7/2003 |
| WO | WO-2003/061379 | A3 | 7/2003 |
| WO | WO-2003/065787 | A2 | 8/2003 |
| WO | WO-2003/065787 | A3 | 8/2003 |
| WO | WO-2003/078023 | A1 | 9/2003 |
| WO | WO-2003/090794 | A1 | 11/2003 |
| WO | WO-2004/049914 | A2 | 6/2004 |
| WO | WO-2004/049914 | A3 | 6/2004 |
| WO | WO-2004/050029 | A2 | 6/2004 |
| WO | WO-2004/050029 | A3 | 6/2004 |
| WO | WO-2004/050848 | A2 | 6/2004 |
| WO | WO-2004/050848 | A3 | 6/2004 |
| WO | WO-2004/050897 | A2 | 6/2004 |
| WO | WO-2004/050897 | A3 | 6/2004 |
| WO | WO2004084936 | A2 | 10/2004 |
| WO | WO2004110481 | A2 | 12/2004 |
| WO | WO2005009463 | A2 | 2/2005 |
| WO | WO2004110481 | A3 | 3/2005 |
| WO | WO2005037233 | A2 | 4/2005 |
| WO | WO2005037233 | A3 | 4/2005 |
| WO | WO2004084936 | A3 | 6/2005 |
| WO | WO2005009463 | A3 | 6/2005 |
| WO | WO-2005/067460 | A2 | 7/2005 |
| WO | WO-2005/067460 | A3 | 7/2005 |
| WO | WO2005071088 | A2 | 8/2005 |
| WO | WO2005071088 | A3 | 8/2005 |
| WO | WO2005092372 | A2 | 10/2005 |
| WO | WO2005092372 | A3 | 10/2005 |
| WO | WO-2006/050328 | A1 | 5/2006 |
| WO | WO2007022511 | A2 | 2/2007 |
| WO | WO2007022511 | A3 | 2/2007 |
| WO | WO2007022520 | A2 | 2/2007 |
| WO | WO2007022520 | A3 | 2/2007 |
| WO | WO-2007/103261 | A2 | 9/2007 |
| WO | WO-2007/103261 | A3 | 9/2007 |
| WO | WO2007103225 | A2 | 9/2007 |
| WO | WO2007103225 | A3 | 9/2007 |
| WO | WO2007117371 | A2 | 10/2007 |
| WO | WO2007117371 | A3 | 10/2007 |
| WO | WO2009118331 | A1 | 10/2009 |
| WO | WO2009126786 | A2 | 10/2009 |
| WO | WO2009126786 | A3 | 7/2010 |
| WO | WO-2012/018484 | A2 | 2/2012 |
| WO | WO-2012/018484 | A3 | 2/2012 |
| WO | WO-2012/071135 | A2 | 5/2012 |
| WO | WO-2012/071135 | A3 | 5/2012 |
| WO | WO2016014854 | A1 | 1/2016 |
| WO | WO-2016/057965 | A1 | 4/2016 |
| WO | WO2016115535 | A1 | 7/2016 |

(56) References Cited

FOREIGN PATENT DOCUMENTS

| | | | |
|---|---|---|---|
| WO | WO-2016/210374 | A1 | 12/2016 |
| WO | WO-2017/120545 | A2 | 7/2017 |
| WO | WO-2017/120545 | A3 | 7/2017 |
| WO | WO2018119462 | A1 | 6/2018 |
| WO | WO2018125994 | A1 | 7/2018 |
| WO | WO2018161020 | A1 | 9/2018 |

OTHER PUBLICATIONS

Committee for Medicinal Products for Human Use(CHMP) (Nov. 17, 2005). "Guideline on the Core SPC for 7-12 Human Albumin Solution (CPMP/PhVWP/BPWG/2231/99 rev.2),", 10 pages.

Electronic Code of Federal Regulations (2019). Title 21: Food and Drugs, Section 606.122: Circular of Information, retrieved from https://www.ecfr.gov/cgi-bin/text-idx?SID=36cf34a3930282fa3928d7c7d8de61b0&mc=tr . . . last visited Jan. 29, 2019, 2 pages.

Extended European Search Report, dated Oct. 30, 2019, for European Patent Application No. 16858399.5, 19 pages.

Irsch, J. et al. (2011, e-pub. Jan. 27, 2001). "Pathogen Inactivation of Platelet and Plasma Blood Components for Transfusion Using the Intercept Blood System™," Transfus. Med. Hemother. 38:19-31.

McQuilten, Z.K. et al. (2017, e-pub. Jun. 27, 2017). "Fibrinogen Concentration and Use of Fibrinogen Supplementation With Cryoprecipitate in Patents With Critical Bleeding Receiving Massive Transfusion: A Bi-National Cohort Study," British Journal of Haematology 179:131-141.

O'Shaughnessy, D.F. et al. (May 12, 2004). "Guidelines for the Use of Fresh-Frozen Plasma, Cryoprecipitate and Cryosupernatant," British Journal of Haematology 126:11-28.

Press Release (Oct. 31, 2018). "Cerus Received FDA Breakthrough Device Designation for Pathogen-Reduced Cryoprecipitate," retrieved from https://www.marketwatch.com/press-release/cerus-receives-fda-breakthrough-device-design . . . , last visited Feb. 8, 2019, 4 pages.

Schlenke, P. et al. (2008). "Photochemical Treatment of Plasma With Amotosalen and UVA Light: Process Validation in Three European Blood Centers," Transfusion 48:697-705, 9 pages.

UTMB Health Blood Transfusion Services. "Plasma," retrieved from internet URL: http://www.utmb.edu/bloodbank/blood-bank-transfusion-services/component-therapy/plasma, last visited Mar. 15, 2019, 1 page.

Wiltshire, M. et al. (2013). "Quality of Cryoprecipitate Manufactured From Fresh Frozen Plasma Treated With Methylene Blue or Intercept Pathogen Inactivation Systems," Vox Sanguinis 105(Suppl. 1):157, Abstract P-264, 1 page.

Yarranton, H. et al. (Sep. 2005). "Coagulation Factor Levels in Cryosupernatant Prepared From Plasma Treated With Amotosalen Hydrochloride (S-59) and Ultraviolet A Light," Transfusion 45:1453-1458.

Yazer, M.H. (2018). "Congress Review: Auditing as a Means of Detecting Waste," ISBT Science Series 13:29-34.

U.S. Appl. No. 09/238,355, Greenman, W. et al, filed Jan. 27, 1999. (Copy not submitted herewith pursuant to the waiver of 37 C.F.R. § 1.98(a)(2)(iii) issued by the Office on Sep. 21, 2004.)

Backholer, L. et al. (2016). "Paired Comparison of Methylene Blue-and Amotosalen-Treated Plasma and Cryoprecipitate," *Vox Sanguinis* 10 pages.

Bryant, B. et al. (May 1, 2007). "Pathogen Inactivation: The Definitive Safegaurd for the Blood Supply," pp. 719-733. Retrieved from the internet <URL:http://www.archivesofpathology.org/doi/pdf/10.1043/1543-2165(2007)131[719:PITDSF]2.0.CO> lasted visited Sep. 9, 2016. pp. 724-728.

Burnouf, T. et al. (Nov. 1, 2007). "Preparation and Viral Inactivation of Cryoprecipitate in Blood Banks in Resource-Limited Countries," *ISBT Science Series,* 2(2):121-128.

Cid, J. et al. (Mar. 2013). "Quantitative and Qualitative Analysis of Coagulation Factors in Cryoprecipitate Prepared from Fresh-Frozen Plasma Inactivated with Amotosalen and Ultraviolet A Light," *Blood Components,* 53(3):600-605.

Dyck, P.J.et al. (Dec. 1994). "A Plasma Exchange Versus Immune Globulin Infusion Trial in Chronic Inflammatory Demyelinating Polyradiculoneuropathy," *Ann. Neurol.* 36(6):838-845.

El-Ekiaby, M. (2010). "Solvent-Detergent Filtered (S/D-F) Fresh Frozen Plasma and Cryoprecipitate Minipools Prepared in a Newly Designed Integral Disposable Processing Bag System," *Transfusion Medicine* 20:48-61.

Ettinger, A. et al. (2012). "Preparation of Cryoprecipitate From Riboflavin and UV Light-Treated Plasma," *Transfusion and Apheresis Science* 46:153-158.

Garwood, M. et al. (Sep. 2003). "The Effect of Methylene Blue Photoinactivation and Methylene Blue Removal on the Quality of Fresh-Frozen Plasma," *Transfusion* 43(9):1238-1247.

Green, I. et al. (Jun. 2016). "The Hemostatic Properties of Thawed Pooled Cryoprecipitate Up to 72 Hours," *Blood Components* 56:1356-1361.

Greenhalgh, D.G. (Jul./Aug. 2007). "Burn Resuscitation," *Journal of Burn Care & Research* 28(4):555-565.

Guidance for Industry: An Acceptable Circular of Information for the Use of Human Blood and Blood Components *U.S. Department of Health and Human Services,* (Aug. 2013), 83 pages.

Hayek, S. et al. (Mar. 2011). "Burn Resuscitation: Is it Straightforward or a Challenge?," *Annals of Burns and Fire Disasters* XXIV(1):17-21.

Herbrecht, R. et al. (2013). "Comparative Effectiveness and Safety of Pathogen Inactivated (Amotosalen-UVA) and Conventional Plasma for Treatment of Auto-Immmune Thrombotic Thrombocytopenic Purpura (TTP): A 15-Year Retrospective Review" *Blood* 122(21):4820, six pages.

Hornsey, V.S. et al. (Oct. 2009). "Pathogen Reduction of Fresh Plasma Using Riboflavin and Ultraviolet Light: Effects on Plasma Coagulation Proteins," *Transfusion* 49(10):2167-2172.

Inaba, K. (May 2011). "Freeze-Dried Plasma," *J. Trauma* 70(5):557-558.

Intercept Blood System, "Platelet and Plasma Synergy: A Single System for Two Components," Cerus Corporation (2006), 3 pages.

Irsch, J. et al. (2015). "Update on Pathogen Inactivation Treatment of Plasma, With the Intercept Blood System: Current Position on Methodological, Clinical and Regulatory Aspect," *Transfusion and Apheresis Science.* 52(2):240-244.

Klein, H.G. et al. (Mar. 1, 2005). "Pathogen Inactivation Technology: Cleaning the Blood Supply," *Journal of Internal Medicine,* 257(3):224-237.

Lozano, M. et al. (Nov. 1, 2013). "Pathogen Inactivation: Coming of Age," *Current Opinion in Hematology,* 20(6):540-545.

Mintz, P.D. et al. (2000). "SP71—Preparation of Cryoprecipitate From Photochemically Treated Fresh Frozen Plasma," *Transfusion* 40:63S.

Mintz, P.D. et al. (2004). "Therapeutic Plasma Exchange (TPE) for Thrombotic Thrombocytopenic Purpura (TTP) Using Plasma Prepared With Photochemical Treatment (INTERCEPT Plasma), Abstract 838," *Blood* 104(11):239a.

Mintz, P.D. et al. (May 1, 2006). "Photochemically Treated Fresh Frozen Plasma for Transfusion of Patients with Acquired Coagulopathy of Liver Disease,"107(9):3753-3760. Retrieved from the Internet:URL:http://www.bloodjournal.org/content/107/9/3753.full.pdf [retrieved on Sep. 21, 2016]*Discussion*.

Mintz, P.D. et al. (Oct. 2006). "A Randomized, Controlled Phase III trial of Therapeutic Plasma Exchange With Fresh-Frozen Plasma (FFP) Prepared With Amotosalen and Ultraviolet a Light Compared to Untreated FFP in Thrombotic Thrombocytopenic Purpura," *Hemapheresis.* 46(10):1693-1704.

Mirasol (TerumoBCT) "Pathogen Reduction Technology (PRT) System: A Proven Approach to Improved Blood Safety," retrieved from <https://www.terumobct.com/miraso.pdf>, last visited Jun. 18, 2018. 8 pages.

Nascimento, B. et al. (Dec. 1, 2014). "Cryoprecipitate Therapy," *British Journal of Anaesthesia* 113(6):922-934.

*New and Emerging Health Technology Report: Technologies for the Inactivation/Reduction of Pathogens in Blood Products,* (Jul. 2011) 108 pages.

(56) References Cited

OTHER PUBLICATIONS

Octaplas, Octapharma, “Highlights of Prescribing Information,” retrieved from <https://www.fda.gov/downloads/biologicsbloodvaccines/ . . . /ucm336161.pdf>, lasted visited Aug. 22, 2018, 8 pages.
Picker, S.M. (Jan. 1, 2013). “Pathogen Reduction Technologies: The Best Solution for Safer Blood?” *Journal of Blood Disorders & Transfusion,* 3(5), 5 pages.
Prodouz, K.N. et al., (1992). “Effects of Two Viral Inactivation Methods on Platelets: Laser-UV133 Radiation and Merocyanine 540-Mediated Photoinactivation,” *Blood Cells* 18(1):101-14.
Radosevich, M. et al. (2010, e-pub. Jul. 29, 2009). “Intravenous Immunoglobulin G: Trends in Production Methods, Quality Control and Quality Assurance,” *Vox Sanguinis* 98:12-28.
Rummler, S. et al. (2013). “Efficacy and Safety of Pathogen Reduced Plasma in Plasma Therapy in Germany,” *Transfusion* 53(supp. 2):77A.
Sailliol, A. et al. (Jan. 2013). “The Evolving Role of Lyophilized Plasma in Remote Damage Control Resuscitation in The French Armed Forces Health Service,” *Transfusion* 53(Suppl. 1):65S-71S.
Sheffield, W.P. et al. (2016). “Stability of Coagulation Protein Activities in Single Units of Pools of Cryoprecipitate During Storage at 20-24° C. for Up to 24 H,” *VoxSanguinis* 110:12-19.
Sofer, G. (Aug. 2002). “Virus Inactivation in the 1990s—and into the 21st Century Part 2, Red Blood Cells and Platelets,” *BioPharm,* pp. 45-49.
Solheim et al. (Jan. 2000). “Viral Safety of Solvent/Detergent-Treated Plasma,” *Transfusion* 40(1):84-90.
Spivey, M.A. et al. (1992). “Postfiltration Factor VIII and Fibrinogen Levels in Cryoprecipitate Stored at Room Temperature and at 1 to 6° C.,” *Transfusion* 32(4):340-343.
Theraflex (MacoPharma) MB Plasma System, retrieved from <https://blood-safety.macopharma.com/category/products/theraflex-mb-plasma-products/product.pdf> lasted visited Jun. 18, 2018, 4 pages.
Ward, D.M. (2011, e-pub. Aug. 31, 2011). “Conventional Apheresis Therapies: A Review,” *J. Clin. Apheresis* 26:230-238.
Winters, J.L. (2012). “Plasma Exchange: Concepts, Mechanisms, and an Overview of The American Society for Apheresis Guidelines,” *Hematology* 2012:7-12.
Wong, H. et al. (Sep. 22, 2016). “Cryoprecipitate Transfusion: Current Perspectives,” *International Journal of Clinical Transfusion Medicine* 4:89-97.
International Preliminary Report on Patentability, dated Apr. 28, 2018, for PCT Application No. PCT/US2016/058318, filed Oct. 21, 2016, 13 pages.
International Search Report, dated Dec. 20, 2016, for PCT Application No. PCT/US2016/058318, 4 pages.
International Preliminary Report on Patentability dated Dec. 26, 2017, for PCT Application No. PCT/US2016/039428, filed Jun. 24, 2016, 12 pages.
International Search Report dated Dec. 13, 2016, for PCT Application No. PCT/US2016/039428, internationally filed on Jun. 24, 2016, 8 pages.
Written Opinion dated Dec. 13, 2016, for PCT Application No. PCT/US2016/039428, filed on Jun. 24, 2016, 11 pages.
Written Opinion dated Dec. 20, 2016, for PCT Application No. PCT/US2016/058318, filed on Jun. 24, 2016, 12 pages.

* cited by examiner

PLASMA COMPOSITIONS AND METHODS OF USE THEREOF

CROSS REFERENCE TO RELATED APPLICATIONS

This application is the National Stage filing of PCT/US2016/058318 entitled "PLASMA COMPOSITIONS AND METHODS OF USE THEREOF" with the International Filing Date of Oct. 21, 2016 which claims the priority benefit of U.S. Provisional Application Ser. No. 62/245,926, filed Oct. 23, 2015; 62/268,462, filed Dec. 16, 2015; and 62/354,653, filed Jun. 24, 2016; each of which is incorporated herein by reference in its entirety.

TECHNICAL FIELD

The methods described herein generally relate to the preparation and use of plasma compositions. More particularly, the present disclosure relates to pathogen-inactivated plasma compositions and their use in improved treatment methods using such compositions for therapeutic plasma exchange or infusion.

BACKGROUND

Blood collection and processing serves a critical role in healthcare worldwide, and millions of units of donated whole blood are collected by blood banks each year. While some whole blood units collected from donors are stored and used for transfusion, most whole blood is instead separated into its clinically therapeutic components of red blood cells, platelets and plasma, for individual storage and use in treating different medical needs and conditions requiring one or more of the particular blood components. Additionally, other blood derived products may be produced through fractionation procedures, such as for example, intravenous immunoglobulin G (IVIG), a product obtained by fractionation of human plasma (Radosevich et al., 2010, Vox Sanguinis, 98: 12-28).

Cryoprecipitate (also known as "cryo") is a blood product comprising a portion of plasma rich in coagulation factors. Cyroprecipitate, also referred to as cryoprecipitated antihaemophilic factor (AHF), cryoprecipitated AHF, is prepared by slow, controlled thawing of frozen plasma (e.g., whole blood-derived fresh frozen plasma, or FFP), for example between 1° and 6° C. (e.g., 4±2° C.), which results in the formation of a white precipitate, and then recovering the precipitate following separation from the remaining liquid plasma portion, such as by refrigerated centrifugation. The remaining liquid plasma portion, also referred to herein as "supernatant" and various other terminology, such as "cryo-poor plasma" (CPP), "cryosupernatant", "cryoprecipitate-reduced plasma", or "cryo-reduced plasma", is removed from the cryoprecipitate bag and the isolated cold-insoluble precipitate is re-suspended in a portion of the plasma (e.g., the cryo-poor plasma) left behind and generally re-frozen within 1 hour, and stored frozen until needed for transfusion. The cryo-poor plasma contains plasma proteins not partitioned with the cryoprecipitate and generally is used for plasma fractionation to produce various components (e.g., plasma factors), as well as for certain, very limited therapeutic applications.

Cryoprecipitate serves as a source of fibrinogen, Factor VIII, Factor XIII, vWF, and fibronectin. This component is used in the control of bleeding associated with fibrinogen deficiency and to treat Factor XIII deficiency when volume considerations preclude the use of frozen plasma and recombinant proteins are not available. It is also indicated as second-line therapy for von Willebrand disease and hemophilia A (Factor VIII deficiency).

In addition to the primary use of plasma in transfusions to correct deficiencies of clotting factors or coagulopathy in patients with active bleeding, such as for example surgery and trauma, plasma (e.g., FFP) and plasma derived components (e.g., IVIG) may be used for treatment of various diseases or conditions. For example, immunotherapy using therapeutic plasma exchange (TPE) or intravenous immunoglobulin (IVIG) or a combination of both has been used for treatment of a variety of diseases or conditions. Many such the diseases or conditions have been categorized by the American Society for Apheresis (ASFA) based on literature guidance. TPE is a therapeutic procedure using bulk removal of plasma from patients. In a TPE process, blood is removed and separated into plasma and cellular components (e.g., platelets, red blood cells), followed by mixing of the cellular components with some form of replacement fluid, and reinfusion into the patient (Winters, 2012, Hematology ASH Education Book 2012:7-12). TPE removes pathologic substances such as pathologic antibodies (e.g., autoantibodies), immune complexes, and cytokines, and may have additional immunomodulatory effects. Because TPE involves the bulk removal of plasma, anything circulating in the plasma will be removed, leading to a temporary decline in normal plasma components such as factor V, factor VII, factor VIII, factor IX, factor X, VWF and fibrinogen. Depending on the medical indication, plasma that is removed can be replaced with human albumin (e.g., 4%-5% in physiologic saline) which is relatively common, or alternatively additional plasma (e.g., fresh frozen plasma, FFP), or even the patient's own plasma after a secondary purification procedure (Ward, 2011, J. Clin. Apheresis 26:230-238).

There remains a need for improved compositions and methods for treatment of various diseases and conditions through the use of therapeutic plasma exchange or infusion.

SUMMARY

The pathogen-inactivated plasma compositions and methods described herein are useful for the treatment of various diseases or conditions, including, for example, in providing improved treatment methods using such plasma compositions for therapeutic plasma exchange or infusion.

In one aspect, the present disclosure provides a composition comprising a cryoprecipitate suitable for infusion into a subject at least 1 day after thawing, wherein the cryoprecipitate is pathogen-inactivated. In some embodiments, the composition is suitable for infusion into a subject at least 3 days after thawing. In some embodiments, the composition is suitable for infusion into a subject at least 5 days after thawing. In some embodiments, the composition is suitable for infusion into a subject at least 7 days after thawing. In some embodiments, the composition comprises less than 80 IU of factor VIII per unit of cryoprecipitate. In some embodiments, the composition comprises less than 50 IU of factor VIII per unit of cryoprecipitate. In some embodiments, the composition comprises at least 150 mg of fibrinogen per unit of cryoprecipitate. In some embodiments, the composition further comprises plasma of a volume between about 15 mL and about 20 mL. In some embodiments, the composition comprises cryoprecipitate obtained from about 600 mL of pathogen-inactivated plasma. In some embodiments, the composition comprises a first cryoprecipitate obtained from about 600 mL of pathogen-inactivated plasma and a second cryoprecipitate obtained from about 600 mL of pathogen-inactivated plasma, wherein the first and the second cryoprecipitates are combined prior to re-freezing for storage. In some embodiments, the composition comprises cryoprecipitate obtained from at least about 600 mL and less than 650 mL of pathogen-inactivated plasma. In some embodiments, the composition comprises a first cryoprecipitate obtained from at least about 600 mL and less than 650 mL of pathogen-inactivated plasma and a second cryoprecipitate obtained from at least about 600 mL and less than 650 mL of pathogen-inactivated plasma, wherein the first and the second cryoprecipitates are combined prior to re-freezing for storage. In some embodiments, the composition further comprises plasma of a volume between about 50 mL and about 60 mL. In some embodiments, the composition is stored at room temperature for the at least 1 day after thawing. In some embodiments, the cryoprecipitate has been pathogen-inactivated by photochemical inactivation. In some embodiments, the cryoprecipitate has been pathogen-inactivated by photoinactivation with psoralen. In some embodiments, the psoralen is amotosalen.

In another aspect, the present disclosure provides a method of preparing a cryoprecipitate for infusion into a subject comprising a) preparing a cryoprecipitate from pathogen-inactivated plasma; b) freezing the cryoprecipitate; and c) thawing the frozen cryoprecipitate, wherein the resulting cryoprecipitate of step c) is suitable for infusion into a subject at least 1 day after thawing. In some embodiments, the method further comprises testing the thawed cryoprecipitate for fibrinogen. In some embodiments, the method does not comprise testing the thawed cryoprecipitate for factor VIII. In some embodiments, the cryoprecipitate is prepared from about 600 mL of pathogen-inactivated plasma. In some embodiments, the method further comprises combining a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to steps b) and c). In some embodiments, the cryoprecipitate is prepared from at least about 600 mL and less than 650 mL of pathogen-inactivated plasma. In some embodiments, the method further comprises combining a first cryoprecipitate prepared from at least about 600 mL and less than 650 mL of pathogen-inactivated plasma and a second cryoprecipitate prepared from at least about 600 mL and less than 650 mL of pathogen-inactivated plasma, wherein the first and the second cryoprecipitates are combined prior to steps b) and c). In some embodiments, the resulting cryoprecipitate of step c) is suitable for infusion into a subject at least 3 days after thawing. In some embodiments, the resulting cryoprecipitate of step c) is suitable for infusion into a subject at least 5 days after thawing. In some embodiments, the resulting cryoprecipitate of step c) is suitable for infusion into a subject at least 7 days after thawing.

In yet another aspect, the present disclosure provides a method of infusing a cryoprecipitate into a subject comprising a) preparing a cryoprecipitate from pathogen-inactivated plasma; b) freezing the cryoprecipitate; c) thawing the frozen cryoprecipitate; and d) infusing the thawed cryoprecipitate into a subject, wherein the infusion occurs at least 1 day after thawing the frozen cryoprecipitate. In some embodiments, the method further comprises testing the thawed cryoprecipitate for fibrinogen. In some embodiments, the method does not comprise testing the thawed cryoprecipitate for factor VIII before transfusing the thawed cryoprecipitate. In some embodiments, the cryoprecipitate is prepared from about 600 mL of pathogen-inactivated plasma. In some embodiments, the method further comprises combining a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to step b). In some embodiments, the cryoprecipitate is prepared from at least about 600 mL and less than 650 mL of pathogen-inactivated plasma. In some embodiments, the method further comprises combining a first cryoprecipitate prepared from at least about 600 mL and less than 650 mL of pathogen-inactivated plasma and a second cryoprecipitate prepared from at least about 600 mL and less than 650 mL of pathogen-inactivated plasma, wherein the first and the second cryoprecipitates are combined prior to step b).

In some embodiments of any of the above embodiments, the resulting cryoprecipitate of step c) comprises less than 80 IU of factor VIII per unit of cryoprecipitate. In some embodiments, the resulting cryoprecipitate of step c) comprises less than 50 IU of factor VIII per unit of cryoprecipitate. In some embodiments of any of the above embodiments, the resulting cryoprecipitate of step c) comprises at least 150 mg of fibrinogen per unit of cryoprecipitate. In some embodiments, the cryoprecipitate of step a) further comprises plasma of a volume between about 15 mL and about 20 mL. In some embodiments, the cryoprecipitate of step a) further comprises plasma of a volume between about 50 mL and about 60 mL. In some embodiments of any of the above embodiments, the plasma has been pathogen-inactivated by photochemical inactivation. In some embodiments, the cryoprecipitate has been pathogen-inactivated by photoinactivation with psoralen. In some embodiments, the psoralen is amotosalen. In some embodiments of any of the above embodiments, the subject is a human.

In still another aspect, the present disclosure provides a kit comprising a) a container; b) a pathogen-inactivated cryoprecipitate; and c) instructions for using the pathogen-inactivated cryoprecipitate in an infusion into a subject, wherein the instructions indicate that the cryoprecipitate is suitable for infusion into the subject for up to about 5 days after thawing.

In still another aspect, the present disclosure provides a method of infusing a cryoprecipitate into a subject, comprising infusing into the subject the composition of any of the above embodiments.

In still another aspect, the present disclosure provides a method infusing a cryoprecipitate into a subject, comprising infusing into the subject a cryoprecipitate produced by the method of any of the above embodiments.

In still another aspect, the present disclosure provides a cryoprecipitate produced by the method of any of the above embodiments.

In still another aspect, the present disclosure provides a composition comprising a cryoprecipitate suitable for infusion into a subject at least 1 day after thawing, wherein the cryoprecipitate is pathogen-inactivated. In some embodiments, the composition is suitable for infusion into a subject at least 3 days after thawing. In some embodiments, the composition is suitable for infusion into a subject at least 5 days after thawing. In some embodiments, the composition comprises cryoprecipitate prepared from at least about 550 mL and less than about 650 mL of pathogen-inactivated plasma. In some embodiments, the composition comprises cryoprecipitate prepared from about 600 mL of pathogen-inactivated plasma. In some embodiments, the composition comprises cryoprecipitate prepared from 3 units of pathogen-inactivated plasma. In some embodiments, the composition comprises a first cryoprecipitate prepared from at least about 550 mL and less than 650 mL of pathogen-inactivated plasma and a second cryoprecipitate prepared from at least about 550 mL and less than 650 mL of pathogen-inactivated plasma, wherein the first and the second cryoprecipitates are combined prior to re-freezing for storage. In some embodiments, the composition comprises a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to re-freezing for storage. In some embodiments, the composition comprises a first cryprecipitate prepared from 3 units of pathogen-inactivated plasma and a second cryoprecipitate prepared from 3 units of pathogen-inactivated plasma, wherein the first and the second cryoprecipitates are combined prior to re-freezing for storage. In some embodiments, the composition comprises cryoprecipitate prepared from 6 units of pathogen-inactivated plasma. In some embodiments, the composition comprises cryoprecipitate prepared from plasma obtained from one donor. In some embodiments, the composition comprises cryoprecipitate prepared from plasma obtained from 2-6 donors. In some embodiments, the composition comprises less than 80 IU of factor VIII per unit of cryoprecipitate. In some embodiments, the composition comprises less than 50 IU of factor VIII per unit of cryoprecipitate. In some embodiments, the composition comprises 80-100 IU of factor VIII per unit of cryoprecipitate. In some embodiments, the composition comprises at least 80 IU of factor VIII. In some embodiments, the composition comprises 80-240 IU of factor VIII. In some embodiments, the composition comprises 80-480 IU of factor VIII. In some embodiments, the amount of factor VIII is determined from cryoprecipitate sampled within about 2 hours after thawing. In some embodiments, the amount of factor VIII is determined from cryoprecipitate sampled about 1 day after thawing. In some embodiments, the amount of factor VIII is determined from cryoprecipitate sampled about 3 days after thawing. In some embodiments, the amount of factor VIII is determined from cryoprecipitate sampled about 5 days after thawing. In some embodiments, the composition comprises at least 150 mg of fibrinogen per unit of cryoprecipitate. In some embodiments, the composition comprises at least 250 mg of fibrinogen per unit of cryoprecipitate. In some embodiments, the composition comprises at least 750 mg of fibrinogen. In some embodiments, the composition comprises at least 1500 mg of fibrinogen. In some embodiments, each unit of cryoprecipitate is prepared from 180-250 mL of pathogen-inactivated plasma. In some embodiments, the composition further comprises plasma of a volume between about 5 mL and about 20 mL per unit of cryoprecipitate. In some embodiments, the composition further comprises plasma of a volume greater than about 1 mL and less than or equal to about 75 mL. In some embodiments, the composition further comprises plasma of a volume between about 50 mL and about 60 mL. In some embodiments, the composition further comprises plasma of a volume between about 30 mL and about 120 mL. In some embodiments, the composition is stored at room temperature for at least 1 day after thawing. In some embodiments, the composition is stored at between about 2° C. and about 6° C. for at least 1 day after thawing. In some embodiments, the cryoprecipitate has been pathogen-inactivated by photochemical inactivation. In some embodiments, the cryoprecipitate has been pathogen-inactivated by photochemical inactivation with a psoralen. In some embodiments, the psoralen is amotosalen. In some embodiments, the cryoprecipitate is prepared from plasma that has been pathogen-inactivated in a first container suitable for photochemical inactivation of the plasma under sterile conditions; wherein the first container is coupled to a compound absorption device (CAD) such that the pathogen-inactivated plasma can be transferred from the first container to the CAD under sterile conditions; and wherein the cryoprecipitate is contained within one or more second containers, each of which is coupled to the CAD such that the pathogen-inactivated plasma can be transferred from the CAD to the one or more second containers under sterile conditions, and each of which is suitable for freezing the pathogen-inactivated plasma followed by thawing of the pathogen-inactivated plasma under conditions that provide for the formation of the cryoprecipitate. In some embodiments, each of the one or more second containers is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the one or more second containers. In some embodiments, the cryoprecipitate is prepared from plasma that has been pathogen-inactivated in a first container suitable for photochemical inactivation of the plasma under sterile conditions; wherein the first container is coupled to a compound absorption device (CAD) such that the pathogen-inactivated plasma can be transferred from the first container to the CAD under sterile conditions; wherein the CAD is coupled to one or more second containers, each of which is coupled to the CAD such that the pathogen-inactivated plasma can be transferred from the CAD to the one or more second containers under sterile conditions; and wherein the cryoprecipitate is contained within a third container configured to be coupled to one or more second containers, such that the pathogen-inactivated plasma can be transferred from the CAD to the one or more second containers to the third container under sterile conditions, wherein the third container is suitable for freezing the pathogen-inactivated plasma followed by thawing of the pathogen-inactivated plasma under conditions that provide for the formation of the cryoprecipitate. In some embodiments, the third container is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the third container. In some embodiments, the composition is contained within a container that further comprises a label indicating that the composition is suitable for use for at least about 1 day after thawing. In some embodiments, the composition is contained within a container that further comprises a label indicating that the composition is suitable for use for at least about 3 days after thawing. In some embodiments, the composition is contained within a container that further comprises a label indicating that the composition is suitable for use for at least about 5 days after thawing. In some embodiments, the cryoprecipitate is prepared from plasma other than group O plasma.

In still another aspect, the present disclosure provides a method of preparing a cryoprecipitate for infusion into a subject comprising: a) preparing a cryoprecipitate from pathogen-inactivated plasma; b) freezing the cryoprecipitate; and c) thawing the frozen cryoprecipitate, wherein the resulting cryoprecipitate of step c) is suitable for infusion into a subject at least 1 day after thawing. In some embodiments, the thawed cryoprecipitate comprises at least about 150 mg of fibrinogen per unit of cryoprecipitate. In some embodiments, the thawed cryoprecipitate comprises at least about 750 mg of fibrinogen. In some embodiments, the method does not comprise determining the level of factor VIII before infusing the thawed cryoprecipitate. In some embodiments, the method further comprises determining the level of factor VIII in the thawed cryoprecipitate. In some embodiments, the cryoprecipitate is prepared from at least about 550 mL and less than about 650 mL of pathogen-inactivated plasma. In some embodiments, the cryoprecipitate is prepared from about 600 mL of pathogen-inactivated plasma. In some embodiments, the method further comprises combining a first cryoprecipitate prepared from at least about 550 mL and less than about 650 mL of pathogen-inactivated plasma and a second cryoprecipitate prepared from at least about 550 mL and less than about 650 mL of pathogen-inactivated plasma, wherein the first and the second cryoprecipitates are combined prior to steps b) and c). In some embodiments, the method further comprises combining a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to steps b) and c). In some embodiments, the method further comprises combining a first cryprecipitate prepared from 3 units of pathogen-inactivated plasma and a second cryoprecipitate prepared from 3 units of pathogen-inactivated plasma, wherein the first and the second cryoprecipitates are combined prior to steps b) and c). In some embodiments, the resulting cryoprecipitate of step c) is suitable for infusion into a subject at least 3 days after thawing. In some embodiments, the resulting cryoprecipitate of step c) is suitable for infusion into a subject at least 5 days after thawing. In another aspect, provided herein is a method of infusing a cryoprecipitate into a subject comprising: a) preparing a cryoprecipitate from pathogen-inactivated plasma; b) freezing the cryoprecipitate; c) thawing the frozen cryoprecipitate; and d) infusing the thawed cryoprecipitate into a subject, wherein the infusion occurs at least 1 day after thawing the frozen cryoprecipitate. In some embodiments, the thawed cryoprecipitate comprises at least about 150 mg of fibrinogen per unit of cryoprecipitate. In some embodiments, the thawed cryoprecipitate comprises at least about 750 mg of fibrinogen. In some embodiments, the method does not comprise determining the level of factor VIII before infusing the thawed cryoprecipitate. In some embodiments, the method further comprises determining the level of factor VIII in the thawed cryoprecipitate before infusing the thawed cryoprecipitate. In some embodiments, the cryoprecipitate is prepared from at least about 550 mL and less than about 650 mL of pathogen-inactivated plasma. In some embodiments, the cryoprecipitate is prepared from about 600 mL of pathogen-inactivated plasma. In some embodiments, the method further comprises combining a first cryoprecipitate prepared from at least about 550 mL and less than about 650 mL of pathogen-inactivated plasma and a second cryoprecipitate prepared from at least about 550 mL and less than about 650 mL of pathogen-inactivated plasma, wherein the first and the second cryoprecipitates are combined prior to steps b) and c). In some embodiments, the method further comprises combining a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to steps b) and c). In some embodiments, the method further comprises combining a first cryprecipitate prepared from 3 units of pathogen-inactivated plasma and a second cryoprecipitate prepared from 3 units of pathogen-inactivated plasma, wherein the first and the second cryoprecipitates are combined prior to steps b) and c). In some embodiments, the resulting cryoprecipitate of step c) comprises less than 80 IU of factor VIII per unit of cryoprecipitate. In some embodiments, the resulting cryoprecipitate of step c) comprises at least about 80 IU of factor VIII. In some embodiments, the resulting cryoprecipitate of step c) comprises less than 50 IU of factor VIII per unit of cryoprecipitate. In some embodiments of any of the above embodiments, the resulting cryoprecipitate of step c) comprises at least 150 mg of fibrinogen per unit of cryoprecipitate. In some embodiments of any of the above embodiments, the resulting cryoprecipitate of step c) comprises at least 750 mg of fibrinogen. In some embodiments of any of the above embodiments, the cryoprecipitate of step a) further comprises plasma of a volume between about 5 mL and about 20 mL per unit of cryoprecipitate. In some embodiments, the cryoprecipitate of step a) further comprises plasma of a volume greater than about 1 mL and less than or equal to about 75 mL. In some embodiments, the cryoprecipitate of step a) further comprises plasma of a volume between about 50 mL and about 60 mL. In some embodiments, the cryoprecipitate of step a) further comprises plasma of a volume between about 30 mL and about 120 mL. In some embodiments of any of the above embodiments, the plasma has been pathogen-inactivated by photochemical inactivation. In some embodiments, the cryoprecipitate has been pathogen-inactivated by photochemical inactivation with a psoralen. In some embodiments, the psoralen is amotosalen. In some embodiments of any of the above embodiments, the cryoprecipitate is prepared from plasma that has been pathogen-inactivated in a first container suitable for photochemical inactivation of the plasma under sterile conditions; wherein the first container is coupled to a compound absorption device (CAD) such that the pathogen-inactivated plasma can be transferred from the first container to the CAD under sterile conditions; and wherein the cryoprecipitate is frozen and thawed in steps b) and c) within one or more second containers, each of which is coupled to the CAD such that the pathogen-inactivated plasma can be transferred from the CAD to the one or more second containers under sterile conditions, and each of which is suitable for freezing the pathogen-inactivated plasma followed by thawing of the pathogen-inactivated plasma under conditions that provide for the formation of the cryoprecipitate. In some embodiments, each of the one or more second containers is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the one or more second containers. In some embodiments, the cryoprecipitate is prepared from plasma that has been pathogen-inactivated in a first container suitable for photochemical inactivation of the plasma under sterile conditions; wherein the first container is coupled to a compound absorption device (CAD) such that the pathogen-inactivated plasma can be transferred from the first container to the CAD under sterile conditions; and wherein the cryoprecipitate is frozen and thawed in steps b) and c) within a third container configured to be coupled to one or more second containers, such that the pathogen-inactivated plasma can be transferred from the CAD to the one or more second containers to the third container under sterile conditions, wherein the third container is suitable for freezing the pathogen-inactivated plasma followed by thawing of the pathogen-inactivated plasma under conditions that provide for the formation of the cryoprecipitate. In some embodiments, the third container is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the third container. In some embodiments of any of the above embodiments, the subject is a human.

In still another aspect, the present disclosure provides a kit comprising: a) a container; b) a pathogen-inactivated cryoprecipitate; and c) instructions for using the pathogen-inactivated cryoprecipitate in an infusion into a subject, wherein the instructions indicate that the cryoprecipitate is suitable for infusion into the subject for up to about 5 days after thawing.

In still another aspect, the present disclosure provides a kit comprising: a) a container; b) a pathogen-inactivated cryoprecipitate; and c) a label indicating that the pathogen-inactivated cryoprecipitate is suitable for use for up to about 5 days after thawing.

In still another aspect, the present disclosure provides a method of infusing a cryoprecipitate into a subject, comprising infusing into the subject the composition of any of the above embodiments.

In still another aspect, the present disclosure provides a method of infusing a cryoprecipitate into a subject, comprising infusing into the subject a cryoprecipitate produced by any of the above embodiments.

In still another aspect, the present disclosure provides a cryoprecipitate produced by any of the above embodiments.

In still another aspect, the present disclosure provides a method of preparing a pooled cryosupernatant for infusion into a subject comprising: a) freezing at least a first pathogen-inactivated plasma and a second pathogen-inactivated plasma, wherein the first and the second pathogen-inactivated plasmas each have a volume of at least about 550 mL and less than about 650 mL; b) thawing the first pathogen-inactivated plasma under conditions that provide for the formation of a first precipitate and a first supernatant, and thawing the second pathogen-inactivated plasma under conditions that provide for the formation of a second precipitate and a second supernatant; c) separating the first and the second supernatants from the first and the second precipitates to form a first crosupernatant and a second cryosupernatant; and d) combining the first and the second cryosupernatants to form a pooled cryosupernatant. In some embodiments, the first and the second pathogen-inactivated plasmas each have a volume of about 600 mL. In some embodiments, step a) further comprises freezing at least a third pathogen-inactivated plasma and a fourth pathogen-inactivated plasma, wherein the third and the fourth pathogen-inactivated plasmas each have a volume of at least about 550 mL and less than 650 mL; step b) further comprises thawing the third pathogen-inactivated plasma under conditions that provide for the formation of a third precipitate and a third supernatant, and thawing the fourth pathogen-inactivated plasma under conditions that provide for the formation of a fourth precipitate and a fourth supernatant; step c) further comprises separating the third and the fourth supernatants from the third and the fourth precipitates to form a third cryosupernatant and a fourth cryosupernatant; the pooled cryosupernatant formed in step d) is a first pooled supernatant, and step d) further comprises combining the third and the fourth cryosupernatants to form a second pooled cryosupernatant; and the method further comprises e) combining the first pooled cryosupernatant and the second pooled cryosupernatant. In some embodiments, the third and the fourth pathogen-inactivated plasmas each have a volume of about 600 mL. In some embodiments, the first and/or the second pathogen-inactivated plasma have been pathogen-inactivated by photochemical inactivation. In some embodiments, the one or more of the first, second, third, and fourth pathogen-inactivated plasmas have been pathogen-inactivated with a psoralen. In some embodiments, the psoralen is amotosalen. In some embodiments, one or more of the first, second, third, and fourth pathogen-inactivated plasmas have been pathogen-inactivated in a first container suitable for photochemical inactivation of plasma under sterile conditions, wherein the first container is coupled to a compound absorption device (CAD) such that the pathogen-inactivated plasma can be transferred from the first container to the CAD under sterile conditions. In some embodiments, one or more of the first, second, third, and fourth pathogen-inactivated plasmas is frozen in step a) and thawed in step b) within one or more second containers, each of which is coupled to the CAD such that the pathogen-inactivated plasma can be transferred from the CAD to the one or more second containers under sterile conditions, and each of which is suitable for freezing the pathogen-inactivated plasma followed by thawing of the pathogen-inactivated plasma under conditions that provide for the formation of the cryoprecipitate. In some embodiments, one or more of the first, second, third, and fourth pathogen-inactivated plasmas is frozen in step a) and thawed in step b) within a third container configured to be coupled to the one or more second containers, such that the pathogen-inactivated plasma can be transferred from the CAD to the one or more second containers to the third container under sterile conditions, wherein the third container is suitable for freezing the pathogen-inactivated plasma followed by thawing of the pathogen-inactivated plasma under conditions that provide for the formation of the cryoprecipitate. In some embodiments, one or more of the first, second, third, and fourth supernatants is separated from one or more of the the first, second, third, and fourth precipitates in step c) within one or more fourth containers, each of which is configured to be coupled to the one or more second containers or to the third container such that the supernatant can be transferred from the one or more second containers or the third container to the one or more fourth containers under sterile conditions to afford a pathogen-inactivated cryosupernatant contained within the one or more fourth containers and a pathogen-inactivated cryoprecipitate contained within the one or more second containers or the third container.

In still another aspect, the present disclosure provides a method of infusing a cryosupernatant into a subject, comprising infusing into the subject a cryosupernatant produced by the method of any of the above embodiments.

In still another aspect, the present disclosure provides a processing set for preparing a pathogen-inactivated cryoprecipitate, comprising a) a first container within which one or more units of a plasma can be photochemically inactivated in the presence of a psoralen under sterile conditions; b) a compound absorption device (CAD) coupled to the first container such that the one or more units of plasma can be transferred from the first container to the compound absorption device under sterile conditions; and c) one or more second containers, each of which is coupled to the compound absorption device such that the one or more units of plasma can be transferred from the compound absorption device to the one or more second containers under sterile conditions to provide pathogen-inactivated plasma suitable for infusion into a subject, wherein the one or more second containers is suitable for freezing the pathogen-inactivated plasma followed by thawing of the pathogen-inactivated plasma under conditions that provide for the formation of a precipitate and a supernatant. In some embodiments, each of the one or more second containers is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the one or more second containers.

In still another aspect, the present disclosure provides a processing set for preparing a pathogen-inactivated cryoprecipitate, comprising a) a first container within which one or more units of a plasma can be photochemically inactivated in the presence of a psoralen under sterile conditions; b) a compound absorption device (CAD) coupled to the first container such that the one or more units of plasma can be transferred from the first container to the compound absorption device under sterile conditions; c) one or more second containers, each of which is coupled to the compound absorption device such that the one or more units of plasma can be transferred from the compound absorption device to the one or more second containers under sterile conditions to provide pathogen-inactivated plasma suitable for infusion into a subject; and d) a third container, which is configured to be coupled to the one or more second containers such that the pathogen-inactivated plasma can be transferred from the one or more second containers to the third container under sterile conditions, wherein the third container is suitable for freezing the pathogen-inactivated plasma followed by thawing of the pathogen-inactivated plasma under conditions that provide for the formation of a precipitate and a supernatant. In some embodiments, the third container is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the third container. In some embodiments, the processing set further comprises an additional container suitable for mixing the one or more units of plasma with a pathogen inactivation compound, wherein the additional container is coupled to the first container such that the one or more units of plasma in admixture with the pathogen-inactivating compound can be transferred from the additional container to the first container under sterile conditions. In some embodiments, the processing set further comprises one or more fourth containers, each of which is configured to be coupled to the one or more second containers or to the third container such that the supernatant can be transferred from the one or more second containers or the third container to the one or more fourth containers under sterile conditions to provide a pathogen-inactivated cryosupernatant contained within the one or more fourth containers and a pathogen-inactivated cryoprecipitate contained within the one or more second containers or the third container. In some embodiments, the third container is coupled to the one or more second containers such that the supernatant can be transferred from the one or more second containers to the third container under sterile conditions to afford a pathogen-inactivated cryosupernatant contained within the third container and a pathogen-inactivated cryoprecipitate contained within the one or more second containers. In some embodiments, the third container is configured to be coupled to the one or more second containers such that the pathogen-inactivated plasma can be transferred from the one or more second containers to the third container under sterile conditions; wherein the third container is suitable for freezing the pathogen-inactivated plasma followed by thawing of the pathogen-inactivated plasma under conditions that provide for the formation of a precipitate and a supernatant; and wherein each of the one or more fourth containers is configured to be coupled to the third container such that the supernatant can be transferred from the third container to the one or more fourth containers under sterile conditions to afford a pathogen-inactivated cryosupernatant contained within the one or more fourth containers and a pathogen-inactivated cryoprecipitate contained within the third container.

In still another aspect, the present disclosure provides a method of preparing a cryoprecipitate for infusion into a subject comprising: a) preparing a cryoprecipitate from pathogen-inactivated plasma; and b) freezing the cryoprecipitate; wherein the cryoprecipitate is suitable for infusion into the subject for up to about 5 days after thawing. In some embodiments, the cryoprecipitate is prepared from at least about 550 mL and less than about 650 mL of pathogen-inactivated plasma. In some embodiments, the cryoprecipitate is prepared from about 600 mL of pathogen-inactivated plasma. In some embodiments, the method further comprises combining a first cryoprecipitate prepared from at least about 550 mL and less than about 650 mL of pathogen-inactivated plasma and a second cryoprecipitate prepared from at least about 550 mL and less than about 650 mL of pathogen-inactivated plasma, wherein the first and the second cryoprecipitates are combined prior to step b). In some embodiments, the first cryoprecipitate is prepared from about 600 mL of pathogen-inactivated plasma, and wherein the second cryoprecipitate is prepared from about 600 mL of pathogen-inactivated plasma. In some embodiments, the method further comprises combining a first cryprecipitate prepared from 3 units of pathogen-inactivated plasma and a second cryoprecipitate prepared from 3 units of pathogen-inactivated plasma, wherein the first and the second cryoprecipitates are combined prior to step b).

In still another aspect, the present disclosure provides a method of treating a disease or condition indicated for treatment by plasma exchange in a subject in need thereof, comprising administering to the subject a therapeutically effective amount of pathogen-inactivated plasma composition by plasma exchange. In some embodiments, the disease or condition is indicated for treatment with albumin by plasma exchange. In some embodiments, the disease or condition is a disease or condition set forth in the present disclosure. In some embodiments, the disease or condition is Guillain-Barré syndrome, chronic inflammatory demyelinating polyneuropathy, myasthenia gravis, a paraproteinemic polyneuropathy, Goodpasture's syndrome, or cryoglobulinemia. In some embodiments, the disease or condition is other than thrombocytopenic purpura (TTP) or hemolytic-uremic syndrome (HUS). In some embodiments, the disease or condition is burn shock resuscitation. In some embodiments, the pathogen-inactivated plasma composition comprises pathogen-inactivated plasma that has not been previously frozen. In some embodiments, the pathogen-inactivated plasma composition comprises pathogen-inactivated frozen plasma. In some embodiments, the pathogen-inactivated plasma composition comprises pathogen-inactivated fresh frozen plasma. In some embodiments, the pathogen-inactivated plasma composition comprises pathogen-inactivated cryo-poor plasma. In some embodiments, the disease or condition is thrombocytopenic purpura (TTP) or hemolytic-uremic syndrome (HUS). In some embodiments, the plasma exchange is achieved with a volume of the plasma composition similar to the subject's plasma volume. In some embodiments, the plasma exchange is achieved with a volume of the plasma composition between about 1 times and about 1.5 times the subject's plasma volume. In some embodiments, the plasma exchange is achieved with a volume of the plasma composition comprising about 40 mL/kg patient body weight. In some embodiments, the plasma exchange is achieved with a volume of the plasma composition comprising about 60 mL/kg patient body weight. In some embodiments, the plasma exchange is performed at least two times. In some embodiments, the plasma exchange is performed 2-5 times. In some embodiments, the plasma exchange is performed 2-5 times within a period of two weeks. In some embodiments, the plasma exchange is performed 2-5 times within a period of one week.

In still another aspect, the present disclosure provides a method of treating a disease or condition indicated for treatment by infusion with intravenous immunoglobulin in a subject in need thereof, comprising administering to the subject a therapeutically effective amount of pathogen-inactivated plasma composition by plasma exchange. In some embodiments, the disease or condition is a disease or condition set forth in the present disclosure. In some embodiments, the disease or condition is Guillain-Barré syndrome, myasthenia gravis, polymyositis, dermatomyositis, or chronic inflammatory demyelinating polyneuropathy. In some embodiments, the disease or condition is other than thrombocytopenic purpura (TTP) or hemolytic-uremic syndrome (HUS). In some embodiments, the pathogen-inactivated plasma composition comprises pathogen-inactivated plasma that has not been previously frozen. In some embodiments, the pathogen-inactivated plasma composition comprises pathogen-inactivated frozen plasma. In some embodiments, the pathogen-inactivated plasma composition comprises pathogen-inactivated fresh frozen plasma. In some embodiments, the pathogen-inactivated plasma composition comprises pathogen-inactivated cryo-poor plasma. In some embodiments, the plasma exchange is achieved with a volume of the plasma composition similar to the subject's plasma volume. In some embodiments, the plasma exchange is achieved with a volume of the plasma composition between about 1 times and about 1.5 times the subject's plasma volume. In some embodiments, the plasma exchange is achieved with a volume of the plasma composition comprising about 40 mL/kg patient body weight. In some embodiments, the plasma exchange is achieved with a volume of the plasma composition comprising about 60 mL/kg patient body weight. In some embodiments, the plasma exchange is performed at least two times. In some embodiments, the plasma exchange is performed 2-5 times. In some embodiments, the plasma exchange is performed 2-5 times within a period of two weeks. In some embodiments, the plasma exchange is performed 2-5 times within a period of one week. In some embodiments, the disease or condition is thrombocytopenic purpura (TTP) or hemolytic-uremic syndrome (HUS).

In still another aspect, the present disclosure provides a method of treating a disease or condition set forth in the present disclosure. In some embodiments, the present disclosure provides a method of treating a disease or condition selected from the group consisting of Guillain-Barré syndrome, myasthenia gravis, polymyositis, dermatomyositis and chronic inflammatory demyelinating polyneuropathy in a subject, comprising administering to a subject in need thereof a therapeutically effective amount of pathogen-inactivated plasma composition by plasma exchange. In some embodiments, the pathogen-inactivated plasma composition comprises pathogen-inactivated plasma that has not been previously frozen. In some embodiments, the pathogen-inactivated plasma composition comprises pathogen-inactivated frozen plasma. In some embodiments, the pathogen-inactivated plasma composition comprises pathogen-inactivated fresh frozen plasma. In some embodiments, the pathogen-inactivated plasma composition comprises pathogen-inactivated cryo-poor plasma. In some embodiments, the plasma exchange is achieved with a volume of the plasma composition similar to the subject's plasma volume. In some embodiments, the plasma exchange is achieved with a volume of the plasma composition between about 1 times and about 1.5 times the subject's plasma volume. In some embodiments, the plasma exchange is achieved with a volume of the plasma composition comprising about 40 mL/kg patient body weight. In some embodiments, the plasma exchange is achieved with a volume of the plasma composition comprising about 60 mL/kg patient body weight. In some embodiments, the plasma exchange is performed at least two times. In some embodiments, the plasma exchange is performed 2-5 times. In some embodiments, the plasma exchange is performed 2-5 times within a period of two weeks. In some embodiments, the plasma exchange is performed 2-5 times within a period of one week.

In still another aspect, the present disclosure provides a method of treating thrombocytopenic purpura (TTP) or hemolytic-uremic syndrome (HUS) in a subject, comprising administering to a subject in need thereof a therapeutically effective amount of a pathogen-inactivated plasma composition. In some embodiments, the composition is administered by plasma exchange. In some embodiments, the pathogen-inactivated plasma composition comprises pathogen-inactivated cryo-poor plasma. In still another aspect, the present disclosure provides a method of treating thrombocytopenic purpura (TTP) or hemolytic-uremic syndrome (HUS) in a subject, comprising administering to a subject in need thereof a therapeutically effective amount of a pathogen-inactivated plasma composition by plasma exchange, wherein the pathogen-inactivated plasma composition comprises pathogen-inactivated cryo-poor plasma. In some embodiments, the pathogen-inactivated plasma composition is administered within 1 day, 2 days, 3 days, 4 days, 5 days, 6 days, or 7 days after thawing. In some embodiments, the plasma exchange is achieved with a volume of the plasma composition similar to the subject's plasma volume. In some embodiments, the plasma exchange is achieved with a volume of the plasma composition between about 1 times and about 1.5 times the subject's plasma volume. In some embodiments, the plasma exchange is achieved with a volume of the plasma composition comprising about 40 mL/kg patient body weight. In some embodiments, the plasma exchange is achieved with a volume of the plasma composition comprising about 60 mL/kg patient body weight. In some embodiments, the plasma exchange is performed at least two times. In some embodiments, the plasma exchange is performed 2-5 times. In some embodiments, the plasma exchange is performed 2-5 times within a period of two weeks. In some embodiments, the plasma exchange is performed 2-5 times within a period of one week.

In still another aspect, the present disclosure provides a method of treating a solid organ transplant recipient to prevent an immune-mediated solid organ transplant rejection, comprising administering to the transplant recipient a therapeutically effective amount of a pathogen-inactivated plasma composition by plasma exchange, wherein the plasma exchange is prior to the transplant procedure. In some embodiments, the immune-mediated transplant rejection is an antibody-mediated transplant rejection. In some embodiments, the antibody-mediated transplant rejection is an IgG-mediated transplant rejection. In some embodiments, the solid organ transplant is an ABO-incompatible solid organ transplant. In some embodiments, the solid organ transplant is an HLA-incompatible solid organ transplant. In some embodiments, the solid organ transplant is a renal (e.g., kidney) transplant. In some embodiments, the kidney is obtained from a living donor. In some embodiments, the solid organ transplant is a cardiac (e.g., heart) transplant. In some embodiments, the solid organ transplant is a liver transplant. In some embodiments, the method of treating a solid organ transplant recipient is a method of desensitization to the transplant. In some embodiments, the pathogen-inactivated plasma composition comprises pathogen-inactivated plasma that has not been previously frozen. In some embodiments, the pathogen-inactivated plasma composition comprises pathogen-inactivated frozen plasma. In some embodiments, the pathogen-inactivated plasma composition comprises pathogen-inactivated fresh frozen plasma. In some embodiments, the pathogen-inactivated plasma composition comprises pathogen-inactivated cryo-poor plasma. In some embodiments, the pathogen-inactivated plasma composition is administered within 1 day, 2 days, 3 days, 4 days, 5 days, 6 days, or 7 days after thawing. In some embodiments, the plasma exchange is achieved with a volume of the plasma composition similar to the subject's plasma volume. In some embodiments, the plasma exchange is achieved with a volume of the plasma composition between about 1 times and about 1.5 times the subject's plasma volume. In some embodiments, the plasma exchange is achieved with a volume of the plasma composition comprising about 40 mL/kg patient body weight. In some embodiments, the plasma exchange is achieved with a volume of the plasma composition comprising about 60 mL/kg patient body weight. In some embodiments, the plasma exchange is performed at least two times prior to the transplant procedure. In some embodiments, the plasma exchange is performed 2-15 times prior to the transplant procedure. In some embodiments, the method further comprises administering to the transplant recipient a therapeutically effective amount of pathogen-inactivated plasma composition by plasma exchange after the transplant procedure. In some embodiments, the plasma exchange is performed at least two times after the transplant procedure. In some embodiments, the plasma exchange is performed 2-5 times after the transplant procedure.

In some embodiments of any of the above embodiments, the pathogen-inactivated plasma composition is administered within 1 day, 2 days, 3 days, 4 days, 5 days, 6 days, or 7 days after thawing. In some embodiments of any of the above embodiments, the pathogen-inactivated plasma composition is a lyophilized or freeze-dried plasma composition. In some embodiments, the pathogen-inactivated plasma composition is administered within 1 day, 2 days, 3 days, 4 days, 5 days, 6 days, or 7 days after reconstitution.

In still another aspect, the present disclosure provides a method of fluid resuscitation in a subject suffering from burns, comprising administering to a subject in need thereof a therapeutically effective amount of a pathogen-inactivated plasma composition. In some embodiments, the subject is suffering from major burns comprising at least 20% of total body surface area. In some embodiments, the method of fluid resuscitation is a method of burn shock resuscitation. In some embodiments, endothelial permeability, endothelial dysfunction and/or vascular hyperpermeability is reduced by administration of the pathogen-inactivated plasma composition. In some embodiments, administration of the pathogen-inactivated plasma composition results in decreased subject mortality. In some embodiments, the pathogen-inactivated plasma composition comprises pathogen-inactivated frozen plasma. In some embodiments, the pathogen-inactivated plasma composition comprises pathogen-inactivated fresh frozen plasma. In some embodiments, the pathogen-inactivated plasma composition comprises pathogen-inactivated cryo-poor plasma. In some embodiments, the pathogen-inactivated plasma composition is administered within 1 day, 2 days, 3 days, 4 days, 5 days, 6 days, or 7 days after thawing. In some embodiments, the pathogen-inactivated plasma composition is a lyophilized or freeze-dried plasma composition. In some embodiments, the pathogen-inactivated plasma composition is administered within 1 day, 2 days, 3 days, 4 days, 5 days, 6 days, or 7 days after reconstitution. In some embodiments, about 1 mL to about 5 mL per kg body weight per % total burn surface area (TBSA) of the pathogen-inactivated plasma composition is administered to the subject. In some embodiments, a volume of the pathogen-inactivated plasma composition sufficient to achieve an increase in blood pressure to at least about 50 mmHg is administered to the subject. In some embodiments, a volume of the pathogen-inactivated plasma composition sufficient to achieve an increase in blood pressure to at least about 100 mmHg is administered to the subject. In some embodiments, the pathogen-inactivated plasma composition is administered to the subject within about 24 hours, within about 20 hours, within about 16 hours, within about 12 hours, within about 10 hours, within about 8 hours, within about 6 hours, within about 5 hours, within about 4 hours, within about 3 hours, within about 2 hours or within about 1 hours after the onset of burns or medical diagnosis thereof. In some embodiments, pathogen-inactivated plasma composition is administered to the subject over a time period of about 24 hours. In some embodiments, pathogen-inactivated plasma composition is administered to the subject in multiple infusions over a time period of about 24 hours.

In still another aspect, the present disclosure provides a method of treating a subject suffering from burns or a trauma, the method comprising: administering to a subject in need thereof a therapeutically effective amount of a pathogen-inactivated plasma composition. In some embodiments, the subject is suffering from burns. In some embodiments, the subject is suffering from blunt trauma. In some embodiments, the subject is suffering from penetrating trauma. In some embodiments, the subject is suffering from hemorrhage. In some embodiments, the subject is suffering from internal hemorrhage. In some embodiments, the method is a method of fluid resuscitation. In some embodiments, the method reduces hemorrhage in the subject. In some embodiments, the method reduces hemorrhagic shock in the subject. In some embodiments, endothelial permeability is reduced in the subject. In some embodiments, the method reduces or prevents trauma-induced endotheliopathy in the subject. In some embodiments, the infusion or treatment results in decreased subject mortality.

In still another aspect, the present disclosure provides a method of resuscitation from hemorrhagic shock in a subject suffering from burns or a trauma, comprising administering to the subject a therapeutically effective amount of a pathogen-inactivated plasma composition. In some embodiments, the subject is suffering from burns. In some embodiments, the subject is suffering from blunt trauma. In some embodiments, the subject is suffering from penetrating trauma. In some embodiments, the subject is suffering from internal hemorrhage. In some embodiments, the method reduces hemorrhage in the subject. In some embodiments, endothelial permeability is reduced in the subject. In some embodiments, the method reduces or prevents trauma-induced endotheliopathy in the subject. In some embodiments, the method reduces or prevents traumatic coagulopathy in the subject. In some embodiments, the treatment results in decreased subject mortality.

In some embodiments of any of the above embodiments, the pathogen-inactivated plasma composition comprises pathogen-inactivated frozen plasma. In some embodiments, the pathogen-inactivated plasma composition comprises pathogen-inactivated fresh frozen plasma. In some embodiments of any of the above embodiments, the pathogen-inactivated plasma composition comprises pathogen-inactivated cryo-poor plasma. In some embodiments of any of the above embodiments, the pathogen-inactivated plasma composition is administered within 1 day, 2 days, 3 days, 4 days, 5 days, 6 days, or 7 days after thawing. In some embodiments of any of the above embodiments, the pathogen-inactivated plasma composition is a lyophilized or freeze-dried plasma composition. In some embodiments, the pathogen-inactivated plasma composition is administered within 1 day, 2 days, 3 days, 4 days, 5 days, 6 days, or 7 days after reconstitution. In some embodiments of any of the above embodiments, the pathogen-inactivated plasma composition is first administered less than 24 hours after the onset of trauma. In some embodiments of any of the above embodiments, administration of the pathogen-inactivated plasma composition is followed by administration of at least one additional intravenous fluid.

In still another aspect, the present disclosure provides a method for preparing pathogen-inactivated cryo-poor plasma, the method comprising:

a) photochemically inactivating one or more units of plasma in the presence of a psoralen, wherein the photochemical inactivation is performed under sterile conditions in a first container containing the one or more units of plasma;

b) transferring under sterile conditions the one or more units of plasma from the first container to a compound absorption device (CAD) coupled to the first container;

c) transferring under sterile conditions the one or more units of plasma from the CAD to two or more second containers coupled to the CAD to provide pathogen-inactivated plasma;

d) transferring under sterile conditions the pathogen-inactivated plasma from the two or more second containers to a third container coupled to the two or more second containers;

e) freezing the pathogen-inactivated plasma followed by thawing of the pathogen-inactivated plasma under conditions that provide for the formation of a cryoprecipitate and pathogen-inactivated cryo-poor plasma;

f) transferring the pathogen-inactivated cryo-poor plasma to a at least a first of the two or more second containers; and g) transferring the cryoprecipitate to a second of the two or more second containers.

In some embodiments, at least a portion of the pathogen-inactivated cryo-poor plasma is transferred to each of at least two second containers in step f), and wherein the cryoprecipitate is transferred to a third second container in step g). In some embodiments, prior to step g), the cryoprecipitate is resuspended in about 80 mL to about 120 mL of pathogen-inactivated cryo-poor plasma. In some embodiments, prior to step g), the cryoprecipitate is resuspended in about 100 mL of pathogen-inactivated cryo-poor plasma.

In still another aspect, the present disclosure provides a method for infusing pathogen-inactivated cryo-poor plasma into a subject, comprising infusing into a subject in need thereof a therapeutically effective amount of a pathogen-inactivated cryo-poor plasma prepared by the method of any one of the above embodiments. In some embodiments, the subject is suffering from one or more of burns, blunt trauma, penetrating trauma, and hemorrhage. In some embodiments, the infusion results in fluid resuscitation of the subject. In some embodiments, infusing the pathogen-inactivated cryo-poor plasma into a subject is by therapeutic plasma exchange. In some embodiments, the subject in need thereof is a subject suffering from thrombocytopenic purpura (TTP) or hemolytic-uremic syndrome (HUS). In some embodiments, the method further comprises, prior to the infusion: 1) freezing the pathogen-inactivated cryo-poor plasma; and 2) thawing the pathogen-inactivated cryo-poor plasma. In some embodiments, the pathogen-inactivated cryo-poor plasma is infused into the subject within 1 day, 2 days, 3 days, 4 days, 5 days, 6 days, or 7 days after thawing.

In still another aspect, the present disclosure provides a pathogen-inactivated plasma composition according to any of the above embodiments for use in treating a disease or condition indicated for treatment by plasma exchange in a subject in need thereof. In still another aspect, the present disclosure provides a use of a pathogen-inactivated plasma composition according to any of the above embodiments in the manufacture of a medicament for treating a disease or condition indicated for treatment by plasma exchange in a subject in need thereof.

In still another aspect, the present disclosure provides a pathogen-inactivated plasma composition according to any of the above embodiments for use in treating a disease or condition indicated for treatment by infusion with intravenous immunoglobulin in a subject in need thereof. In still another aspect, the present disclosure provides a use of a pathogen-inactivated plasma composition according to any of the above embodiments in the manufacture of a medicament for treating a disease or condition indicated for treatment by infusion with intravenous immunoglobulin in a subject in need thereof.

In still another aspect, the present disclosure provides a pathogen-inactivated plasma composition according to any of the above embodiments for use in treating a disease or condition selected from the group consisting of Guillain-Barré syndrome, myasthenia gravis, polymyositis, dermatomyositis and chronic inflammatory demyelinating polyneuropathy in a subject. In still another aspect, the present disclosure provides a use of a pathogen-inactivated plasma composition according to any of the above embodiments in the manufacture of a medicament for treating a disease or condition selected from the group consisting of Guillain-Barré syndrome, myasthenia gravis, polymyositis, dermatomyositis and chronic inflammatory demyelinating polyneuropathy in a subject.

In still another aspect, the present disclosure provides a pathogen-inactivated plasma composition comprising pathogen-inactivated cryo-poor plasma according to any of the above embodiments for use in treating thrombocytopenic purpura (TTP) or hemolytic-uremic syndrome (HUS) in a subject. In still another aspect, the present disclosure provides a use of a pathogen-inactivated plasma composition comprising pathogen-inactivated cryo-poor plasma according to any of the above embodiments in the manufacture of a medicament for treating thrombocytopenic purpura (TTP) or hemolytic-uremic syndrome (HUS) in a subject.

In still another aspect, the present disclosure provides a pathogen-inactivated plasma composition according to any of the above embodiments for use in treating a solid organ transplant recipient to prevent an immune-mediated solid organ transplant rejection. In still another aspect, the present disclosure provides a use of a pathogen-inactivated plasma composition according to any of the above embodiments in the manufacture of a medicament for treating a solid organ transplant recipient to prevent an immune-mediated solid organ transplant rejection.

In still another aspect, the present disclosure provides a pathogen-inactivated plasma composition according to any of the above embodiments for use in treating a subject suffering from a trauma. In still another aspect, the present disclosure provides a use of a pathogen-inactivated plasma composition according to any of the above embodiments in the manufacture of a medicament for treating a subject suffering from a trauma. In some embodiments, the subject is suffering from burns.

In still another aspect, the present disclosure provides a pathogen-inactivated plasma composition according to any of the above embodiments for use in resuscitation from hemorrhagic shock in a subject suffering from a trauma. In still another aspect, the present disclosure provides a use of a pathogen-inactivated plasma composition according to any of the above embodiments in the manufacture of a medicament for resuscitation from hemorrhagic shock in a subject suffering from a trauma.

In still another aspect, the present disclosure provides a pathogen-inactivated plasma composition according to any of the above embodiments for use in fluid resuscitation in a subject suffering from burns. In still another aspect, the present disclosure provides a use of a pathogen-inactivated plasma composition according to any of the above embodiments in the manufacture of a medicament for fluid resuscitation in a subject suffering from burns.

In still another aspect, the present disclosure provides a pathogen-inactivated plasma composition according to any of the above embodiments for use in burn shock resuscitation in a subject. In still another aspect, the present disclosure provides a use of a pathogen-inactivated plasma composition according to any of the above embodiments in the manufacture of a medicament for burn shock resuscitation in a subject.

It is to be understood that one, some, or all of the properties of the various embodiments described herein may be combined to form other embodiments. These and other aspects will become apparent to one of skill in the art. These and other embodiments are further described by the detailed description that follows.

DETAILED DESCRIPTION

Figure 1A:
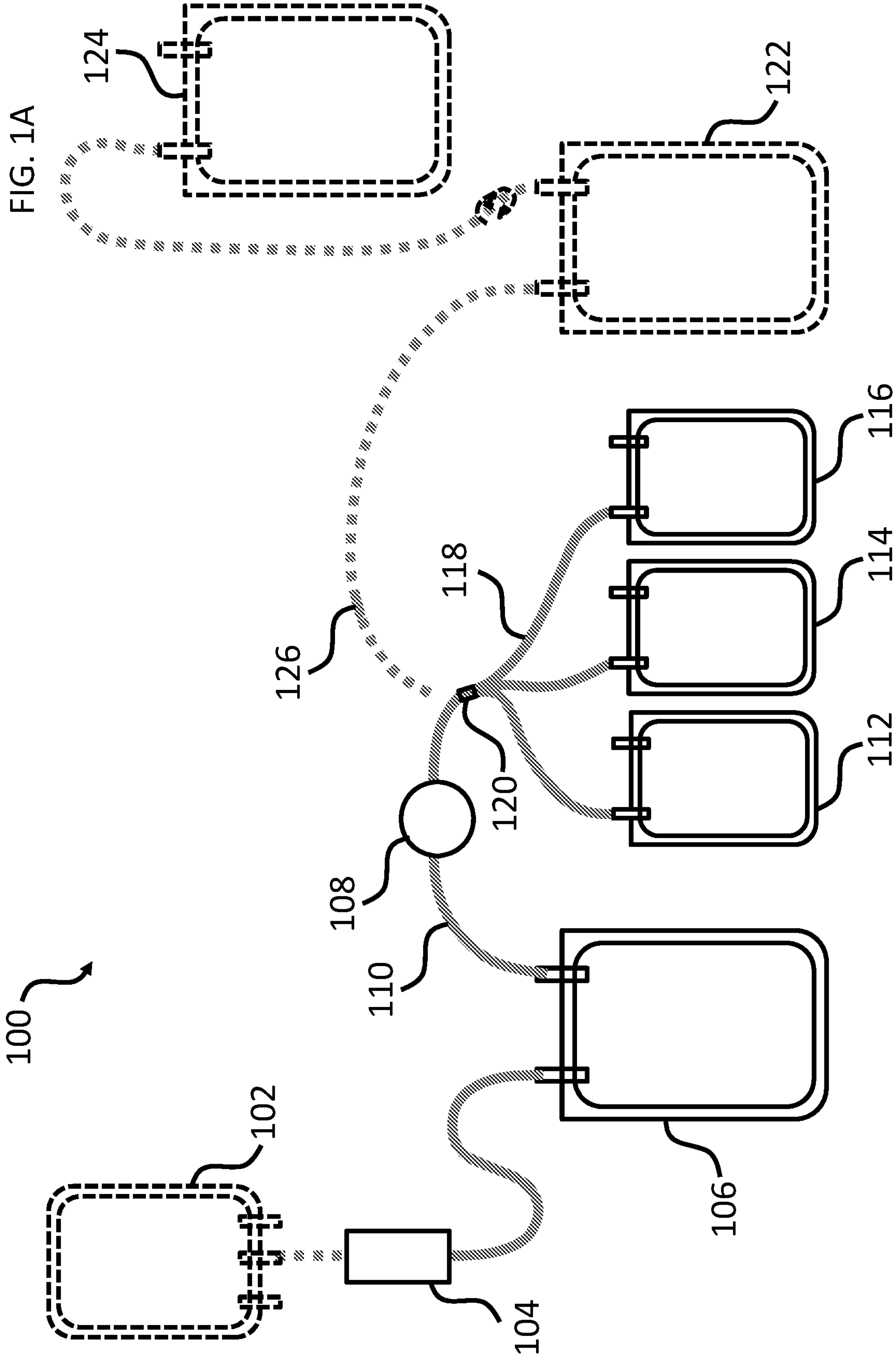
FIG. 1A shows an exemplary processing kit in accordance with some embodiments. Dotted components are optional.

The term "cryoprecipitate" refers to a blood product produced by controlled thawing of frozen plasma (e.g., whole blood-derived fresh frozen plasma, apheresis derived plasma) to form a precipitate comprising one or more coagulation factors including without limitation fibrinogen, Factor VIII, Factor XIII, vWF, and/or fibronectin. Such cryoprecipitate may be recovered from the liquid plasma portion, for example, by refrigerated centrifugation. A cryoprecipitate may be resuspended in any suitable volume of plasma after recovery. Methods for preparing a cryoprecipitate are well known in the art and provided throughout the present disclosure.

The term "plasma" refers to any plasma blood product known in the art. In some embodiments, plasma refers to whole blood-derived fresh frozen plasma. In some embodiments, plasma refers to one or more plasma units from a whole blood donation (e.g., approximately 180-250 mL volume each). In some embodiments, plasma refers to one or more plasma units from an apheresis blood donation (may be up to approximately 700-800 mL each). In some embodiments, plasma refers to a single unit. In some embodiments, plasma may be pooled from multiple units. In some embodiments, plasma may contain one or more additional components, including, without limitation, one or more pathogen-inactivation compounds and/or byproducts of a pathogen-inactivation process.

The terms "cryo-poor plasma", "cryosupernatant" and "cryo-reduced plasma" refer to the supernatant recovered after subjecting thawed frozen plasma (e.g., fresh frozen plasma, FFP) to a cryoprecipitation process, and separating the liquid supernatant from the precipitated plasma components or factors (cryoprecipitate). The cryo-poor plasma (CPP) supernatant generally contains reduced levels of various plasma components or factors (e.g., factor VIII, factor XIII, vWF, fibrinogen) that were precipitated and removed during the preparation of cryoprecipitate.

The term "suitable for infusion" refers to any blood product (e.g., a cryoprecipitate) able to be used for an infusion (e.g., a transfusion) into a subject (e.g., a human patient) according to medical judgement. In some embodiments, suitability refers to having sufficient biological activity for its intended use, i.e., for use where a transfusion of human coagulation factors is indicated, including, without limitation, control of bleeding associated with fibrinogen deficiency, treating Factor XIII deficiency, treating Factor VIII deficiency, treating von Willebrand disease, maintenance of hemostasis, treating disseminated intravascular coagulation (DIC) or high volume hemorrhage, and/or making fibrin sealant. In some embodiments, suitability refers to having sufficient safety, e.g., that the product has undergone a treatment that improves product safety (e.g., pathogen inactivation) and/or demonstrates satisfactory performance with respect to one or more safety-related measurements (such as viral or bacterial titer). Photochemical inactivation of pathogens in blood product units using amotosalen and UVA light as described herein is well established to provide such a blood product (e.g., cryoprecipitate) that is suitable for transfusion into humans. In some embodiments, suitability refers to meeting one or more standards (e.g., having a level of a biological activity or a biological component, a safety criterion, and the like) established by an accrediting agency or regulatory body that governs infusion practices, such as the AABB.

"Pathogen-inactivated" as used herein describes a blood product (e.g., a cryoprecipitate or plasma) that has undergone processing (e.g., by the methods described herein) to inactivate pathogens that may be present. It is understood that a pathogen-inactivated cryoprecipitate may include a cryoprecipitate that has itself undergone pathogen inactivation, or a cryoprecipitate made from a pathogen-inactivated blood product (e.g., plasma, whole blood, and the like). It is further understood that the process does not necessarily inactivate completely all pathogens that may be present, but substantially reduces the amount of one or more pathogens to significantly reduce the risk of a transfusion-associated disease. The inactivation of a pathogen may be assayed by measuring the number of infective pathogens (e.g., virus or bacteria) in a certain volume, and the level of inactivation is typically represented by the log reduction in the infectivity of the pathogen, or log reduction in titer. Methods of assaying log reduction in titer, and measurements thereof for pathogen inactivation are known in the art. Methods of assaying log reduction in titer, and measurements thereof for pathogen inactivation are described, for example, in U.S. Pat. No. 7,655,392, the disclosure of which is hereby incorporated by reference as it relates to assays for pathogen inactivation. As such, for any given pathogen, known amounts can be added to a test unit of cryoprecipitate or plasma to assess how much inactivation results from the process, where typically the pathogen inactivation process results in at least about 1 log reduction in titer, or about 2 log, about 3 log, about 4 log, or at least about 5 log reduction in titer. While the methods as described herein are applicable to any pathogen-inactivation treatment, it is desirable that the pathogen-inactivation treatment is capable of inactivating a variety of pathogens to at least 1 log reduction in titer, including a pathogen selected from the group consisting of HIV-1, HBV, HCV, HTLV-1, HTLV-2, West Nile virus, *Escherichia coli, Klebsiella pneumoniae, Yersinia enterocolitica, Staphylococcus epidermidis, Staphylococcus aureus, Treponema pallidum, Borrelia burgdorferi, Plasmodium falciparum, Trypanosoma cruzi*, and *Babesia microti.*

The term "pathogen inactivation compound" means any suitable compound, such as a small organic compound, that can be used to inactivate a pathogen that may be present in a blood product such as cryoprecipitate or plasma. A "photoactivated pathogen inactivation compound" is a suitable compound that requires some level of light (e.g., ultraviolet light) in order to sufficiently inactivate a pathogen. Such compounds are preferred in the inactivation of pathogens in blood products such as cryoprecipitate or plasma as they provide control over the inactivation process. Such photoactivated pathogen inactivation compounds described herein include psoralens, isoalloxazines, alloxazines, phthalocyanines, phenothiazines, and porphyrins, where these terms are understood to encompass a general class of compounds, i.e. the core compound and suitable derivatives thereof. For example, psoralens or a psoralen generally describes the psoralen core compound and any derivative thereof (e.g. amotosalen), isoalloxazines or an isoalloxazine generally describes the isoalloxazine core and any derivative thereof (e.g. riboflavin), and so forth. Such derivatives comprise the core compound structure as well as additional substituents on the core. Descriptions of such compounds include any salts thereof.

The term "amotosalen" means the compound 3-(2-aminoethoxymethyl)-2,5,9-trimethylfuro[3,2-g]chromen-7-one and any salts thereof. The compound may also be referred to as 3-[(2-aminoethoxy)methyl]-2,5,9-trimethyl-7H-furo[3,2-G][1]benzopyran-7-one-hydrochloride. The compound may also be referred to as 4'-(4-amino-2-oxa)butyl-4,5',8-trimethyl psoralen. Where the inactivation of blood products such as cryoprecipitate or plasma includes adding amotosalen HCl (the HCl salt of amotosalen) to a unit of blood product, the removal of this compound from the unit is not limited to the removal of amotosalen HCl, as the amotosalen can be present in solution as other salts or as the free base. As used in the methods described herein, removal of amotosalen means removal of the compound in any form, e.g. as the free base or as any salt, as measured by the assays described herein. Treatment or processing of blood products by amotosalen inactivation refers to combining a blood product (e.g., unit of cryoprecipitate or plasma, individual unit, pooled) with amotosalen and illuminating with a suitable dose of UVA light in order to inactivate pathogens that may be present. In some embodiments, amotosalen-inactivated cryoprecipitate has been pathogen inactivated, or the plasma from which the cryoprecipitate has been produced has been pathogen inactivated, according to commercial methods, or by similar methods.

The term "under sterile conditions" as used herein refers to maintaining the sterility of the system, for example by connection of two bags from a blood processing set, or refers to a means by which the process does not introduce contamination. For example, as used in the methods described herein, a source unit of blood product such as cryoprecipitate or plasma comprising a tubing for connection to a processing set or container of pathogen inactivation compound comprising a similar tubing may be joined under sterile condition by methods known in the art, for example using a sterile connecting device, which acts to melt or weld the tubing together to provide a sterile flow path between the two containers. Similarly, when methods described herein describe sealing off such tubing, the sealing is done under sterile conditions, for example using a tubing welder.

A "blood-collection bag" can be any bag used for collecting blood from a donor as known in the art. Blood collected in a blood-collection bag that is not attached to other bags may be centrifuged to separate the blood into blood components. Then, the blood-collection bag is sterile docked to a number of satellite bags that corresponds to the number of blood products it has been determined to manufacture from the whole blood. Blood in a blood-collection bag may be processed, such as by centrifuging and/or freezing, in the blood-collection bag before separation into satellite bags, or the blood may be transferred (by gravity or by pumping) from the blood-collection bag to a blood-processing bag.

A "blood-processing bag" is any such bag known in the art, other than the blood-collection bag, used for processing blood. The blood-processing bag may be pre-connected to the blood-collection bag or attached to the blood-collection bag through sterile docking. Blood transferred to a blood-processing bag may be centrifuged. Prior to centrifuging or immediately after centrifuging, the blood-processing bag is sterile docked to a number of satellite bags that corresponds to the number of blood products it has been determined to manufacture from the whole blood.

Blood Collection and Cryoprecipitate/Cryo-Poor Plasma Preparation

Whole blood for use in the preparation of cryoprecipitate and cryo-poor plasma as described herein may be collected by a variety of procedures known in the art. One of the most common blood collection techniques, is the "manual" collection of whole blood from healthy donors. As commonly understood and as used herein, manual collection refers to a collection method where whole blood is allowed to drain from the donor and into a collection container without the use of external pumps or similar devices. This is in contrast to so-called automated procedures where blood is withdrawn from a donor and further processed by an instrument that typically includes a processing or separation device and pumps for moving blood or blood components into and out of the device. Automated cell separation systems may be used to collect plasma from a donor by an apheresis procedure (e.g., plasmapheresis), while returning other blood components to the donor. Apheresis collected plasma also may be used for the preparation of cryoprecipitate and cryo poor plasma using the methods and kits provided herein.

In some embodiments, plasma of the present disclosure includes plasma frozen within 8 hours of donation or subjected to a pathogen inactivation process within 8 hours of donation and then frozen (e.g., fresh frozen plasma, FFP), or plasma frozen within 24 hours of donation or subjected to a pathogen inactivation process within 24 hours of donation and then frozen (e.g., PF24). In some embodiments, plasma of the present disclosure includes liquid plasma (e.g., never frozen plasma) subjected to a pathogen inactivation process and not frozen for storage and then thawed prior to the initiation of the cryoprecipitation freeze/thaw process. In some embodiments, plasma refers to one or more plasma units from a whole blood donation (e.g., approximately 180-250 mL volume each). In some embodiments, plasma refers to one or more plasma units from an apheresis blood donation (e.g., apheresis collected plasma) (may be up to approximately 700-800 mL each).

Regardless of whether the blood collection technique is manual or automated, withdrawing blood from the donor typically includes inserting a vein access device, such as a needle, into the donor's arm (and, more specifically, the donor's vein) and withdrawing blood from the donor through the needle. The "venipuncture" needle typically has attached to it, one end of a plastic tube that provides a flow path for the blood. The other end of the plastic tube terminates in one or more pre-attached plastic blood containers or bags for collecting the blood. The needle, tubing and containers make up a blood collection set which is pre-sterilized and disposed of after a single use. The sterile blood collection container typically serves as the primary container for initial separation of blood components (e.g., separation of plasma from red blood cells and platelets).

The blood collection container and plastic tubing may also include a volume of a liquid anticoagulant, while in the automated technique, a separate container of anticoagulant may be provided from which the anticoagulant is metered into the flow path and mixed with the incoming whole blood. Anticoagulant is required because of the tendency of blood to clot and adhere to the walls of the plastic surfaces which it. Exemplary anticoagulants are well known in the art and may include, but are not limited to, an anticoagulant citrate phosphate dextrose (CPD) solution, an anticoagulant citrate phosphate double dextrose (CP2D) solution, an anticoagulant citrate phosphate dextrose adenine (CPDA) solution (e.g., CPDA-1), an acid citrate dextrose (ACD) solution (e.g., ACD-A), and an anticoagulant sodium citrate 4% w/v solution.

Blood may be identified or characterized with respect to one or more parameters, such as for example, hematocrit. Such identification or characterization is typically prior to or shortly after blood collection, but prior to subjecting the collected whole blood to further processing, such as according to the methods provided herein. In addition, at or near the time of collection and prior to transfusion to a patient, tests may be performed for determining blood type and the presence of pathogens such as virus, bacteria and/or other foreign substances in the donor's blood. Such testing generally requires obtaining a sample of the donor's blood. Generally sampling of blood may be before, during or after donation, but without compromising the sterility of the system and/or the collected blood product. For example, samples may be commonly obtained by finger stick, heel stick or venipuncture. In the case where blood for hemoglobin testing is gathered with a capillary stick, a single-use sterile lancet may be used. Another well-known technique is to simply withdraw or collect the blood remaining in the flow path of the collection set after donation. This involves removing the needle from the donor, inserting the needle into a vacuum sealed sampling vial or tube and allowing the blood from the flow path to drain into the vial. Another alternative is to clamp off the flow path near the collection container and divert the blood being withdrawn from the donor to a collection (sampling) vial or tube. This procedure may employ a particular type of disposable tubing set having a pre-attached sampling site on the main flow path. Blood at or near the sampling site may be obtained by piercing the sampling site with a separately provided needle or other piercing device, and attaching a sampling vial thereto. To minimize the risk that the incoming blood will be exposed to the outside environment, the sample is typically collected after completion of the blood donation. Alternatively, some collection bags or collection sets include diversion pouches to sequester a portion (e.g., the first 20 ml) of blood collected. Another example of a blood sampling system is described in U.S. Pat. No. 5,167,656, which describes blood collection sets with an enlarged sample collection portion included in the flow path. Blood for sampling is collected in the enlarged portion by clamping off the flow path near the collection container and allowing the enlarged tubing portion to fill with blood.

Plasma useful for cryoprecipitate preparation and cryo-poor supernatant as described herein may be recovered from whole blood by a variety of procedures known in the art. For example, plasma may be recovered by centrifuging whole blood at low speed (e.g., approximately 1000-3000 rpm for approximately 10-20 minutes, optionally under refrigeration), followed by recovery of the plasma fraction. In some embodiments, the plasma may be depleted of platelets (e.g., by centrifugation at higher speeds and/or longer times within the above ranges, such as approximately 2000-3000 rpm for approximately 15-20 minutes, or approximately 5000 xg). Plasma may also be separated from whole blood by higher speed centrifugation, such as for example 5000 xg for 10 min at 4° C. Plasma collected by apheresis methods (e.g., plasmapheresis) are also well known in the art.

Methods for producing cryoprecipitate and cryo-poor plasma from plasma are well known in the art and described and exemplified herein. Typically individual units of whole blood derived plasma used for preparation of cryoprecipitate are frozen within 8 hours of donation and the frozen plasma (e.g., whole blood-derived fresh frozen plasma, FFP) may be thawed in a temperature controlled apparatus, such as a water bath. The present disclosure also contemplates that whole blood derived plasma frozen within 24 hours of donation (e.g., PF24) and plasma produced by apheresis (e.g., frozen with 8 hours, frozen within 24 hours) may be used. In certain embodiments, previously collected plasma frozen for storage (e.g., FFP, PF24), may be thawed and, if desired combined (e.g., pooled), prior to initiating a cryo-precipitation freeze/thaw process. For thawing, the temperature may be sufficiently low (e.g., at approximately 4° C., or between about 1° C. and about 6° C.) so as to result in a controlled, gradual thawing. For example, the thawing may take place over a total time of between about 4 hours and about 7-8 hours, 8-10 hours, or overnight. As discussed in greater detail supra, individual units (e.g., 200 mL units, as defined by an accepted standard such as AABB) of plasma may be used to produce a cryoprecipitate and/or cryo-poor plasma, or more than one individual unit (e.g., 200 mL units) of plasma may be pooled to produce a cryoprecipitate and/or cryo-poor plasma (e.g., 550-650 mL of plasma). For pooled plasma, a larger suitable bag such as a 1000 mL PVC bag (e.g., a Fenwal transfer pack) or any blood product compatible bag of sufficient volume (e.g., 800 mL, 600 mL) may be used to produce the cryoprecipitate and/or cryo-poor plasma. In some embodiments, the total thaw time may be dependent on the volume of plasma; e.g., a 200-250 mL unit of plasma may thaw for approximately 4.5 hours, whereas 550-650 mL of plasma may take approximately 6.5 hours. After thawing, the plasma may be centrifuged, e.g., under refrigeration (such as at approximately 4° C.) for approximately 10-15 minutes at approximately 4200 rcf (optionally with a slow stop) to separate the cryoprecipitate from the cryo-poor plasma (cryosupernatant). The cryoprecipitate may be separated from the cryo-poor plasma, e.g., by inversion to remove the cryo-poor plasma, or through use of a plasma expressor to remove the cryo-poor plasma, with the cryo-poor plasma collected by transfer into one or more separate containers In some embodiments, cryoprecipitate and/or cryo-poor plasma may be frozen after production. As the cryoprecipitate may be derived from plasma that has itself been frozen, "re-freezing" the cryoprecipitate as used herein refers to freezing a cryoprecipitate after producing the cryoprecipitate (e.g., after the initial plasma freezing step, after the precipitation step). Advantageously, this allows the cryoprecipitate to be stored for later use. In some embodiments, cryoprecipitate may be stored at about −18° C. or lower (e.g., according to AABB standards).

After freezing (and optional frozen storage), cryoprecipitate and/or cryo-poor plasma may be thawed. Methods for thawing frozen cryoprecipitate and/or cryo-poor plasma are well known in the art. As a non-limiting example, cryoprecipitate and/or cryo-poor plasma may be thawed in a plasma thawer (e.g., those commercially available from Helmer Scientific). In some embodiments, cryoprecipitate and/or cryo-poor plasma may be thawed at about 35° C. In some embodiments, cryoprecipitate and/or cryo-poor plasma may be thawed for approximately 5-10 minutes. In some embodiments, after thawing, the cryoprecipitate may be mixed, e.g., by agitation. In some embodiments, cryoprecipitate may be allowed to thaw for two or more intervals, which may optionally be separated by one or more mixing steps. In some embodiments, cryoprecipitate may be thawed for approximately 5-10 minutes, mixed, and allowed to continue thawing for approximately 5-10 minutes.

In some embodiments, cryoprecipitate and/or cryo-poor plasma may be lyophilized or freeze-dried. Freeze-dried and lyophilized blood product compositions are known in the art. For example, freeze-dried plasma (FDP) and lyophilized plasma have been used in patients suffering from traumatic injury (see, e.g., Inaba, K. (2011) *J. Trauma* 70:S57-8 and Sailliol, A. et al. (2013) *Transfusion* 53 Suppl 1:65S-71S).

For each of the parameters set forth in the methods provided herein, techniques for determination or measurement of the parameters are well known in the art.

Cryoprecipitate and Cryo-Poor Plasma Compositions

Described infra are various exemplary parameters and properties that may characterize a cryoprecipitate (or a composition comprising a cryoprecipitate) and/or cryo-poor plasma of the present disclosure. It will be appreciated by one of skill in the art that these exemplary characteristics and embodiments may be combined in any number or combination, unless otherwise indicated by context. These exemplary characteristics and embodiments may be combined with any of the other embodiments or aspects described elsewhere herein in any number or combination, unless otherwise indicated by context.

Certain aspects of the present disclosure relate to compositions comprising a cryoprecipitate suitable for infusion into a subject. As disclosed herein, these compositions are suitable for infusion into a subject for a longer duration after thawing (e.g., thawing after frozen cryoprecipitate storage) than is currently prescribed by existing guidelines (e.g., the compositions have an extended period before expiry after thawing). Such compositions may find use, inter alia, in treatments (e.g., infusions) related to control of bleeding associated with fibrinogen deficiency, treating Factor XIII deficiency, treating von Willebrand disease, maintenance of hemostasis, treating disseminated intravascular coagulation (DIC) or high volume hemorrhage, and/or making fibrin sealant.

Certain aspects of the present disclosure relate to compositions comprising a cryo-poor plasma suitable for infusion into a subject. Such compositions may find use, inter alia, in improved treatment methods using such compositions for therapeutic plasma exchange or infusion for indications, such as, but not limited to trauma and/or burns.

In some embodiments, a cryoprecipitate (or a composition comprising a cryoprecipitate) or cryo-poor plasma is suitable for infusion into a subject at least 6 hours, at least 12 hours, at least 24 hours, at least 36 hours, at least 48 hours, at least 60 hours, at least 72 hours, at least 84 hours, at least 96 hours, at least 108 hours, at least 120 hours, at least 132 hours, at least 144 hours, at least 156 hours, or at least 168 hours after thawing. In some embodiments, a cryoprecipitate or cryo-poor plasma is suitable for infusion into a subject within 6 hours, within 12 hours, within 24 hours, within 36 hours, within 48 hours, within 60 hours, within 72 hours, within 84 hours, within 96 hours, within 108 hours, within 120 hours, within 132 hours, within 144 hours, within 156 hours, or within 168 hours after thawing. In some embodiments, the cryoprecipitate or cryo-poor plasma is suitable for infusion into a subject for a number of hours after thawing that is less than about any of the following numbers of hours: 168, 156, 144, 132, 120, 108, 96, 84, 72, 60, 48, 36, 24, or 12. In some embodiments, the cryoprecipitate is or cryo-poor plasma suitable for infusion into a subject for a number of hours after thawing (e.g., after thawing and resuspension of the cryoprecipitate) that is greater than about any of the following numbers of hours: 0, 0.25, 0.5, 1, 2, 3, 4, 5, 6, 12, 24, 36, 48, 60, 72, 84, 96, 108, 120, 132, 144, or 156. That is, the number of hours after thawing for which the cryoprecipitate or cryo-poor plasma is suitable for infusion into a subject may be any number of hours within a range having an upper limit of 168, 156, 144, 132, 120, 108, 96, 84, 72, 60, 48, 36, 24, or 12 hours and an independently selected lower limit of 0, 0.25, 0.5, 1, 2, 3, 4, 5, 6, 12, 24, 36, 48, 60, 72, 84, 96, 108, 120, 132, 144, or 156 hours, wherein the upper limit is greater than the lower limit. In some embodiments, the cryoprecipitate is suitable for infusion into a subject immediately after thawing and resuspension of the cryoprecipitate (e.g., 0 hours after thawing). In some embodiments, the cryoprecipitate or cryo-poor plasma may be suitable for infusion into a subject for about 0 to about 168 hours, about 0 to about 144 hours, about 0 to about 120 hours after thawing, about 0 to about 96 hours after thawing, about 0 to about 72 hours after thawing, or about 0 to about 48 hours after thawing. In some embodiments, the cryoprecipitate may be suitable for infusion into a subject for about 6 to about 168 hours, about 6 to about 144 hours, or about 6 to about 120 hours after thawing. In some embodiments, the cryoprecipitate may be suitable for infusion into a subject for about 12 to about 168 hours, about 12 to about 144 hours, or about 12 to about 120 hours after thawing. In some embodiments, the cryoprecipitate may be suitable for infusion into a subject for about 24 to about 168 hours, about 24 to about 144 hours, or about 24 to about 120 hours after thawing. In some embodiments, the cryoprecipitate may be suitable for infusion into a subject for about 36 to about 168 hours, about 36 to about 144 hours, or about 36 to about 120 hours after thawing. In some embodiments, the cryoprecipitate may be suitable for infusion into a subject for about 48 to about 168 hours, about 48 to about 144 hours, or about 48 to about 120 hours after thawing.

In some embodiments, a cryoprecipitate (or a composition comprising a cryoprecipitate) or cryo-poor plasma is suitable for infusion into a subject at least 1 day, at least 2 days, at least 3 days, at least 4 days, at least 5 days, at least 6 days, or at least 7 days after thawing. In some embodiments, the cryoprecipitate or cryo-poor plasma is suitable for infusion into a subject within 1 day, within 2 days, within 3 days, within 4 days, within 5 days, within 6 days, or within 7 days after thawing. In some embodiments, a cryoprecipitate or cryo-poor plasma is suitable for infusion into a subject for a number of days after thawing that is less than about any of the following numbers of days: 7, 6, 5, 4, 3, or 2. In some embodiments, the cryoprecipitate or cryo-poor plasma is suitable for infusion into a subject for a number of days after thawing (e.g., after thawing and resuspension of the cryoprecipitate) that is greater than about any of the following numbers of days: 0, 1, 2, 3, 4, 5, or 6. In some embodiments, the cryoprecipitate or cryo-poor plasma is suitable for infusion into a subject immediately after thawing and resuspension of the cryoprecipitate (e.g., 0 days after thawing). That is, the number of days after thawing for which the cryoprecipitate or cryo-poor plasma is suitable for infusion into a subject may be any number of days within a range having an upper limit of 7, 6, 5, 4, 3, or 2 days and an independently selected lower limit of 0, 1, 2, 3, 4, 5, or 6 days, wherein the upper limit is greater than the lower limit. In some embodiments, the cryoprecipitate or cryo-poor plasma may be suitable for infusion into a subject for about 0 to about 7 days, about 0 to about 6 days, about 0 to about 5 days, about 0 to about 4 days, about 0 to about 3 days, or about 0 to about 2 days after thawing. In some embodiments, the cryoprecipitate or cryo-poor plasma may be suitable for infusion into a subject for about 1 to about 7 days, about 1 to about 6 days, or about 1 to about 5 days after thawing. In some embodiments, the cryoprecipitate or cryo-poor plasma may be suitable for infusion into a subject for about 2 to about 7 days, about 2 to about 6 days, or about 2 to about 5 days after thawing.

In some embodiments, a cryoprecipitate (or a composition comprising a cryoprecipitate) or cryo-poor plasma is stored at room temperature after thawing, e.g., for the interval between thawing and use (e.g., in an infusion). In some embodiments, a cryoprecipitate (or a composition comprising a cryoprecipitate) or cryo-poor plasma is stored at between about 2° C. and about 25° C. after thawing, e.g., for the interval between thawing and use (e.g., in an infusion). In some embodiments, a cryoprecipitate (or a composition comprising a cryoprecipitate) or cryo-poor plasma is stored at between about 20° C. and about 24° C. after thawing, e.g., for the interval between thawing and use (e.g., in an infusion). In some embodiments, a cryoprecipitate (or a composition comprising a cryoprecipitate) or cryo-poor plasma is stored at about 22° C. after thawing, e.g., for the interval between thawing and use. In some embodiments, a cryoprecipitate (or a composition comprising a cryoprecipitate) or cryo-poor plasma is stored at 2° C. and about 6° C. after thawing, e.g., for the interval between thawing and use (e.g., in an infusion). In some embodiments, a cryoprecipitate (or a composition comprising a cryoprecipitate) or cryo-poor plasma is stored after thawing, e.g., for the interval between thawing and use (e.g., in an infusion) according to standards set by AABB, the American Red Cross or another accrediting, regulatory, or standard-setting agency.

It is well known in the art that different types of blood donations containing plasma may have different associated volumes. The volume of plasma obtained from a whole blood donation may vary, depending upon, for example, the volume of whole blood collected, the size of the collection bag (e.g., 450 mL, 500 mL), the donor percent hematocrit and processing conditions (e.g., centrifugation conditions). For example, in certain embodiments, a whole blood donation typically yields an approximately 180-250 mL (e.g., approximately 200 mL) unit of plasma (e.g., whole blood derived plasma), whereas the volume of plasma from a single apheresis donation or sample (e.g., apheresis collected plasma) may yield from about 200 mL up to approximately 700-800 mL, depending on a variety of factors including donor size (e.g., body weight). In some embodiments, a cryoprecipitate (or a composition comprising a cryoprecipitate) and/or cryo-poor plasma of the present disclosure may be obtained or prepared from about 180 mL or 200 mL to about 250 mL or 300 mL or 325 mL of plasma. For example, the cryoprecipitate and/or cryo-poor plasma may be obtained from one approximately 200 mL unit (e.g., AABB defined unit, AABB unit volume) volume of plasma, such as from a single whole blood donation. In other embodiments, a cryoprecipitate (or a composition comprising a cryoprecipitate) and/or cryo-poor plasma of the present disclosure may be obtained from at least about 300 mL, at least about 400 mL, at least about 500 mL, or at least about 600 mL or more of plasma. In other embodiments, a cryoprecipitate (or a composition comprising a cryoprecipitate) and/or cryo-poor plasma of the present disclosure may be obtained from at least about 300 mL, at least about 400 mL, at least about 500 mL, or at least about 600 mL or more of plasma. In other embodiments, a cryoprecipitate (or a composition comprising a cryoprecipitate) of the present disclosure may be obtained from at least about 550 mL and less than 650 mL of plasma. In some embodiments, a cryoprecipitate (or a composition comprising a cryoprecipitate) and/or cryo-poor plasma of the present disclosure may be obtained from at least about 570 mL and less than about 620 mL of plasma. In some embodiments, a cryoprecipitate (or a composition comprising a cryoprecipitate) and/or cryo-poor plasma of the present disclosure may be obtained from at least about 600 mL and less than about 650 mL of plasma. In certain embodiments, a cryoprecipitate (or a composition comprising a cryoprecipitate) and/or cryo-poor plasma of the present disclosure may be obtained from about 600 mL of plasma. For example, a cryoprecipitate and/or cryo-poor plasma may be obtained from pooling multiple AABB unit volumes of plasma (e.g., to yield 550-650 mL), a single apheresis sample (e.g., having 550-650 mL or more), or from pooling multiple cryoprecipitates or cryo-poor plasmas obtained from different samples of plasma.

As such, in some embodiments, a cryoprecipitate (or a composition comprising a cryoprecipitate) and/or cryo-poor plasma of the present disclosure may contain cryoprecipitate and cryo-poor plasma, respectively, obtained or prepared from one donor. In other embodiments, a cryoprecipitate (or a composition comprising a cryoprecipitate) of the present disclosure and/or cryo-poor plasma may contain cryoprecipitate and/or cryo-poor plasma, respectively, obtained or prepared from more than one donor (e.g., prepared from more than one plasma donation, prepared from more than one plasma unit). In some embodiments, a cryoprecipitate (or a composition comprising a cryoprecipitate) and/or cryo-poor plasma of the present disclosure may contain cryoprecipitate and/or cryo-poor plasma, respectively, obtained or prepared from 2-12 donors. In some embodiments, a cryoprecipitate (or a composition comprising a cryoprecipitate) and/or cryo-poor plasma of the present disclosure may contain cryoprecipitate and/or cryo-poor plasma, respectively, prepared from plasma obtained from 2-6 donors. For example, in some embodiments, a cryoprecipitate (or a composition comprising a cryoprecipitate) and/or cryo-poor plasma of the present disclosure may contain cryoprecipitate and/or cryo-poor plasma, respectively, prepared from plasma obtained from 1, 2, 3, 4, 5, or 6 donors. In some embodiments, a cryoprecipitate (or a composition comprising a cryoprecipitate) and/or cryo-poor plasma of the present disclosure may contain cryoprecipitate and/or cryo-poor plasma, respectively, obtained or prepared from 7-12 donors. For example, in some embodiments, a cryoprecipitate (or a composition comprising a cryoprecipitate) and/or cryo-poor plasma of the present disclosure may contain cryoprecipitate and/or cryo-poor plasma, respectively, prepared from plasma obtained from 7, 8, 9, 10, 11 or 12 donors.

In some embodiments, a cryoprecipitate composition and/or cryo-poor plasma of the present disclosure may contain more than one cryoprecipitate (e.g., individual cryoprecipitate preparations) and/or cryo-poor plasma, respectively. For example, in some embodiments, a cryoprecipitate composition and/or cryo-poor plasma of the present disclosure may contain a first cryoprecipitate and/or cryo-poor plasma, respectively, obtained from pathogen-inactivated plasma and a second cryoprecipitate and/or cryo-poor plasma, respectively, obtained from pathogen-inactivated plasma. In some embodiments, a cryoprecipitate composition and/or cryo-poor plasma of the present disclosure may contain a first cryoprecipitate and/or cryo-poor plasma, respectively, obtained from 2 units of pathogen-inactivated plasma and a second cryoprecipitate and/or cryo-poor plasma, respectively, obtained from 2 units of pathogen-inactivated plasma. In some embodiments, a cryoprecipitate composition and/or cryo-poor plasma of the present disclosure may contain a first cryoprecipitate and/or cryo-poor plasma, respectively, obtained from 3 units of pathogen-inactivated plasma and a second cryoprecipitate and/or cryo-poor plasma, respectively, obtained from 3 units of pathogen-inactivated plasma. In some embodiments, the first and the second cryoprecipitates and/or cryo-poor plasma are combined prior to re-freezing for storage. In some embodiments, the first and the second cryoprecipitates and/or cryo-poor plasma are combined prior to use (e.g., in an infusion), and/or prior to storage at room temperature or under refrigeration. In some embodiments, a cryoprecipitate composition and/or cryo-poor plasma of the present disclosure may contain pathogen-inactivated plasma pooled from at least 3, at least 4, at least 5, or at least 6 units of pathogen-inactivated plasma. In some embodiments, a cryoprecipitate composition and/or cryo-poor plasma of the present disclosure may contain pathogen-inactivated plasma pooled from at least 7, at least 8, at least 9, at least 10, at least 11, or at least 12 units of pathogen-inactivated plasma. In some embodiments, a cryoprecipitate composition and/or cryo-poor plasma of the present disclosure may contain pathogen-inactivated plasma pooled from at least 7, at least 8, at least 9, at least 10, at least 11, or at least 12 units of pathogen-inactivated plasma. In certain embodiments, a cryoprecipitate composition and/or cryo-poor plasma of the present disclosure may contain pathogen-inactivated plasma pooled from at least 3 units of pathogen-inactivated plasma. In certain embodiments, a cryoprecipitate composition and/or cryo-poor plasma of the present disclosure may contain pathogen-inactivated plasma pooled from at least 6 units of pathogen-inactivated plasma.

In some embodiments, a cryoprecipitate composition of the present disclosure may be generated from plasma that has not been subject to pathogen inactivation, then the cryoprecipitate itself may be subjected to pathogen-inactivation (and, optionally, frozen for storage after pathogen inactivation). In some embodiments, the pathogen inactivated cryoprecipitate may be stored at 2-25° C. (e.g., 2-6° C., 20-24° C.) until use for infusion. In some embodiments, a cryoprecipitate may be prepared from plasma and subsequently subjected to pathogen inactivation. In some embodiments, the plasma has not been subject to pathogen inactivation. In some embodiments, multiple cryoprecipitate preparations made from plasma (e.g., plasma that has not been subject to pathogen inactivation) may be pooled together, then subject to pathogen inactivation. Advantageously, this enables the pathogen inactivation of a large volume of cryoprecipitate (e.g., a pooled cryoprecipitate composition) in one step and/or one container. In other embodiments, multiple cryoprecipitate preparations prepared from plasma (e.g., plasma that has not been subject to pathogen inactivation) may be subject to pathogen inactivation, then pooled together. In some embodiments, the pathogen-inactivated cryoprecipitate (e.g., pooled cryoprecipitate) is frozen for storage. Any desired volume of cryoprecipitate may be subject to pathogen inactivation and optionally pooled (e.g., before or after pathogen inactivation). For example, in some embodiments, at least two, at least three, at least four, at least five, at least six, at least seven, at least eight, at least nine, at least 10, at least 11, or at least 12 preparations or units of cryoprecipitate may be pooled together, e.g., before or after pathogen inactivation. In some embodiments, the cryoprecipitate is prepared from at least about 550 mL and less than about 650 mL of plasma. In some embodiments, the cryoprecipitate is prepared by pooling two or more cryoprecipitate units (e.g., before or after pathogen inactivation), each cryoprecipitate unit having been prepared from at least about 550 mL and less than about 650 mL of plasma. In some embodiments, the cryoprecipitate is prepared by pooling two or more, three or more, four or more, five or more, six or more, seven or more, eight or more, nine or more, ten or more, eleven or more, or twelve or more cryoprecipitate units (e.g., before or after pathogen inactivation), each cryoprecipitate unit having been prepared from at least about 150 mL and less than about 250 mL of plasma, e.g., about 200 mL of plasma. In some embodiments, the cryoprecipitate is prepared by pooling two or more, three or more, four or more, five or more, six or more, seven or more, eight or more, nine or more, ten or more, eleven or more, or twelve or more cryoprecipitate units (e.g., before or after pathogen inactivation), each cryoprecipitate unit having been prepared from a whole blood derived plasma unit.

In some embodiments, a cryoprecipitate composition of the present disclosure may contain a first cryoprecipitate obtained or prepared from at least about 550 mL and less than 650 mL of pathogen-inactivated plasma, and a second cryoprecipitate obtained or prepared from at least about 550 mL and less than 650 mL of pathogen-inactivated plasma. In some embodiments, a cryoprecipitate composition of the present disclosure may contain a first cryoprecipitate obtained or prepared from at least about 570 mL and less than 620 mL of pathogen-inactivated plasma, and a second cryoprecipitate obtained or prepared from at least about 570 mL and less than 620 mL of pathogen-inactivated plasma. In some embodiments, a cryoprecipitate composition of the present disclosure may contain a first cryoprecipitate obtained or prepared from at least about 600 mL and less than 650 mL of pathogen-inactivated plasma, and a second cryoprecipitate obtained or prepared from at least about 600 mL and less than 650 mL of pathogen-inactivated plasma. In certain embodiments, a cryoprecipitate composition of the present disclosure may contain a first cryoprecipitate obtained or prepared from about 600 mL of pathogen-inactivated plasma, and a second cryoprecipitate obtained or prepared from about 600 mL of pathogen-inactivated plasma. In some embodiments, a cryoprecipitate composition of the present disclosure may contain a first cryoprecipitate obtained or prepared from at least about 150 mL and less than about 250 mL of pathogen-inactivated plasma, and a second cryoprecipitate obtained or prepared from at least about 150 mL and less than about 250 mL of pathogen-inactivated plasma. Individual cryoprecipitates may be combined or pooled after cryoprecipitate production but prior to use and/or re-freezing for storage, and/or individual plasma samples may be combined or pooled prior to cryoprecipitate production.

In some embodiments, a cryoprecipitate may be part of a composition containing plasma at a specific volume. For example, cryoprecipitate is typically resuspended in a volume of plasma remaining after cryoprecipitate production (e.g., some amount of leftover plasma after production of the cryoprecipitate). This volume may then be used or frozen for storage as described herein.

In some embodiments, a composition comprising a cryoprecipitate of the present disclosure includes plasma (e.g., cryo-poor plasma) of a volume that is less than about any of the following volumes (in mL): 150, 140, 130, 120, 110, 100, 90, 80, 76, 75, 74, 73, 72, 71, 70, 69, 68, 67, 66, 65, 64, 63, 62, 61, 60, 59, 58, 57, 56, 55, 54, 53, 52, 51, 50, 45, 40, 35, 30, 25, 20, 19, 18, 17, 16, 15, 14, 13, 12, 11, 10, 9, 8, 7, or 6. In some embodiments, a composition comprising a cryoprecipitate of the present disclosure includes plasma of a volume that is greater than about any of the following volumes (in mL): 5, 6, 7, 8, 9, 10, 11, 12, 13, 14, 15, 16, 17, 18, 19, 20, 25, 30, 35, 40, 45, 50, 51, 52, 53, 54, 55, 56, 57, 58, 59, or 60. That is, the composition comprising a cryoprecipitate of the present disclosure may include plasma of any volume within a range having an upper limit of 150, 140, 130, 120, 110, 100, 90, 80, 76, 75, 74, 73, 72, 71, 70, 69, 68, 67, 66, 65, 64, 63, 62, 61, 60, 59, 58, 57, 56, 55, 54, 53, 52, 51, 50, 45, 40, 35, 30, 25, 20, 19, 18, 17, 16, 15, 14, 13, 12, 11, 10, 9, 8, 7, or 6 mL and an independently selected lower limit of 5, 6, 7, 8, 9, 10, 11, 12, 13, 14, 15, 16, 17, 18, 19, 20, 25, 30, 35, 40, 45, 50, 51, 52, 53, 54, 55, 56, 57, 58, 59, or 60 mL, wherein the upper limit is greater than the lower limit. In some embodiments, a composition comprising a cryoprecipitate of the present disclosure includes between about 5 mL and about 25 mL of plasma, about 5 mL and about 20 mL of plasma, about 10 mL to about 20 mL of plasma, or about 15 mL to about 20 mL of plasma. In other embodiments, a composition comprising a cryoprecipitate of the present disclosure includes between about 30 mL and about 150 mL, between about 75 mL and about 150 mL, between about 30 mL and about 75 mL of plasma, between about 40 mL and about 75 mL of plasma, between about 50 mL and about 75 mL of plasma, between about 60 mL and about 75 mL of plasma, between about 50 mL and about 70 mL of plasma, between about 50 mL and about 65 mL of plasma, between about 50 mL and about 60 mL of plasma, between about 55 mL to about 70 mL of plasma, between about 55 mL to about 65 mL of plasma, between about 55 mL to about 60 mL of plasma, or between about 60 mL and about 70 mL of plasma. In other embodiments, a composition comprising a cryoprecipitate of the present disclosure includes greater than about 1 mL and less than or equal to about 75 mL of plasma, or greater than about 5 mL and less than or equal to about 75 mL of plasma. In some embodiments, a composition comprising a cryoprecipitate of the present disclosure includes about 10 mL, about 20 mL, about 30 mL, about 40 mL, about 50 mL, about 60 mL, about 70 mL, about 80 mL, about 90 mL, about 100 mL, about 110 mL, about 120 mL or about 130 mL of plasma. In some embodiments, the aforementioned plasma volumes comprise the plasma volumes following resuspension of the cryoprecipitate.

In some embodiments, the specific volume of plasma may depend upon the amount of cryoprecipitate (e.g., depend upon the amount of plasma used to produce the cryoprecipitate). In some embodiments, for cryoprecipitate obtained from one AABB unit volume of plasma (e.g., 200 mL), the volume of plasma in the composition may be from about 5 mL to about 25 mL, from about 5 mL to about 20 mL, from about 10 mL to about 20 mL or from about 15 mL to about 20 mL, or any other comparable range as described above. In some embodiments, for cryoprecipitate obtained from more than one AABB unit volume of plasma (e.g., 550-650 mL), or for a pool of multiple cryoprecipitate preparations (e.g., each having been obtained from about 200 mL of plasma), the volume of plasma in the composition may be from about 15 mL to about 75 mL, from about 15 mL to about 60 mL, from about 30 mL to about 75 mL, from about 30 mL to about 60 mL, from about 30 mL to about 40 mL, 40 mL to about 70 mL, from about 45 mL to about 65 mL, from about 50 mL to about 60 mL, or any other comparable range as described above. In certain embodiments, the volume of plasma in the composition may be less than or equal to about 75 mL. In some embodiments, for cryoprecipitate obtained by combining two or more cryoprecipitate preparations, each made from more than one AABB unit volume of plasma (e.g., each being 550-650 mL, for an aggregate total of 1100-1300 mL), the volume of plasma in the composition may be from about 30 mL to about 150 mL, from about 30 mL to about 120 mL, from about 60 mL to about 120 mL, from about 90 mL to about 120 mL, from about 50 mL to about 100 mL, from about 60 mL to about 90 mL, from about 60 mL to about 75 mL from about 50 mL to about 75 mL, or about 75 mL. In certain embodiments, the volume of plasma in the composition obtained by combining two or more cryoprecipitate preparations may be less than or equal to about 75 mL.

As described herein and well known in the art, a cryoprecipitate or cryoprecipitate composition or cryo-poor plasma of the present disclosure may be tested for the amount and/or activity of one or more components, including without limitation fibrinogen, Factor VIII, Factor XIII, and/or vWF. In some embodiments, this testing refers to a measurement taken from an individual sample. In other embodiments, it refers to an average based on measurements taken from multiple samples (e.g., random samples of sufficient number to provide a statistically significant sampling). Often, multiple cryoprecipitate compositions (units) may be thawed during a particular period of production (e.g., 1 month of production) and tested to yield a measurement that is held to be representative of those units that were not tested. Similarly, multiple cryo-poor plasma compositions (units) may be thawed during a particular period of production (e.g., 1 month of production) and tested to yield a measurement that is held to be representative of those units that were not tested. The un-tested or non-tested samples may then be used in a treatment, such as an infusion. Therefore, "testing" as used herein refers to testing a particular cryoprecipitate and/or cryo-poor plasma composition, or it refers to testing other cryoprecipitate and/or cryo-poor plasma compositions in a defined cross-section of cryoprecipitate and/or cryo-poor plasma compositions (e.g., in which a measurement of one or more individual samples or average of measurements is held to be representative of a cryoprecipitate and/or cryo-poor plasma composition that was not tested). In some embodiments, a cryoprecipitate or cryoprecipitate composition or cryo-poor plasma of the present disclosure may be tested prior to re-freezing and/or storage. In some embodiments, a cryoprecipitate or cryoprecipitate composition or cryo-poor plasma of the present disclosure may be tested after thawing. In some embodiments, a cryoprecipitate or cryoprecipitate composition or cryo-poor plasma of the present disclosure may be tested before use, e.g., in an infusion. As used herein, the terms "testing" and "determining," including grammatical derivatives thereof, may be used interchangeably. Therefore, "determining" as used herein refers to determining an amount of an analyte of interest (including without limitation fibrinogen, Factor VIII, Factor XIII, and/or vWF) in a particular cryoprecipitate and/or cryo-poor plasma composition, or it refers to determining an amount of the analyte of interest in other cryoprecipitate and/or cryo-poor plasma compositions in a defined cross-section of cryoprecipitate and/or cryo-poor plasma compositions (e.g., in which a measurement of one or more individual samples or average of measurements is held to be representative of a cryoprecipitate and/or cryo-poor plasma composition that was not tested, such as a plurality of cryoprecipitate and/or cryo-poor plasma compositions produced by the same methods and/or produced in the same location or general time frame, e.g., within 30 days).

It will be appreciated by one of skill in the art that a cryoprecipitate or cryoprecipitate composition or cryo-poor plasma of the present disclosure may be tested at one or more times (e.g., after thawing) for the amount and/or activity of one or more components, including without limitation fibrinogen, Factor VIII, Factor XIII, and/or vWF. For example, a cryoprecipitate or cryoprecipitate composition or cryo-poor plasma of the present disclosure may be tested shortly after thawing (e.g., within 2 hours of thawing, within 6 hours of thawing), and/or a cryoprecipitate or cryoprecipitate composition or cryo-poor plasma of the present disclosure may be tested at or shortly preceding the time of infusion or the time of expiry post-thaw, which, in some embodiments described herein, may occur up to about 1 day, up to about 2 days, up to about 3 days, up to about 4 days, up to about 5 days, or up to about 7 days after thawing. It is to be understood that any of the exemplary amounts of cryoprecipitate or cryoprecipitate composition or cryo-poor plasma components described herein (e.g., fibrinogen, Factor VIII, Factor XIII, and/or vWF) refers to an amount tested or determined shortly after thawing (e.g., within 2 hours of thawing, within 6 hours of thawing) or an amount tested at or shortly preceding the time of infusion or the time of expiry post-thaw (e.g., up to about 1 day, up to about 2 days, up to about 3 days, up to about 4 days, up to about 5 days, or up to about 7 days after thawing).

In some embodiments, a cryoprecipitate or cryoprecipitate composition or cryo-poor plasma of the present disclosure may be tested for Factor VIII. Various assays for measuring Factor VIII are known in the art, including without limitation the chromogenic assay, the one-stage clotting or activated partial thromboplastin time (APTT) assay, and the two-stage clotting or activated partial thromboplastin time (APTT) assay. Without wishing to be bound to theory, it is thought that cryoprecipitate having less than a particular amount of Factor VIII, e.g., an AABB standard for Factor VIII such as 80 IU per unit, may advantageously be used for the treatment of many conditions, including without limitation control of bleeding associated with fibrinogen deficiency, treating Factor XIII deficiency, treating von Willebrand disease, maintenance of hemostasis, treating disseminated intravascular coagulation (DIC) or high volume hemorrhage, and/or making fibrin sealant. Advantageously, this cryoprecipitate, preferably containing pathogen inactivated plasma, may be suitable for infusion after a greater duration post-thawing than, e.g., recommended by current AABB standards (such as less than 6 hours).

In some embodiments, a cryoprecipitate or cryoprecipitate composition or cryo-poor plasma of the present disclosure contains less than about 80, less than about 75, less than about 70, less than about 65, less than about 60, less than about 55, less than about 50, less than about 45, less than about 40, less than about 35, less than about 30, less than about 25, less than about 20, less than about 15, or less than about 10 IU of Factor VIII per unit of cryoprecipitate (e.g., per unit of cryoprecipitate derived from about 200 mL of plasma) or cryo-poor plasma. In some embodiments, a composition comprising a cryoprecipitate or cryo-poor plasma of the present disclosure includes Factor VIII at an amount that is less than about any of the following amounts (in IU, either absolute or per unit of cryoprecipitate): 480, 450, 400, 350, 300, 250, 225, 200, 175, 150, 125, 100, 95, 90, 85, 80, 75, 70, 65, 60, 55, 50, 45, 40, 35, 30, 25, 20, or 15. In some embodiments, a composition comprising a cryoprecipitate or cryo-poor plasma of the present disclosure includes Factor VIII at an amount that is greater than about any of the following amounts (in IU, either absolute or per unit of cryoprecipitate): 10, 15, 20, 25, 30, 35, 40, 45, 50, 55, 60, 65, 70, 75, 80, 85, 90, 95, 100, 125, 150, 175, 200, or 225. That is, the composition comprising a cryoprecipitate or cryo-poor plasma of the present disclosure may include Factor VIII at any amount within a range having an upper limit of 480, 450, 400, 350, 300, 250, 225, 200, 175, 150, 125, 100, 95, 90, 85, 80, 75, 70, 65, 60, 55, 50, 45, 40, 35, 30, 25, 20, or 15 IU and an independently selected lower limit of 10, 15, 20, 25, 30, 35, 40, 45, 50, 55, 60, 65, 70, 75, 80, 85, 90, 95, 100, 125, 150, 175, 200, or 225 IU, wherein the upper limit is greater than the lower limit. In other embodiments, a cryoprecipitate or cryoprecipitate composition of the present disclosure contains at least 80 IU of Factor VIII per unit (e.g., 200 mL unit, per unit of cryoprecipitate derived from about 200 mL of plasma) of cryoprecipitate. In some embodiments, a cryoprecipitate or cryoprecipitate composition of the present disclosure contains at least 80 IU of Factor VIII. In some embodiments, a cryoprecipitate or cryoprecipitate composition of the present disclosure contains 80-100 IU of Factor VIII per unit (e.g., 200 mL unit, per unit of cryoprecipitate derived from about 200 mL of plasma) of cryoprecipitate. Factor VIII content of a cryoprecipitate or cryoprecipitate composition of the present disclosure may be expressed per unit volume (e.g., per unit of cryoprecipitate derived from about 200 mL of plasma), or as an absolute amount. In some embodiments, a cryoprecipitate or cryoprecipitate composition of the present disclosure contains less than about 80 IU or less than about 50 IU of Factor VIII per unit (e.g., 200 mL unit, per unit of cryoprecipitate derived from about 200 mL of plasma) of cryoprecipitate at the time of thawing (e.g., within about 1 hour or within about 2 hours of thawing). In some embodiments, a cryoprecipitate or cryoprecipitate composition of the present disclosure contains less than about 80 IU or less than about 50 IU of Factor VIII per unit of cryoprecipitate at or shortly preceding the infusion (e.g., up to about 1 day, up to about 3 days, up to about 5 days, or up to about 7 days after thawing). In some embodiments, a cryoprecipitate or cryoprecipitate composition of the present disclosure contains less than about 80 IU of Factor VIII at or shortly preceding the infusion (e.g., up to about 1 day, up to about 3 days, up to about 5 days, or up to about 7 days after thawing). In some embodiments, a cryoprecipitate or cryoprecipitate composition of the present disclosure contains at least about 80 IU of Factor VIII at or shortly preceding the infusion (e.g., up to about 1 day, up to about 3 days, up to about 5 days, or up to about 7 days after thawing). In some embodiments, a cryoprecipitate or cryoprecipitate composition of the present disclosure contains 80-100 IU of Factor VIII at or shortly preceding the infusion (e.g., up to about 1 day, up to about 3 days, up to about 5 days, or up to about 7 days after thawing). In some embodiments, a cryoprecipitate or cryoprecipitate composition of the present disclosure contains comprises about 80-240 IU (e.g., total IU) of Factor VIII at or shortly preceding the infusion (e.g., up to about 1 day, up to about 3 days, up to about 5 days, or up to about 7 days after thawing). In some embodiments, a cryoprecipitate or cryoprecipitate composition of the present disclosure contains comprises about 80-480 IU (e.g., total IU) of Factor VIII at or shortly preceding the infusion (e.g., up to about 1 day, up to about 3 days, up to about 5 days, or up to about 7 days after thawing). In some embodiments, an amount of factor VIII is determined from cryoprecipitate sampled within about 2 hours, within about 6 hours, within about 1 day, within about 2 days, within about 3 days, within about 4 days, or within about 5 days after thawing.

In some embodiments, a composition contains cryoprecipitate prepared from at least about 550 mL and less than about 650 mL of pathogen-inactivated plasma. In some embodiments, a composition contains two or more cryoprecipitates, each of the two or more cryoprecipitates prepared from at least about 150 mL and less than about 250 mL of plasma, e.g., about 200 mL of plasma. In some embodiments, cryoprecipitate prepared from at least about 550 mL and less than about 650 mL of pathogen-inactivated plasma contains between about 80 and about 200 IU of Factor VIII, e.g., at or shortly preceding the infusion (e.g., up to about 1 day, up to about 3 days, up to about 5 days, or up to about 7 days after thawing). For example, in some embodiments, cryoprecipitate prepared from at least about 550 mL and less than about 650 mL of pathogen-inactivated plasma contains between about 80 and about 200 IU of Factor VIII at the time of thawing (e.g., within about 1 hour or within about 2 hours of thawing). In some embodiments, cryoprecipitate prepared from at least about 550 mL and less than about 650 mL of pathogen-inactivated plasma contains between about 80 and about 200 IU of Factor VIII as determined within about 2 hours, within about 6 hours, within about 1 day, within about 2 days, within about 3 days, within about 4 days, or within about 5 days after thawing.

In some embodiments, a composition contains a first cryoprecipitate prepared from at least about 550 mL and less than about 650 mL of pathogen-inactivated plasma and a second cryoprecipitate prepared from at least about 550 mL and less than about 650 mL of pathogen-inactivated plasma. In some embodiments, a composition containing two cryoprecipitates, each prepared from at least about 550 mL and less than about 650 mL of pathogen-inactivated plasma, contains between about 160 and about 400 IU of Factor VIII, e.g., at or shortly preceding the infusion (e.g., up to about 1 day, up to about 3 days, up to about 5 days, or up to about 7 days after thawing). For example, in some embodiments, a composition containing two cryoprecipitates, each prepared from at least about 550 mL and less than about 650 mL of pathogen-inactivated plasma, contains between about 160 and about 400 IU of Factor VIII at the time of thawing (e.g., within about 1 hour or within about 2 hours of thawing). In some embodiments, a composition containing two cryoprecipitates, each prepared from at least about 550 mL and less than about 650 mL of pathogen-inactivated plasma, contains between about 160 and about 400 IU of Factor VIII as determined within about 2 hours, within about 6 hours, within about 1 day, within about 2 days, within about 3 days, within about 4 days, or within about 5 days after thawing.

In some embodiments, a cryoprecipitate or cryoprecipitate composition or cryo-poor plasma of the present disclosure may be tested for fibrinogen. Various assays for measuring fibrinogen are known in the art, including without limitation the Clauss method, prothrombin time-derived assays, immunological assays, and gravimetric assays. In some embodiments, a cryoprecipitate or cryoprecipitate composition or cryo-poor plasma of the present disclosure contains an amount of fibrinogen meeting AABB standards. In some embodiments, a cryoprecipitate or cryoprecipitate composition or cryo-poor plasma of the present disclosure contains at least about 100, at least about 150, at least about 200, at least about 250, or at least about 300 mg of fibrinogen per unit of cryoprecipitate (e.g., per unit of cryoprecipitate derived from about 200 mL of plasma). In some embodiments, a composition comprising a cryoprecipitate or cryo-poor plasma of the present disclosure includes fibrinogen at an amount that is less than about any of the following amounts (in mg, either absolute or per unit of cryoprecipitate): 2500, 2000, 1800, 1500, 1200, 750, 700, 650, 600, 550, 500, 450, 400, 350, 300, 250, 200, or 150. In some embodiments, a composition comprising a cryoprecipitate or cryo-poor plasma of the present disclosure includes fibrinogen at an amount that is greater than about any of the following amounts (in mg, either absolute or per unit of cryoprecipitate): 140, 150, 200, 250, 300, 350, 400, 450, 500, 550, 600, 650, 700, 750, 800, 850, 900, 1000, 1100, 1200, or 1500. That is, the composition comprising a cryoprecipitate or cryo-poor plasma of the present disclosure may include fibrinogen at any amount within a range having an upper limit of 2500, 2000, 1800, 1500, 1200, 750, 700, 650, 600, 550, 500, 450, 400, 350, 300, 250, 200, or 150 mg and an independently selected lower limit of 140, 150, 200, 250, 300, 350, 400, 450, 500, 550, 600, 650, 700, 140, 150, 200, 250, 300, 350, 400, 450, 500, 550, 600, 650, 700, 750, 800, 850, 900, 1000, 1100, 1200, or 1500 mg, wherein the upper limit is greater than the lower limit. In some embodiments, a cryoprecipitate or cryoprecipitate composition or cryo-poor plasma of the present disclosure contains at least about 250 mg or at least about 150 mg of fibrinogen per unit of cryoprecipitate (e.g., per unit of cryoprecipitate derived from about 200 mL of plasma) or cryo-poor plasma at the time of thawing (e.g., within about 1 hour or within about 2 hours of thawing). In some embodiments, a cryoprecipitate or cryoprecipitate composition or cryo-poor plasma of the present disclosure contains at least about 250 mg or at least about 150 mg of fibrinogen per unit of cryoprecipitate (e.g., per unit of cryoprecipitate derived from about 200 mL of plasma) or cryo-poor plasma at or shortly preceding the infusion (e.g., up to about 1 day, up to about 3 days, up to about 5 days, or up to about 7 days after thawing). In some embodiments, a cryoprecipitate or cryoprecipitate composition or cryo-poor plasma of the present disclosure contains at least about 250 mg or at least about 150 mg of fibrinogen at the time of thawing (e.g., within about 1 hour or within about 2 hours of thawing). In some embodiments, a cryoprecipitate or cryoprecipitate composition or cryo-poor plasma of the present disclosure contains at least about 750 mg of fibrinogen (e.g., total mg of fibrinogen) at or shortly preceding the infusion (e.g., up to about 1 day, up to about 3 days, up to about 5 days, or up to about 7 days after thawing). In some embodiments, a cryoprecipitate or cryoprecipitate composition or cryo-poor plasma of the present disclosure contains at least about 750 mg of fibrinogen (e.g., total mg of fibrinogen) at the time of thawing (e.g., within about 1 hour or within about 2 hours of thawing). In some embodiments, an amount of fibrinogen is determined from cryoprecipitate sampled within about 2 hours, within about 6 hours, within about 1 day, within about 2 days, within about 3 days, within about 4 days, or within about 5 days after thawing.

In some embodiments, a composition contains cryoprecipitate prepared from at least about 550 mL and less than about 650 mL of pathogen-inactivated plasma. In some embodiments, a composition contains two or more cryoprecipitates, each of the two or more cryoprecipitates prepared from at least about 150 mL and less than about 250 mL of plasma, e.g., about 200 mL of plasma. In some embodiments, cryoprecipitate prepared from at least about 550 mL and less than about 650 mL of pathogen-inactivated plasma contains between about 700 mg and about 1000 mg of fibrinogen, e.g., at or shortly preceding the infusion (e.g., up to about 1 day, up to about 3 days, up to about 5 days, or up to about 7 days after thawing). For example, in some embodiments, cryoprecipitate prepared from at least about 550 mL and less than about 650 mL of pathogen-inactivated plasma contains between about 700 mg and about 1000 mg of fibrinogen at the time of thawing (e.g., within about 1 hour or within about 2 hours of thawing). In some embodiments, cryoprecipitate prepared from at least about 550 mL and less than about 650 mL of pathogen-inactivated plasma contains between about 700 mg and about 1000 mg of fibrinogen as determined within about 2 hours, within about 6 hours, within about 1 day, within about 2 days, within about 3 days, within about 4 days, or within about 5 days after thawing.

In some embodiments, a composition contains a first cryoprecipitate prepared from at least about 550 mL and less than about 650 mL of pathogen-inactivated plasma and a second cryoprecipitate prepared from at least about 550 mL and less than about 650 mL of pathogen-inactivated plasma. In some embodiments, a composition containing two cryoprecipitates, each prepared from at least about 550 mL and less than about 650 mL of pathogen-inactivated plasma, contains between about 1400 mg and about 2000 mg of fibrinogen, e.g., at or shortly preceding the infusion (e.g., up to about 1 day, up to about 3 days, up to about 5 days, or up to about 7 days after thawing). For example, in some embodiments, a composition containing two cryoprecipitates, each prepared from at least about 550 mL and less than about 650 mL of pathogen-inactivated plasma, contains between about 1400 mg and about 2000 mg of fibrinogen at the time of thawing (e.g., within about 1 hour or within about 2 hours of thawing). In some embodiments, a composition containing two cryoprecipitates, each prepared from at least about 550 mL and less than about 650 mL of pathogen-inactivated plasma, contains between about 1400 mg and about 2000 mg of fibrinogen as determined within about 2 hours, within about 6 hours, within about 1 day, within about 2 days, within about 3 days, within about 4 days, or within about 5 days after thawing.

In some embodiments, a cryoprecipitate or cryoprecipitate composition of the present disclosure may be tested for vWF. Various assays for measuring vWF (such as vWF:RCo and vWF:Ag assays) are known in the art, including without limitation vWF ELISA, platelet agglutination, flow cytometry, and latex immunoassays. In some embodiments, a cryoprecipitate or cryoprecipitate composition of the present disclosure contains an amount of vWF meeting AABB standards. In some embodiments, a cryoprecipitate or cryoprecipitate composition of the present disclosure contains at least about 80, at least about 90, at least about 100, at least about 110, at least about 120, at least about 130, at least about 140, or at least about 150 IU of vWF per unit of cryoprecipitate (e.g., per unit of cryoprecipitate derived from about 200 mL of plasma). In some embodiments, a composition comprising a cryoprecipitate of the present disclosure includes vWF at an amount that is less than about any of the following amounts (in IU, either absolute or per unit of cryoprecipitate): 450, 400, 350, 300, 250, 200, 150, 140, 130, 120, 110, 100, or 90. In some embodiments, a composition comprising a cryoprecipitate of the present disclosure includes vWF at an amount that is greater than about any of the following amounts (in IU, either absolute or per unit of cryoprecipitate): 80, 90, 100, 110, 120, 130, 140, 150, 200, 250, 300, 350, or 400. That is, the composition comprising a cryoprecipitate of the present disclosure may include vWF at any amount within a range having an upper limit of 450, 400, 350, 300, 250, 200, 150, 140, 130, 120, 110, 100, or 90 IU and an independently selected lower limit of 80, 90, 100, 110, 120, 130, 140, 150, 200, 250, 300, 350, or 400 IU, wherein the upper limit is greater than the lower limit. In some embodiments, a cryoprecipitate or cryoprecipitate composition of the present disclosure contains at least about 100 IU or at least about 150 IU of vWF per unit of cryoprecipitate at the time of thawing (e.g., within about 1 hour or within about 2 hours of thawing). In some embodiments, a cryoprecipitate or cryoprecipitate composition of the present disclosure contains at least about 100 IU or at least about 150 IU of vWF per unit of cryoprecipitate at or shortly preceding the infusion (e.g., up to about 1 day, up to about 3 days, up to about 5 days, or up to about 7 days after thawing).

In some embodiments, a cryoprecipitate or cryoprecipitate composition of the present disclosure may be tested for Factor XIII. Various assays for measuring Factor XIII are known in the art, including without limitation the Berichrom assay, the clot solubility assay, and a Factor XIII ELISA. In some embodiments, a cryoprecipitate or cryoprecipitate composition of the present disclosure contains an amount of Factor XIII meeting AABB standards. In some embodiments, a cryoprecipitate or cryoprecipitate composition of the present disclosure contains at least about 40, at least about 50, at least about 60, at least about 70, at least about 80, at least about 90, or at least about 100 IU of Factor XIII per unit of cryoprecipitate (e.g., per unit of cryoprecipitate derived from about 200 mL of plasma). In some embodiments, a composition comprising a cryoprecipitate of the present disclosure includes Factor XIII at an amount that is less than about any of the following amounts (in IU, either absolute or per unit of cryoprecipitate): 300, 275, 250, 225, 200, 175, 150, 125, 100, 90, 80, 70, 60, or 50. In some embodiments, a composition comprising a cryoprecipitate of the present disclosure includes Factor XIII at an amount that is greater than about any of the following amounts (in IU, either absolute or per unit of cryoprecipitate): 40, 50, 60, 70, 80, 90, 100, 125, 150, 175, 200, 225, 250, or 275. That is, the composition comprising a cryoprecipitate of the present disclosure may include Factor XIII at any amount within a range having an upper limit of 300, 275, 250, 225, 200, 175, 150, 125, 100, 90, 80, 70, 60, or 50 IU and an independently selected lower limit of 40, 50, 60, 70, 80, 90, 100, 125, 150, 175, 200, 225, 250, or 275 IU, wherein the upper limit is greater than the lower limit. In some embodiments, a cryoprecipitate or cryoprecipitate composition of the present disclosure contains at least about 100 IU or at least about 150 IU of Factor XIII per unit of cryoprecipitate at the time of thawing (e.g., within about 1 hour or within about 2 hours of thawing). In some embodiments, a cryoprecipitate or cryoprecipitate composition of the present disclosure contains at least about 100 IU or at least about 150 IU of Factor XIII per unit of cryoprecipitate at or shortly preceding the infusion (e.g., up to about 1 day, up to about 3 days, up to about 5 days, or up to about 7 days after thawing).

Any of the above amounts of cryoprecipitate or cryo-poor plasma components may be combined in any number or combination described herein. For example, in some embodiments, a cryoprecipitate or cryoprecipitate composition or cryo-poor plasma of the present disclosure contains less than about 80 IU or less than about 50 IU of Factor VIII per unit of cryoprecipitate or cryo-poor plasma and at least about 250 mg or at least about 150 mg of fibrinogen per unit of cryoprecipitate or cryo-poor plasma at the time of thawing (e.g., within about 1 hour or within about 2 hours of thawing). In some embodiments, a cryoprecipitate or cryoprecipitate composition or cryo-poor plasma of the present disclosure contains less than about 80 IU or less than about 50 IU of Factor VIII per unit of cryoprecipitate or cryo-poor plasma and at least about 250 mg or at least about 150 mg of fibrinogen per unit of cryoprecipitate or cryo-poor plasma at or shortly preceding the infusion (e.g., up to about 1 day, up to about 3 days, up to about 5 days, or up to about 7 days after thawing).

In some embodiments, a cryoprecipitate, cryoprecipitate composition, and/or cryo-poor plasma of the present disclosure may be prepared from plasma other than group O plasma, e.g., group A, B, and/or AB plasma. In some embodiments, a cryoprecipitate, cryoprecipitate composition, and/or cryo-poor plasma of the present disclosure may be prepared from plasma of more than one ABO type. In some embodiments, a cryoprecipitate, cryoprecipitate composition, and/or cryo-poor plasma of the present disclosure may be prepared from A, B, and AB type plasma.

In some embodiments, a cryoprecipitate, cryoprecipitate composition, and/or cryo-poor plasma of the present disclosure may be contained in a container of the present disclosure. In some embodiments, the container further comprises a label indicating that the composition is suitable for use (e.g., suitable for infusion) for up to about 1 day, 2 days, 3 days, 4 days, 5 days, 6 days, or 7 days after thawing.

Further provided herein is a cryoprecipitate produced by any of the methods of the present disclosure, e.g., including one or more of the aspects and features described above in any order or combination.

Cryoprecipitate and/or Cryo-Poor Plasma Kits or Articles of Manufacture

In some embodiments, a cryoprecipitate, cryoprecipitate composition, and/or cryo-poor plasma of the present disclosure, or one produced by the methods of the present disclosure, may be packaged in a kit or article of manufacture. In some embodiments, a kit or article of manufacture may include a container, a pathogen-inactivated cryoprecipitate and/or cryo-poor plasma, and instructions for using the pathogen-inactivated cryoprecipitate and/or cryo-poor plasma. In some embodiments, a kit or article of manufacture may include a container, a pathogen-inactivated cryoprecipitate and/or cryo-poor plasma, and a label indicating that the pathogen-inactivated cryoprecipitate and/or cryo-poor plasma is suitable for use for up to about 1 day, up to about 2 days, up to about 3 days, up to about 4 days, up to about 5 days, up to about 6 days, or up to about 7 days after thawing. In some embodiments, a kit or article of manufacture may further include any other material or device useful in a treatment (e.g., a transfusion), including without limitation one or more containers, tubing, sterilizing agents or equipment, cannulae, syringes, and the like.

In some embodiments, the instructions may be for using the pathogen-inactivated cryoprecipitate and/or cryo-poor plasma in an infusion into a subject. In some embodiments, the instructions may indicate an expiry date of the cryoprecipitate and/or cryo-poor plasma, e.g., a date by which the cryoprecipitate and/or cryo-poor plasma should be used in a treatment (e.g., an infusion) after thawing. In some embodiments, the instructions may indicate that the cryoprecipitate and/or cryo-poor plasma is suitable for infusion into the subject for up to about 1 day, up to about 2 days, up to about 3 days, up to about 4 days, up to about 5 days, up to about 6 days, or up to about 7 days after thawing. In some embodiments, the instructions may indicate that the cryoprecipitate and/or cryo-poor plasma is suitable for infusion into the subject for up to about 6 hours, up to about 12 hours, up to about 24 hours, up to about 36 hours, up to about 48 hours, up to about 60 hours, up to about 72 hours, up to about 84 hours, up to about 96 hours, up to about 108 hours, up to about 120 hours, up to about 132 hours, up to about 144 hours, up to about 156 hours, or up to about 168 hours after thawing.

Cryoprecipitate and/or Cryo-Poor Plasma Methods

Certain aspects of the present disclosure relate to methods of preparing a cryoprecipitate and/or cryo-poor plasma for infusion into a subject. Certain aspects of the present disclosure relate to methods of infusing a cryoprecipitate and/or cryo-poor plasma into a subject. It is to be understood that any of the cryoprecipitate, cryoprecipitate compositions, and/or cryo-poor plasma of the present disclosure may find use in any of the methods described herein. It is to be understood that any of the features or aspects of cryoprecipitate, cryoprecipitate compositions, and/or cryo-poor plasma of the present disclosure described herein may find use in any of the methods described herein in any combination.

In some embodiments, the methods of preparing a cryoprecipitate and/or cryo-poor plasma for infusion into a subject and/or methods of infusing a cryoprecipitate and/or cryo-poor plasma into a subject may include preparing a cryoprecipitate, cryoprecipitate composition, and/or cryo-poor plasma of the present disclosure from pathogen-inactivated plasma. Any of the exemplary methods of preparing a cryoprecipitate and/or cryo-poor plasma from plasma (e.g., pathogen-inactivated plasma) described herein (e.g., supra), or any methods of preparing a cryoprecipitate and/or cryo-poor plasma from plasma known in the art, may be used. Any of the exemplary methods of pathogen inactivating plasma described herein (e.g., infra), or any methods of pathogen inactivating plasma known in the art, may be used to generate the pathogen-inactivated plasma.

In some embodiments, the methods of preparing a cryoprecipitate and/or cryo-poor plasma for infusion into a subject and/or methods of infusing a cryoprecipitate and/or cryo-poor plasma into a subject may include freezing a cryoprecipitate, cryoprecipitate composition, and/or cryo-poor plasma of the present disclosure, e.g., as described supra or as is known in the art.

In some embodiments, the methods of preparing a cryoprecipitate and/or cryo-poor plasma for infusion into a subject and/or methods of infusing a cryoprecipitate and/or cryo-poor plasma into a subject may include thawing a frozen cryoprecipitate, cryoprecipitate composition, and/or cryo-poor plasma of the present disclosure, e.g., as described supra or as is known in the art. In some embodiments, the thawed cryoprecipitate, cryoprecipitate composition, and/or cryo-poor plasma may be suitable for infusion into a subject as described herein for at least about 1 day, at least about 2 days, at least about 3 days, at least about 4 days, at least about 5 days, at least about 6 days, or at least about 7 days after thawing. In some embodiments, the thawed cryoprecipitate, cryoprecipitate composition, and/or cryo-poor plasma may be suitable for infusion into a subject as described herein for at least about 6 hours, at least about 12 hours, at least about 24 hours, at least about 36 hours, at least about 48 hours, at least about 60 hours, at least about 72 hours, at least about 84 hours, at least about 96 hours, at least about 108 hours, at least about 120 hours, at least about 132 hours, at least about 144 hours, at least about 156 hours, or at least about 168 hours after thawing.

In some embodiments, the methods of preparing a cryoprecipitate for infusion into a subject and/or methods of infusing a cryoprecipitate into a subject may include testing the thawed cryoprecipitate (e.g., testing one or more representative random cryoprecipitate preparations) for Factor VIII, e.g., as described herein or known in the art. In some embodiments, the thawed cryoprecipitate may be tested for Factor VIII prior to infusion. In some embodiments, the thawed cryoprecipitate may have been tested for Factor VIII prior to freezing. In other embodiments, the methods of preparing a cryoprecipitate for infusion into a subject and/or methods of infusing a cryoprecipitate into a subject may exclude testing the thawed cryoprecipitate for Factor VIII. In some embodiments, the methods of preparing a cryoprecipitate for infusion into a subject and/or methods of infusing a cryoprecipitate into a subject may include testing the thawed cryoprecipitate for fibrinogen, but exclude testing for Factor VIII.

In some embodiments, the methods of preparing a cryoprecipitate for infusion into a subject and/or methods of infusing a cryoprecipitate into a subject may include testing the thawed cryoprecipitate (e.g., testing one or more representative random cryoprecipitate preparations) for fibrinogen, e.g., as described herein or known in the art. In some embodiments, the thawed cryoprecipitate may be tested for fibrinogen prior to infusion. In some embodiments, the thawed cryoprecipitate may have been tested for fibrinogen prior to freezing. In other embodiments, the methods of preparing a cryoprecipitate for infusion into a subject and/or methods of infusing a cryoprecipitate into a subject may exclude testing the thawed cryoprecipitate for fibrinogen.

In some embodiments, the methods of preparing a cryoprecipitate and/or cryo-poor plasma for infusion into a subject and/or methods of infusing a cryoprecipitate and/or cryo-poor plasma into a subject may include a cryoprecipitate and/or cryo-poor plasma made from about 600 mL of pathogen-inactivated plasma, from at least about 550 mL and less than 650 mL of pathogen-inactivated plasma, from at least about 570 mL and less than 620 mL of pathogen-inactivated plasma, or from at least about 600 mL and less than 650 mL of pathogen-inactivated plasma. Such a cryoprecipitate and/or cryo-poor plasma may be obtained, e.g., from pooling multiple unit volumes of plasma (e.g., 200 mL unit volumes, AABB unit volumes, to yield 550-650 mL), or from pooling multiple cryoprecipitates and/or cryo-poor plasma obtained from different samples of plasma. Individual cryoprecipitates and/or cryo-poor plasma may be combined or pooled after cryoprecipitate/cryo-poor plasma production but prior to re-freezing for storage, and/or individual plasma samples may be combined or pooled prior to use, storage at room temperature or under refrigeration, and/or cryoprecipitate production. In some embodiments, two or more cryoprecipitates and/or cryo-poor plasma may be combined prior to using, storing, and/or freezing the cryoprecipitate and/or cryo-poor plasma. In some embodiments, two or more cryoprecipitates and/or cryo-poor plasma may be combined after freezing the cryoprecipitate and/or cryo-poor plasma but prior to infusion.

In some embodiments, the methods of the present disclosure may further comprise infusing a cryoprecipitate or cryoprecipitate composition of the present disclosure into a subject. Methods of infusing a cryoprecipitate into a subject are well known in the art. In some embodiments, the cryoprecipitate may be infused at a rate of about 1 mL, about 2 mL, about 3 mL, about 4 mL, about 5 mL, about 6 mL, about 7 mL, about 8 mL, about 9 mL, or about 10 mL per minute, or for a total duration of about 30 minutes to about 4 hours. In some embodiments, a pool of cryoprecipitates (e.g., equivalent to 2, 3, 4, 5, 6, 7, 8, 9, 10, 11, or 12 units) may be infused. In some embodiments, the infusion is sufficient to raise the subject's fibrinogen level by an amount from about 30 mg/dL to about 60 mg/dL, e.g., by about 40 mg/dL. In some embodiments, the infusion is a transfusion. Further description of cryoprecipitate infusion dosing, response, indications, and preparation may be found, e.g., in the American Red Cross Compendium of Transfusion Practice Guidelines, the disclosure of which is hereby incorporated by reference as it relates to cryoprecipitate infusion dosing, response, indications, and preparation.

Further disclosed herein are methods for preparing a cryoprecipitate and/or cryo-poor plasma for infusion into a subject. In some embodiments, the methods include preparing a cryoprecipitate and/or cryo-poor plasma from pathogen-inactivated plasma (e.g., as described herein) and freezing the cryoprecipitate and/or cryo-poor plasma. In some embodiments, the methods include preparing a cryoprecipitate a and/or cryo-poor plasma, respectively, from pathogen-inactivated plasma (e.g., as described herein) and storing the cryoprecipitate and/or cryo-poor plasma at room temperature or under refrigeration before using in an infusion. In some embodiments, the cryoprecipitate and/or cryo-poor plasma, respectively, is suitable for infusion into the subject for up to about 1 day, 2 days, 3 days, 4 days, 5 days 6 days, or 7 days after thawing, as described herein. In some embodiments, the cryoprecipitate and/or cryo-poor plasma is prepared from at least about 550 mL and less than about 650 mL of pathogen-inactivated plasma of the present disclosure. In certain embodiments, the cryoprecipitate and/or cryo-poor plasma is prepared from about 600 mL of pathogen-inactivated plasma of the present disclosure.

In some embodiments, the methods further include combining a first cryoprecipitate and/or cryo-poor plasma, respectively, prepared from at least about 150 mL and less than about 250 mL (e.g., about 200 mL) of pathogen-inactivated plasma of the present disclosure and a second cryoprecipitate and/or cryo-poor plasma, respectively, prepared from at least about 150 mL and less than about 250 mL (e.g., about 200 mL) of pathogen-inactivated plasma of the present disclosure. In some embodiments, the methods further include combining a first cryoprecipitate and/or cryo-poor plasma, respectively, prepared from at least about 550 mL and less than about 650 mL of pathogen-inactivated plasma of the present disclosure and a second cryoprecipitate and/or cryo-poor plasma, respectively, prepared from at least about 550 mL and less than about 650 mL of pathogen-inactivated plasma of the present disclosure. In some embodiments, the first and the second cryoprecipitates and/or cryo-poor plasma, respectively, are combined prior to freezing the cryoprecipitate and/or cryo-poor plasma. In certain embodiments, the first cryoprecipitate and/or cryo-poor plasma, respectively, is prepared from about 600 mL of pathogen-inactivated plasma of the present disclosure, and the second cryoprecipitate and/or cryo-poor plasma, respectively, is prepared from about 600 mL of pathogen-inactivated plasma of the present disclosure.

In some embodiments, the methods further include combining a first cryoprecipitate and/or cryo-poor plasma, respectively, prepared or obtained from 1-3 (e.g., 3) units of pathogen-inactivated plasma of the present disclosure and a second cryoprecipitate and/or cryo-poor plasma, respectively, prepared or obtained from 1-3 (e.g., 3) units of pathogen-inactivated plasma of the present disclosure. In some embodiments, the first and the second cryoprecipitates and/or cryo-poor plasma are combined prior to freezing the cryoprecipitate.

In any of the methods of the present disclosure, the subject may be a human. In other embodiments, the subject may be a veterinary subject.

Cryoprecipitate and/or Cryo-Poor Plasma Processing

Cryoprecipitate and/or cryo-poor plasma processing and the handling of blood products typically involves the use of blood compatible bag systems, which are well known in the art, as described, for example, in U.S. Pat. Nos. 5,405,343, 7,025,877, and 8,439,889, the disclosures of which are incorporated by reference herein for the disclosure of blood handling bags and systems. In general, a blood handling system includes more than one plastic container, typically plastic bags, where the bags are integrally connected with plastic tubing. Some of the containers described herein include such plastic bags as are known in the storage and handling of blood products, including cryoprecipitates. Blood handling bags typically can be designed to hold various volumes of fluid, including, but not limited to, volumes ranging from 50 mL to 2 liters, for example having up to a 1 liter capacity, up to a 1.5 liter capacity, or up to a 2 liter capacity. Examples of common blood-collection bags include such bags with volumes of 350 mL, 450 mL and 500 mL, among others. It is understood that when a method refers to a bag, it includes any such plastic bags used in blood handling. Where such bags are referred to as "removal bag", "product bag", "transfer bag", "collection bag," or "illumination bag", it is understood that these bags are typical blood handling bags, or are similar to such bags in nature. Plastic bags suitable for use according to the present disclosure include for example, those comprising PL2410, as well as other suitable plastics known in the art. Plastic bag materials include polyvinyl chloride, polyolefins, ethylene vinyl acetate, ethylene vinyl acetate blended with other plastics, and the like.

As described herein, where tubing is described as connecting e.g. two bags of a processing set, it is understood that the tubing may be joined at some point therebetween by another component of the connection between the two bags. For example, a removal bag connected to a product bag by tubing includes wherein the tubing comprises a filter between the two bags, i.e. the tubing is divided by a filter such that fluid flows from one bag to the other through the tubing and filter. In one example, tubing connecting a removal bag and a product bag can include a filter to remove any loose particles from fluid flowing from the removal device to the product bag, i.e. the tubing is divided by, or interrupted by the filter between the bags. Such filters are designed to remove any small particles that may come off of the removal device, while allowing platelets to pass through the filter. The tubing between bags allows for fluid to flow from one bag to another, which can be blocked to prevent the flow until necessary, e.g. as part of the processing the fluid in one bag may be prevented from flowing to the next bag until required for the next step in a process. As such an openable seal, such as a clamp, plug, valve or the like is included in or on the tubing connecting the bags, where the clamp, plug, valve or the like can be selectively opened as required, for example to transfer the fluid from one bag to the next. In certain preferred embodiments, the tubing between bags comprises a breakable seal, such as a breakable valve, whereupon breaking the breakable seal allows for the blood solution to flow between the bags through the tubing. It is understood that the breakable seal is contained within the connection between containers, such that sterility of the system is maintained. It is also understood that a tubing comprising a filter, or a breakable seal, includes where the tubing may be interrupted by the filter or the seal, for example the tubing runs from one bag and is connected to the filter or seal (an incoming portion of the tubing), and the tubing continues from another portion of the filter or seal to another bag (an outgoing portion of the tubing). In such a configuration, fluid flows from the first bag, through the incoming portion of the tubing, through the filter or seal, and through the outgoing portion of the tubing and into the other bag.

Different bags within a blood bag system can be used for different steps of a process. For example, a system of bags to be used for the pathogen inactivation of a unit of cryoprecipitate or plasma can include a container with pathogen inactivation compound contained within, a bag for receiving the unit of cryoprecipitate or plasma and a pathogen inactivation compound (e.g. an illumination bag), a bag for the illumination of the unit of cryoprecipitate or plasma when the pathogen inactivation method includes illumination (e.g., an illumination bag, and typically the same bag to receive the unit of cryoprecipitate or plasma and pathogen inactivation compound), a bag for the removal of pathogen inactivation compounds and/or by-products thereof from the treated unit of cryoprecipitate or plasma (e.g., referred to as a removal bag), and one or more bags for containing the final cryoprecipitate or plasma product, i.e. the pathogen inactivated cryoprecipitate or plasma unit that has the concentration of the inactivation compound and/or by-products thereof reduced to below a desired concentration, which is ready for use, can be stored for later use (e.g., referred to as a product bag), or in the case of plasma can be used to generate a cryoprecipitate. Each bag in the system is typically made up of a plastic material. For example, the container for containing a solution of pathogen inactivation compound can be made of a suitable plastic such as PL2411 (Baxter Healthcare), or other plastics such as polyvinyl chloride, polyolefins, ethylene vinyl acetate, ethylene vinyl acetate blended with other plastics, and the like. This container is also overwrapped with a material that is impermeable to light of a wavelength that will activate the photoactive pathogen inactivation compound (for example suitable plastic such as PL2420, Baxter Healthcare). The illumination bag for a photoactivated pathogen inactivation compound requires a clear, durable thermoplastic material that is translucent to light of the selected wavelength. Suitable plastics that are translucent to light in the UVA wavelength range include polyvinyl chloride, polyolefins, ethylene vinyl acetate, ethylene vinyl acetate blended with other plastics, or other blends of thermoplastic polymers. Such suitable plastics include PL2410 (Baxter Healthcare) and PL732 (Baxter Healthcare). Similar materials may be used to make the removal bag and the product bag. The product bags include those made of PL2410. Suitable bag materials are discussed, for example, in PCT publication number WO 2003078023, and U.S. Pat. No. 7,025,877, the disclosures of which are hereby incorporated by reference as it relates to such bag materials and related materials. In all cases, the materials used in preparing the processing set have to be sterilizable by known methods such as steam and gamma or electron beam radiation used to ensure sterility of the processing set. While these are exemplary materials for making the bags, the methods described herein are applicable to processes using any suitable bag material as would be readily available to one skilled in the art, and can also be used with containers other than bags. The bags used for illumination, removal, and storage are also designed to allow for gases such as oxygen and carbon dioxide to go into and out of the blood bag, so that the blood products therein have adequate oxygen supply and carbon dioxide levels during the processing and storage.

Pathogen Inactivation

Blood products, including cryoprecipitate, cryo-poor plasma, or plasma blood products such frozen plasma (e.g., FFP, PF24), may contain pathogens, or may be contaminated with pathogens during processing. As such, it is desirable to subject such blood products to a process in order to reduce the risk of transfusion-transmitted diseases. In some embodiments, plasma may be subjected to one or more treatments to inactivate pathogens (i.e., pathogen inactivation, pathogen reduction). In some embodiments, the pathogen-inactivated plasma may then be used to produce a cryoprecipitate and a cryo-poor plasma, as described herein. In some embodiments, cryoprecipitate and/or cryo-poor plasma may be subjected to one or more treatments to inactivate pathogens (i.e., pathogen inactivation, pathogen reduction).

Various methods are available to mitigate the risk of transfusion-associated disease transmission in cryoprecipitate, cryo-poor plasma or plasma-containing blood products. Aside from screening and detection of pathogens and subsequent elimination of contaminated blood products, processes that incorporate treatments to inactivate pathogens (i.e., pathogen inactivation, pathogen reduction) that may be present are available. Ideally, such a process results in the inactivation of a broad range of pathogens such as viruses, bacteria and parasites that may be present in the blood product. In certain embodiments, the method of pathogen inactivation is based on a solvent/detergent process to treat plasma (OCTAPLAS, Octapharma; Solheim et al., 2000, Transfusion, 40:84-90). In certain embodiments, the method of pathogen inactivation is a methylene blue process to treat plasma (THERAFLEX-MB, MacoPharma; Garwood et al., 2003, Transfusion 43:1238-1247). In certain embodiments, the method of pathogen inactivation is based on a riboflavin/UV light process to treat plasma (MIRASOL, TerumoBCT; Hornsey et al., 2009, Transfusion 49:2167-2172). In certain embodiments, the method of pathogen inactivation requires addition of an amount of pathogen inactivation compound to a unit of cryoprecipitate or plasma. For example, pathogen inactivation may involve the addition of a low molecular weight compound, such as for example a psoralen (e.g., amotosalen) that inactivates various pathogens (INTERCEPT Blood System, Cerus Corporation; Mintz et al., 2006, Transfusion 46:1693-1704).

In some embodiments, pathogen inactivation may involve photochemical inactivation (e.g., photoinactivation), which involves the addition of a photosensitizer that, when activated by illumination using light of suitable wavelengths, will inactivate a variety of pathogens that may be present. Two such methods include the addition of amotosalen or riboflavin to the blood product, with subsequent illumination with UV light. Other methods include illumination with UV light without addition of a photosensitizer, as well as illumination with other photoactive compounds, including psoralen derivatives other than amotosalen, isoalloxazines other than riboflavin, alloxazines, dyes such as phthalocyanines, phenothiazine dyes (e.g. methylene blue, azure B, azure C, thionine, toluidine blue), porphyrin derivatives (e.g. dihematoporphyrin ether, hematoporphyrin derivatives, benzoporphyrin derivatives, alkyl-substituted sapphyrin), and merocyanine 540 (Prodouz et al., Blood Cells 1992, 18(1):101-14; Sofer, Gail, BioPharm, August 2002).

In some embodiments, the pathogen inactivation is carried out using an INTERCEPT® Blood System (Cerus), such as the INTERCEPT® Blood System for Plasma. The INTERCEPT® Blood System is well known in the art as a system for pathogen inactivation, with widespread adoption in European blood centers and FDA approval in the United States. For greater description of the INTERCEPT® Blood System and pathogen inactivation methods and compositions related thereto, see, e.g., U.S. Pat. Nos. 5,399,719, 5,556,993, 5,578,736, 5,585,503, 5,593,823, 5,625,079, 5,654,443, 5,712,085, 5,871,900, 5,972,593, 6,004,741, 6,004,742, 6,017,691, 6,194,139, 6,218,100, 6,503,699, 6,544,727, 6,951,713, 7,037,642, and 7,611,831; and PCT publication numbers WO 1995000141, WO 1996014739, WO 1997021346, WO 1998030327, WO 1999034914, and WO1999034915, the disclosures of each of which are hereby incorporated by reference as they relate to pathogen inactivation in blood products.

As described above, plasma or cryoprecipitate or cryo-poor plasma may be subjected to pathogen inactivation. An exemplary process for using the INTERCEPT® Blood System to pathogen inactivate plasma is as follows. A sample of plasma (e.g., containing one or more than one plasma units, AABB units) in the illumination container may be brought into contact with amotosalen from the amotosalen container (e.g., by connecting through tubing and breaking the amotosalen container cannula to release the amotosalen). After sealing the illumination container, it may be illuminated with UV according to manufacturer's protocols. Once illuminated, the plasma may be transferred through tubing into one or more storage containers through a compound adsorption device (CAD). Optionally, if more than one storage container of plasma is to be pooled, they may be pooled into a larger blood bag (e.g., a 600-650 mL bag for three plasma units, e.g., 200 mL units, AABB plasma units; such as a 600 mL PVC transfer pack). Cryoprecipitate may then be prepared (e.g., in the larger blood bag) as described herein. Liquid plasma may then be removed, e.g., by draining into one or more bags. Optionally, more than one cryoprecipitate sample may be produced; if so, the individual cryoprecipitates samples may be combined in a single container through use of a sterile dock/tubing. Cryoprecipitate may then be frozen and stored. It will be understood by one of skill in the art that alternative steps, combinations of steps, and order of steps may be followed.

In some embodiments, plasma or cryoprecipitate or cryo-poor plasma may be pathogen-inactivated in a container (e.g., a blood bag or other container described herein) suitable for photochemical inactivation of plasma under sterile conditions. This container may be coupled to a CAD (e.g., as described and/or referenced above) such that plasma can be transferred from the container to the CAD under sterile conditions. In some embodiments, the CAD may further be coupled to one or more second containers, such that the plasma can be transferred from the CAD to the one or more second containers under sterile conditions. For example, one 600 mL PVC transfer pack or other larger blood bag may be used for a single second container, or more than one (e.g., three) smaller blood bags (e.g., sized for one AABB unit) may be used as second containers. The one or more second containers may be suitable for freezing pathogen-inactivated plasma followed by thawing the pathogen-inactivated plasma under conditions that provide for the formation of cryoprecipitate. In some embodiments, a third container may be coupled to the one or more second containers, such that the pathogen-inactivated plasma can be transferred from the CAD to the one or more second containers to the third container under sterile conditions. The third container may be suitable for freezing pathogen-inactivated plasma followed by thawing the pathogen-inactivated plasma under conditions that provide for the formation of cryoprecipitate. For example, pathogen-inactivated plasma from multiple (e.g., three) second containers may be transferred to and combined within a larger third container (e.g., a 600-650 mL bag) for subsequent cryoprecipitate preparation.

Other pathogen inactivation systems include, for example, those described in PCT publication numbers WO 2012071135; WO 2012018484; WO 2003090794; WO 2003049784; WO 1998018908; WO 1998030327; WO 1996008965; WO 1996039815; WO 1996039820; WO 1996040857; WO 1993000005; US patent application number US 20050202395; and U.S. Pat. Nos. 8,296,071 and 6,548,242, the disclosures of which are hereby incorporated by reference as they relate to pathogen inactivation in blood products. Where addition of a compound to the blood product is used for pathogen inactivation, whether the method requires illumination or not, in some instances it is desirable to remove any residual pathogen inactivation compound or by-product thereof.

Some pathogen inactivation methods may require the use of a removal device, i.e. a device for reducing the concentration of pathogen inactivation compound, such as a small organic compound, and by-products thereof, in a unit of cryoprecipitate or plasma while substantially maintaining a desired biological activity of the cryoprecipitate or plasma. In some instances, the removal device comprises porous adsorbent particles in an amount sufficient to reduce the pathogen inactivation compound to below a desired concentration, wherein the adsorbent particles have an affinity for the pathogen inactivation compound, where it is understood that such adsorbent particle can be selected to best adsorb the compound or compounds to be removed, with minimal effect on components that should not be removed or damaged by contact with the adsorbent particle. A variety of adsorbent particles are known, including generally particles made from any natural or synthetic material capable of interacting with compounds to be removed, including particulates made of natural materials such as activated carbon, silica, diatomaceous earth, and cellulose, and synthetic materials such as hydrophobic resins, hydrophilic resins or ion exchange resins. Such synthetic resins include, for example, carbonaceous materials, polystyrene, polyacrylic, polyacrylic ester, cation exchange resin, and polystyrene-divinylbenzene. Detailed description of such removal devices suitable for use in the methods as described herein can be found in PCT publication numbers WO 1996040857, WO 1998030327, WO 1999034914, and WO 2003078023, the disclosures of which are hereby incorporated by reference with respect to the discussion of such removal devices and the adsorbent particles and other materials used to prepare such devices. Exemplary adsorbent particles include, but are not limited to, Amberlite (Rohm and Haas) XAD-2, XAD-4, XAD-7, XAD-16, XAD-18, XAD-1180, XAD-1600, XAD-2000, XAD-2010; Amberchrom (Toso Haas) CG-71m, CG-71c, CG-161m, CG161c; Diaion Sepabeads (Mitsubishi Chemicals) HP20, SP206, SP207, SP850, HP2MG, HP20SS, SP20MS; Dowex (Dow Chemical) XUS-40285, XUS-40323, XUS-43493 (also referred to as Optipore V493 (dry form) or Optipore L493 (hydrated form)), Optipore V503, Optipore SD-2; Hypersol Macronet (Purolite) MN-100, MN-102, MN-150, MN-152, MN-170, MN-200, MN-202, MN-250, MN-252, MN-270, MN-300, MN-400, MN-500, MN-502, Purosorb (Purolite) PAD 350, PAD 400, PAD 428, PAD 500, PAD 550, PAD 600, PAD 700, PAD 900, and PAD 950. The material used to form the immobilized matrix comprises a low melting polymer, such as nylon, polyester, polyethylene, polyamide, polyolefin, polyvinyl alcohol, ethylene vinyl acetate, or polysulfone. In one example, the adsorbent particles immobilized in a matrix are in the form of a sintered medium. While it is understood that the methods and devices described herein encompass removal devices as are known in the art, such methods and devices may be exemplified using the removal device of an amotosalen inactivated blood product as is commercially available. Some such removal devices contain Hypersol Macronet MN-200 adsorbent contained within a sintered matrix, where the sintered matrix comprises PL2410 plastic as a binder. In one instance, the removal device comprises Hypersol Macronet MN-200 adsorbent in a sintered matrix comprising PL2410, wherein the Hypersol Macronet MN-200 is in an amount of about 5 g dry weight equivalent.

As various resins may require different processing when used to make the removal devices useful in the methods and devices as described herein, comparison of amounts of adsorbent resins described herein, unless otherwise indicated, are comparison of the dry weight of the resin. For example, the resins are dried to <5% water prior to processing, and the equivalent of the dry weight of adsorbent is used in comparing amounts of resin in use. For example, Hypersol Macronet MN-200 is processed to stabilize the adsorbent, or what is typically referred to as wetting the adsorbent, so as to be directly usable upon contact with a blood product unit. Such a wetted sample may include, for example, about 50% glycerol or other suitable wetting agent. In some embodiments, the adsorbent resin is a polystyrene-divinylbenzene resin. In some embodiments, the polystyrene-divinylbenzene resin is Hypersol Macronet MN-200. In some embodiments, the adsorbent is contained within a sintered matrix, wherein the sintered matrix comprises PL2410 binder. In some embodiments, Hypersol Macronet MN-200 adsorbent is contained within a sintered matrix to provide a removal device.

Cryosupernatant Preparation

It will be appreciated by one of skill in the art that, in the process of generating a cryoprecipitate or cryoprecipitate composition, a cryosupernatant (e.g., cryo-poor plasma, cryo-reduced plasma) of the present disclosure is also produced or formed. Such cryosupernatant may have medical uses of interest, such as infusion into a patient.

As such, disclosed herein are methods of preparing a cryo-poor plasma (e.g., pooled cryo-poor plasma, pooled cryosupernatant) for infusion into a subject. In some embodiments, the methods comprise combining at least a first plasma and a second plasma, and subjecting the combined (e.g., pooled) plasma to a pathogen inactivation process and freezing. In some embodiments, the at least first and second plasmas have a combined volume of at least about 550 mL and less than about 650 mL. In some embodiments, the methods comprise freezing at least a first pathogen-inactivated plasma and a second pathogen-inactivated plasma. In some embodiments, the first and the second pathogen-inactivated plasmas have a combined volume of at least about 550 mL and less than about 650 mL. In some embodiments, the first and the second pathogen-inactivated plasmas each have a volume of at least about 550 mL and less than about 650 mL. In some embodiments, the first and the second pathogen-inactivated plasmas have a combined volume of about 600 mL. In some embodiments, the first and the second pathogen-inactivated plasmas each have a volume of about 600 mL. In some embodiments, three units (e.g., AABB plasma units) may be used.

In some embodiments, the first and the second pathogen-inactivated plasmas may then be thawed under conditions that provide for the formation of cryoprecipitates (e.g., as described herein). In some embodiments, each cryoprecipitate may then be separated from the corresponding cryosupernatant. In some embodiments, the two cryosupernatants may then be combined to form a pooled cryosupernatant.

In some embodiments, two pooled cryosupernatants (prepared, e.g., as described above) may be combined. For example, two pooled cryosupernatants may be combined, where each of the pooled cryosupernatants is obtained from pooling cryosupernatants obtained from pathogen-inactivated plasmas totaling at least about 550 mL and less than about 650 mL, e.g., as described above. As such, in some embodiments, a pooled cryosupernatant may be obtained from 1100-1300 mL of pathogen-inactivated plasma.

In some embodiments, plasma or cryoprecipitate or cryo-poor plasma may be pathogen-inactivated in a container (e.g., a blood bag or other container described herein) suitable for photochemical inactivation of plasma under sterile conditions. This container may be coupled to a CAD (e.g., as described and/or referenced above) such that plasma can be transferred from the container to the CAD under sterile conditions. In some embodiments, this container may be coupled to an additional (e.g., upstream) container suitable for mixing the one or more units of plasma with a pathogen-inactivating compound (e.g., as described and/or referenced herein). In some embodiments, the additional container is coupled to the first container such that the one or more units of plasma in admixture with the pathogen-inactivating compound can be transferred from the additional container to the first container under sterile conditions. In some embodiments, the CAD may further be coupled to one or more second containers, such that the plasma can be transferred from the CAD to the one or more second containers under sterile conditions. For example, one 600 mL PVC transfer pack or other larger blood bag may be used for a single second container, or more than one (e.g., three) smaller blood bags (e.g., sized for one AABB unit) may be used as second containers. The one or more second containers may be suitable for freezing pathogen-inactivated plasma followed by thawing the pathogen-inactivated plasma under conditions that provide for the formation of cryoprecipitate. In some embodiments, a third container may be coupled to the one or more second containers, such that the pathogen-inactivated plasma can be transferred from the CAD to the one or more second containers to the third container under sterile conditions. The third container may be suitable for freezing pathogen-inactivated plasma followed by thawing the pathogen-inactivated plasma under conditions that provide for the formation of cryoprecipitate. For example, pathogen-inactivated plasma from multiple (e.g., three) second containers may be transferred to and combined within a larger third container (e.g., a 600-650 mL bag) for subsequent cryoprecipitate preparation. In some embodiments, pathogen-inactivated cryo-poor plasma can be transferred from the third container to a first of the two or more second containers, and the precipitate can be transferred from the third container to a second of the two or more second containers. In some embodiments (e.g., when three or more second containers are used), the pathogen-inactivated cryo-poor plasma is transferred from the third container to each of two second containers and the precipitate is transferred from the third container to a third second container. In some embodiments, the precipitate (e.g., the precipitate in the third second container) is resuspended in about 80 mL to about 120 mL of pathogen-inactivated plasma (e.g., in about 100 mL of pathogen-inactivated plasma), where the pathogen-inactivated plasma used for resuspension is optionally pathogen-inactivated cryo-poor plasma from the third container.

In some embodiments, cryosupernatant may be separated from cryoprecipitate in one or more fourth containers (e.g., one or more 600-650 mL bags). In some embodiments, the one or more fourth containers may be configured to be coupled to one or more second containers or a third container, as described above, such that the supernatant can be transferred from the one or more second containers or the third container to the one or more fourth containers under sterile conditions to afford a pathogen-inactivated cryosupernatant contained within the one or more fourth containers and a pathogen-inactivated cryoprecipitate contained within the one or more second containers or the third container.

In some embodiments, a therapeutically effective amount of pathogen-inactivated cryo-poor plasma is administered to a subject. In some embodiments, the subject is suffering from one or more of burns, blunt trauma, penetrating trauma, and hemorrhage. In some embodiments, the administration results in fluid resuscitation of the subject.

In some embodiments, prior to administering the pathogen-inactivated cryo-poor plasma to a subject, the pathogen-inactivated cryo-poor plasma is frozen (e.g., for frozen storage) and thawed (e.g., from frozen storage). In some embodiments, the pathogen-inactivated cryo-poor plasma is administered within 1 day, 2 days, 3 days, 4 days, 5 days, 6 days, or 7 days after thawing.

Further disclosed herein are methods for infusing a pathogen-inactivated plasma composition (e.g., frozen plasma, fresh frozen plasma, PF24, apheresis plasma, cryo-poor plasma, cryosupernatant) of the present disclosure into a subject.

Use of Plasma Compositions

Pathogen-inactivated plasma compositions of the present disclosure may be used for treating a variety of diseases and conditions. The pathogen-inactivated plasma compositions may include for example a pathogen-inactivated frozen plasma (e.g., whole blood collected plasma), such as a fresh frozen plasma (e.g., FFP) or a plasma frozen within 24 hr (e.g., PF24), a pathogen-inactivated apheresis collected plasma, and/or a plasma supernatant from a cryoprecipitate process (e.g., cryosupernatant, cryo-poor plasma). For example, pathogen-inactivated plasma compositions of the present disclosure may be used for treating a disease or condition indicated for treatment by plasma exchange (e.g., therapeutic plasma exchange) in a subject in need thereof, for example by administering to the subject a therapeutically effective amount of the pathogen-inactivated plasma composition by plasma exchange. In certain embodiments, the disease or condition is indicated for treatment with albumin by plasma exchange. Pathogen-inactivated plasma compositions of the present disclosure may also be used for treating a disease or condition indicated for treatment by intravenous infusion with immunoglobulin (e.g., intravenous immunoglobulin infusion, IVIG) in a subject in need thereof, for example by administering to the subject a therapeutically effective amount of the pathogen-inactivated plasma composition by plasma exchange. In certain embodiments, pathogen-inactivated plasma compositions of the present disclosure may be used for treating a disease or condition that is contra-indicated for treatment with a plasma (e.g., frozen plasma, FFP, cryo-poor plasma), for example by administering a therapeutically effective amount of the pathogen-inactivated plasma composition to a subject suffering from the disease or condition by plasma exchange. In some embodiments, a pathogen-inactivated plasma composition of the present disclosure is administered to a subject within 1 day, 2 days, 3 days, 4 days, 5 days, 6 days, or 7 days after thawing (e.g., from frozen storage).

Pathogen-inactivated plasma compositions of the present disclosure also may be used for treating a neurologic disease or condition. Non-limiting examples of neurologic diseases or conditions include, for example, Guillain-Barré syndrome, chronic inflammatory demyelinating polyneuropathy (CIDP), myasthenia gravis, paraproteinemic polyneuropathy (e.g., polyneuropathy associated with paraproteinaemias, paraproteinemic demyelinating neuropathy), PANDAS, Lambert-Eaton myasthenic syndrome, acute exacerbation of multiple sclerosis, chronic focal encephalitis and/or neuromyelitis optica.

Pathogen-inactivated plasma compositions of the present disclosure also may be used for treating a hematologic disease or condition. Non-limiting examples of hematologic diseases or conditions include, for example, hyperviscosity syndromes (e.g., paraproteinaemias, hyperviscosity in monoclonal gamopathies), cryoglobulinaemia (e.g., severe/symptomatic), haemopoietic stem cell transplantation (e.g., ABO-incompatible haemopoietic stem cell transplantation), pure red cell aplasia, cold agglutinin disease (e.g., life-threatening cold agglutinin disease), myeloma with cast nephropathy, red cell alloimmunisation in pregnancy, alloimmune thrombocytopenia and/or hemolytic disease of the newborn. Other non-limiting examples of hematologic diseases or conditions include, for example, thrombotic thrombocytopenic purpura (TTP) and hemolytic uremic syndrome (e.g., HUS, atypical hemolytic uremic syndrome, autoantibody to factor H).

Pathogen-inactivated plasma compositions of the present disclosure also may be used for treating a renal disease or condition. Non-limiting examples of renal diseases or conditions include, for example, Goodpasture's syndrome, anti-neutrophil cytoplasmic antibody (ANCA)-associated rapidly progressive glomerulonephritis, recurrent focal segmental glomerular sclerosis and/or antibody-mediated renal transplant rejection.

Pathogen-inactivated plasma compositions of the present disclosure also may be used for treating a metabolic disease or condition. Non-limiting examples of metabolic diseases or conditions include, for example, familial hypercholesterolaemia (e.g., homozygous), Wilson's disease (e.g., fulminant) and/or Refsum's disease.

Pathogen-inactivated plasma compositions of the present disclosure also may be used for treating an immunologic disease or condition. Non-limiting examples of immunologic diseases or conditions include, for example, catastrophic antiphospholipid syndrome and/or cerebral systemic lupus erythematosus (SLE).

Pathogen-inactivated plasma compositions of the present disclosure may be used for treating one or more of the following diseases or conditions, whereby a therapeutically effective amount of the pathogen-inactivated plasma composition is administered to a subject in need thereof by plasma exchange (e.g., therapeutic plasma exchange): Guillain-Barré syndrome, chronic inflammatory demyelinating polyneuropathy (e.g., CIDP, chronic inflammatory demyelinating polyradiculoneuropathy), myasthenia gravis, paraproteinemic polyneuropathy (e.g., polyneuropathy associated with paraproteinaemias, paraproteinemic demyelinating neuropathy), polyneuropathy associated with monoclonal gammopathy of undetermined significance (MGUS), PANDAS (Pediatric Autoimmune Neuropsychiatric Disorders Associated with Streptococcal Infections), hyperviscosity syndromes (e.g., paraproteinaemias, hyperviscosity in monoclonal gamopathies), cryoglobulinaemia (e.g., severe, symptomatic), Goodpasture's syndrome, anti-neutrophil cytoplasmic antibody (ANCA)-associated rapidly progressive glomerulonephritis, recurrent focal segmental glomerular sclerosis, antibody-mediated renal transplant rejection, familial hypercholesterolaemia (e.g., homozygous), Wilson's disease (e.g., fulminant Wilson's disease), Lambert-Eaton myasthenic syndrome, acute exacerbation of multiple sclerosis, chronic focal encephalitis, neuromyelitis optica, haemopoietic stem cell transplantation (e.g., ABO-incompatible haemopoietic stem cell transplantation), pure red cell aplasia, cold agglutinin disease (e.g., life-threatening cold agglutinin disease), hemolytic uremic syndrome (e.g., HUS, atypical hemolytic uremic syndrome, autoantibody to factor H), thrombotic thrombocytopenic purpura (TTP), myeloma with cast nephropathy, red cell alloimmunisation in pregnancy, catastrophic antiphospholipid syndrome, systemic lupus erythematosus (e.g., cerebral systemic lupus erythematosus, SLE), Refsum's disease, alloimmune thrombocytopenia, hemolytic disease of the newborn, Kawasaki disease, toxic epidermal necrolysis, Stevens Johnson syndrome (SJS), autoimmune haemolytic anaemia, clotting (e.g., coagulation) factor inhibitors, haemophagocytic syndrome, post-transfusion purpura, chronic inflammatory demyelinating polyradiculoneuropathy, inflammatory myelopathies, multifocal motor neuropathy, Rasmussen syndrome (e.g., Rasmussen encephalitis), stiff person syndrome, autoimmune congenital heart block, autoimmune uveitis, immunobullous diseases, necrotising staphylococcal sepsis, *Clostridium difficile* colitis (e.g., severe, recurrent), staphylococcal or streptococcal toxic shock syndrome, immune-mediated solid organ transplant rejection (e.g., treating or preventing antibody-mediated rejection after solid organ transplantation, treating or preventing ABO-incompatible solid organ transplant rejection, treating or preventing HLA-incompatible solid organ transplant rejection, desensitization to solid organ transplant), Wegener's granulomatosis, cryoglobulinemia, focal segmental glomerulosclerosis (e.g., recurrent), thrombotic microangiopathy (TMA) (e.g., drug-associated TMA), B-cell chronic lymphocytic leukemia (CLL), multifocal motor neuropathy (MMN), asthma, treatment or prevention of acute graft versus host disease (GVHD) and/or infection after allogeneic bone marrow transplant (BMT), myositis (e.g., dermatomyositis, polymyositis), CMV induced pneumonitis in solid organ transplantation (SOT), rheumatoid arthritis, Lambert-Eaton myasthenic syndrome (LEMS), Still's disease, vasculitides, bacterial infection in pediatric HIV (e.g., prevention), inclusion body myositis (IBM), acute disseminated encephalomyelitis, cardiomyopathy (e.g., dilated cardiomyopathy, idiopathic dilated cardiomyopathy), Henoch-Schonlein purpura (e.g., HSP, anaphylactoid purpura, purpura rheumatica), hyperleukocytosis, nephrogenic systemic fibrosis, paraneoplastic neurological syndromes, Sydenham's chorea, scleroderma, sudden sensorineural hearing loss, acute liver failure, aplastic anemia, burn shock resuscitation, cardiac transplant (e.g., treating or preventing ABO-incompatible cardiac transplant rejection, treating or preventing HLA-incompatible cardiac transplant rejection, desensitization to transplant), heparin-induced thrombocytopenia, hypertriglyceridemic pancreatitis, liver transplant (e.g., treating or preventing ABO-incompatible liver transplant rejection, treating or preventing HLA-incompatible liver transplant rejection, desensitization to transplant), lung allograft rejection, pemphigus vulgaris, poisoning, overdose, envenomation, renal transplant (e.g., treating or preventing ABO-incompatible renal transplant rejection, treating or preventing HLA-incompatible renal transplant rejection, desensitization to transplant), thyroid storm, sepsis (e.g., sepsis with multi-organ failure), immune complex rapidly progressive glomerulonephritis.

In certain embodiments, pathogen-inactivated plasma compositions of the present disclosure may be used for treating a disease or condition selected from the group consisting of Guillain-Barré syndrome, chronic inflammatory demyelinating polyneuropathy (e.g., CIDP, chronic inflammatory demyelinating polyradiculoneuropathy), myasthenia gravis, paraproteinemic polyneuropathy (e.g., polyneuropathy associated with paraproteinaemias, paraproteinemic demyelinating neuropathy), polyneuropathy associated with monoclonal gammopathy of undetermined significance (MGUS), PANDAS (Pediatric Autoimmune Neuropsychiatric Disorders Associated with Streptococcal Infections), hyperviscosity syndromes (e.g., paraproteinaemias, hyperviscosity in monoclonal gamopathies), cryoglobulinaemia (e.g., severe, symptomatic), Goodpasture's syndrome, antineutrophil cytoplasmic antibody (ANCA)-associated rapidly progressive glomerulonephritis, recurrent focal segmental glomerular sclerosis, antibody-mediated renal transplant rejection, familial hypercholesterolaemia (e.g., homozygous), Wilson's disease (e.g., fulminant Wilson's disease), Lambert-Eaton myasthenic syndrome, acute exacerbation of multiple sclerosis, chronic focal encephalitis, neuromyelitis optica, haemopoietic stem cell transplantation (e.g., ABO-incompatible haemopoietic stem cell transplantation), pure red cell aplasia, cold agglutinin disease (e.g., life-threatening cold agglutinin disease), myeloma with cast nephropathy, red cell alloimmunisation in pregnancy, catastrophic antiphospholipid syndrome, systemic lupus erythematosus (e.g., cerebral systemic lupus erythematosus, SLE), Refsum's disease, alloimmune thrombocytopenia, hemolytic disease of the newborn, Kawasaki disease, toxic epidermal necrolysis, Stevens Johnson syndrome (SJS), autoimmune haemolytic anaemia, clotting (e.g., coagulation) factor inhibitors, haemophagocytic syndrome, post-transfusion purpura, chronic inflammatory demyelinating polyradiculoneuropathy, inflammatory myelopathies, multifocal motor neuropathy, Rasmussen syndrome (e.g., Rasmussen encephalitis), stiff person syndrome, autoimmune congenital heart block, autoimmune uveitis, immunobullous diseases, necrotising staphylococcal sepsis, *Clostridium difficile* colitis (e.g., severe, recurrent), staphylococcal or streptococcal toxic shock syndrome, immune-mediated solid organ transplant rejection (e.g., treating or preventing antibody-mediated rejection after solid organ transplantation, treating or preventing ABO-incompatible solid organ transplant rejection, treating or preventing HLA-incompatible solid organ transplant rejection, desensitization to solid organ transplant), Wegener's granulomatosis, cryoglobulinemia, focal segmental glomerulosclerosis (e.g., recurrent), thrombotic microangiopathy (TMA) (e.g., drug-associated TMA), B-cell chronic lymphocytic leukemia (CLL), multifocal motor neuropathy (MMN), asthma, treatment or prevention of acute graft versus host disease (GVHD) and/or infection after allogeneic bone marrow transplant (BMT), myositis (e.g., dermatomyositis, polymyositis), CMV induced pneumonitis in solid organ transplantation (SOT), rheumatoid arthritis, Lambert-Eaton myasthenic syndrome (LEMS), Still's disease, vasculitides, bacterial infection in pediatric HIV (e.g., prevention), inclusion body myositis (IBM), acute disseminated encephalomyelitis, cardiomyopathy (e.g., dilated cardiomyopathy, idiopathic dilated cardiomyopathy), Henoch-Schonlein purpura (e.g., HSP, anaphylactoid purpura, purpura rheumatica), hyperleukocytosis, nephrogenic systemic fibrosis, paraneoplastic neurological syndromes, Sydenham's chorea, scleroderma, sudden sensorineural hearing loss, acute liver failure, aplastic anemia, burn shock resuscitation, cardiac transplant (e.g., treating or preventing ABO-incompatible cardiac transplant rejection, treating or preventing HLA-incompatible cardiac transplant rejection, desensitization to transplant), heparin-induced thrombocytopenia, hypertriglyceridemic pancreatitis, liver transplant (e.g., treating or preventing ABO-incompatible liver transplant rejection, treating or preventing HLA-incompatible liver transplant rejection, desensitization to transplant), lung allograft rejection, pemphigus vulgaris, poisoning, overdose, envenomation, renal transplant (e.g., treating or preventing ABO-incompatible renal transplant rejection, treating or preventing HLA-incompatible renal transplant rejection, desensitization to transplant), thyroid storm, sepsis (e.g., sepsis with multi-organ failure), immune complex rapidly progressive glomerulonephritis.

In certain embodiments, pathogen-inactivated plasma compositions of the present disclosure may be used for treating hemolytic uremic syndrome (e.g., HUS, atypical hemolytic uremic syndrome, autoantibody to factor H) or thrombotic thrombocytopenic purpura (TTP). For example, in some embodiments, the disclosure provides a method of treating thrombocytopenic purpura (TTP) or hemolytic-uremic syndrome (HUS) in a subject, comprising administering to a subject in need thereof a therapeutically effective amount of pathogen-inactivated plasma composition. In some embodiments, the pathogen-inactivated plasma composition comprises pathogen-inactivated cryo-poor plasma. In some embodiments, the pathogen-inactivated plasma composition is administered by plasma exchange.

Treatment with a pathogen-inactivated plasma composition of the present disclosure may be accomplished by administering a therapeutically effective amount of the pathogen-inactivated plasma by plasma exchange (e.g., therapeutic plasma exchange) to a subject in need thereof. In certain embodiments, a pathogen-inactivated plasma composition of the present disclosure may be administered in conjunction with (e.g., concurrently with, consecutively with, after) the administration of immunoglobulin by intravenous infusion (e.g., intravenous immunoglobulin infusion, IVIG).

Therapeutic plasma exchange is a treatment process well known in the art, whereby blood is separated into plasma and cellular components, followed by mixing of the cellular components with a replacement fluid and reinfusion into the patient (Winters, 2012, Hematology ASH Education Book 2012:7-12). TPE is generally an automated process performed using commercially available apheresis (e.g., plasmapheresis) devices, which can be divided into two broad categories: those that use filters to separate the plasma from the cellular components based on size, and those that use centrifugation to separate components based on density.

A plasma exchange using a plasma composition of the present disclosure may be performed using a variety of pathogen-inactivated plasma composition volumes, such as for example volumes of the plasma composition greater than to about equal to (e.g., 1-2 times, 1-1.5 times) or less than to about equal to (e.g., 0.5-1 times) the subject's plasma volume. For example, in certain embodiments plasma exchange may be achieved with a volume of the plasma composition similar to the subject's plasma volume. Alternatively or in addition, plasma exchange may be achieved with a volume of the plasma composition more than the subject's plasma volume. For example, plasma exchange may be achieved with a volume of the plasma composition about 1 times, about 1.1 times, about 1.2 times, about 1.3 times, about 1.4 times, about 1.5 times, about 1.6 times, about 1.7 times, about 1.8 times, about 1.9 times, or about 2 times the subject's plasma volume. Alternatively or in addition, plasma exchange may be achieved with a volume of the plasma composition less than the subject's plasma volume. For example, plasma exchange may be achieved with a volume of the plasma composition about 0.9 times, about 0.8 times, about 0.7 times, about 0.6 times or about 0.5 times less than the subject's plasma volume. Plasma exchange volumes may also be indicated as volume per patient weight. For example, plasma exchange may be achieved with a volume of the plasma composition comprising about 20 mL/kg, about 25 mL/kg, about 30 mL/kg, about 35 mL/kg, about 40 mL/kg, about 45 mL/kg, about 50 mL/kg, about 55 mL/kg, about 60 mL/kg, about 65 mL/kg, about 70 mL/kg, about 75 mL/kg or about 80 mL/kg patient body weight.

A plasma exchange of the present disclosure may be performed one time or more than one time, for example, the plasma exchange may be performed at least two times, at least three times, at least four times or at least five times or more. In certain embodiments, the plasma exchange is performed 2-5 times. When multiple plasma exchanges (e.g., 2-5 plasma exchanges) are used, the multiple plasma exchanges may be performed within a defined period of time. For example, a plasma exchange may be performed 2-5 times within a period of 4 weeks, within a period or three weeks, within a period of two weeks or within a period of one week. In certain embodiments, five plasma exchanges are performed within a period of 4 weeks, within a period or three weeks, within a period of two weeks or within a period of one week. In certain embodiments, four plasma exchanges are performed within a period of 4 weeks, within a period or three weeks, within a period of two weeks or within a period of one week. In certain embodiments, three plasma exchanges are performed within a period of 4 weeks, within a period or three weeks, within a period of two weeks or within a period of one week. In certain embodiments, two plasma exchanges are performed within a period of 4 weeks, within a period or three weeks, within a period of two weeks or within a period of one week.

Certain aspects of the present disclosure relate to methods of treating a subject suffering from a trauma. In some embodiments, the methods include administering to the subject a therapeutically effective amount of a pathogen-inactivated plasma composition of the present disclosure. For example, in some embodiments, the subject is suffering from burns (including without limitation major burns, e.g., ≥20% of total body surface area), blunt trauma, or penetrating trauma. In some embodiments, the subject is suffering from hemorrhage, e.g., internal hemorrhage.

Certain aspects of the present disclosure relate to methods of treating a subject suffering from burns. In some embodiments, the methods include administering to the subject a therapeutically effective amount of a pathogen-inactivated plasma composition of the present disclosure. For example, in some embodiments, the burns include major burns, e.g., ≥20% of total body surface area.

In some embodiments, the methods include fluid resuscitation. In some embodiments, the methods reduce hemorrhage, hemorrhagic shock, and/or endothelial permeability in the subject. In some embodiments, the methods reduce or prevent traumatic coagulopathy in the subject. In some embodiments, treatment with a method of the present disclosure results in decreased subject mortality (e.g., increased survival rate).

Certain aspects of the present disclosure relate to methods of resuscitation from hemorrhagic shock in a subject suffering from a trauma, e.g., hemorrhagic shock. In some embodiments, the methods include administering to the subject a therapeutically effective amount of a pathogen-inactivated plasma composition of the present disclosure. In some embodiments, the subject is suffering from internal hemorrhage.

Certain aspects of the present disclosure relate to methods of resuscitation suffering from burns. In some embodiments, the methods include administering to the subject a therapeutically effective amount of a pathogen-inactivated plasma composition of the present disclosure. For example, in some embodiments, the burns include major burns, e.g., ≥20% of total body surface area.

In some embodiments, the methods reduce hemorrhage and/or endothelial permeability in the subject. In some embodiments, the methods reduce or prevent trauma-induced endotheliopathy and/or traumatic coagulopathy in the subject. In some embodiments, treatment with a method of the present disclosure results in decreased subject mortality (e.g., increased survival rate).

In some embodiments, a therapeutically effective amount of a pathogen-inactivated plasma composition comprising pathogen-inactivated frozen plasma is administered to a subject. In some embodiments, the pathogen-inactivated plasma composition comprises pathogen-inactivated fresh frozen plasma. In some embodiments, the pathogen-inactivated plasma composition comprises pathogen-inactivated cryo-poor plasma as described herein.

In some embodiments, a pathogen-inactivated plasma composition of the present disclosure is administered after freezing, optional storage, and thawing. For example, in some embodiments, a pathogen-inactivated plasma composition of the present disclosure is administered within 1 day, 2 days, 3 days, 4 days, 5 days, 6 days, or 7 days after thawing (e.g., post-storage thawing as described herein). In other embodiments, the pathogen-inactivated plasma composition is a lyophilized or freeze-dried plasma composition. For example, in some embodiments, a pathogen-inactivated plasma composition of the present disclosure is administered within 1 day, 2 days, 3 days, 4 days, 5 days, 6 days, or 7 days after reconstitution. In some embodiments, a pathogen-inactivated plasma composition of the present disclosure is first administered less than 24 hours after the onset of trauma (e.g., an event which resulted in trauma).

Treatment of trauma in a subject using a pathogen-inactivated plasma composition of the present disclosure may be performed using a variety of volumes. For example, in certain embodiments the volume of the plasma composition administered (e.g., infused) may comprise a volume required to achieve an increase in blood pressure (e.g., systolic blood pressure) to a desired level, such as for example, to at least 50 mmHg, at least 55 mmHg, at least 60 mmHg, at least 65 mmHg, at least 70 mmHg, at least 75 mmHg, at least 80 mmHg, at least 85 mmHg, at least 90 mmHg, at least 95 mmHg, or at least 100 mmHg. In certain embodiments, additional volumes of the plasma composition may be administered to maintain the blood pressure at a desired level, such as any of the aforementioned levels. Alternatively or in addition, the volume of plasma composition administered may comprise the volume required to achieve and/or maintain a palpable pulse (e.g., radial pulse), for example a palpable pulse of a desired strength (e.g., such that it is no longer faint or weak) as determined by medical personnel. In some embodiments, administration of the plasma composition is in conjunction with one or more other medically accepted bleeding control procedures.

Alternatively or in addition, in subjects suffering from burns, such as for example, major burns (e.g., burns ≥20% of total body surface area, TBSA), the volume of a pathogen-inactivated plasma composition administered may be calculated prior to administration, for example, based on the subject's weight and the % TBSA of the burns. For example, the volume of plasma administered may be in a range of about 1-5 mL per kg subject body weight per % burn TBSA (mL/kg/% burn), about 2-5 mL/kg/% burn, about 2-4 mL/kg/% burn, about 2-3 mL/kg/% burn, or about 3-4 mL/kg/% burn, or about 1 mL/kg/% burn, about 2 mL/kg/% burn, about 3 mL/kg/% burn, about 4 mL/kg/% burn, or about 5 mL/kg/% burn.

Alternatively or in addition, the volume of a pathogen-inactivated plasma composition of the present disclosure may be titrated as an amount to maintain renal perfusion to obtain a target urinary output, such as for example about 0.5 ml/kg/hr for adults or about 1 ml/kg/hr for young pediatric patients.

Administration of a pathogen-inactivated plasma composition of the present disclosure may be about 1 hour, about 2 hours, about 3 hours, about 4 hours, about 5 hours, about 6 hours, about 8 hours, about 10 hours, about 12 hours, about 16 hours, about 20 hours, about 24 hours, about 36 hours, about 48 hours, about 72 hours, about 96 hours or about 120 hours after the onset of trauma (e.g., medical diagnosis of trauma, event which resulted in onset of trauma). Alternatively or in addition, administration of a pathogen-inactivated plasma composition may be initiated within (e.g., less than) about 24 hours, within about 20 hours, within about 16 hours, within about 12 hours, within about 10 hours, within about 8 hours, within about 6 hours, within about 5 hours, within about 4 hours, within about 3 hours, within about 2 hours or within about 1 hours after the onset of trauma.

Administration of a desired volume of a pathogen-inactivated plasma composition of the present disclosure may be achieved by administering more than one unit of a pathogen-inactivated plasma composition. For example, at least two, at least three, at least four, at least 5 or more units many be administered to the subject. Administration of the desired volume occur over a desired time period, such as for example, over a period of about 1 hour, about 2 hours, about 3 hours, about 4 hours, about 6 hours, about 8 hours, about 10 hours, about 12 hours, about 16 hours, about 20 hours, or about 24 hours or more. In certain embodiments, administration of a desired volume may be divided between two time periods, such as for example, half of the desired volume within 8 hours of trauma onset and the other half within 24 hours of trauma onset.

In some embodiments, administration of a pathogen-inactivated plasma composition of the present disclosure is followed by administration of at least one additional intravenous fluid. Suitable intravenous fluids are known in the art and can include, without limitation, colloid such as albumin or starch, or crystalloid such as Ringer's lactate or Hartmann solution.

Processing Sets

Certain aspects of the present disclosure relate to processing sets. The processing sets of the present disclosure may find use, inter alia, in preparing a pathogen-inactivated cryoprecipitate, e.g., as described herein.

In some embodiments, a processing set of the present disclosure includes a first container within which a psoralen of the present disclosure can be photoactivated in the presence of one or more units of plasma under sterile conditions (e.g., as described and/or referenced herein). In some embodiments, the processing set further includes a compound absorption device (CAD) coupled to the first container such that the one or more units of plasma can be transferred from the first container to the compound absorption device under sterile conditions. In some embodiments, the processing set further includes one or more second containers. In some embodiments, each of the one or more second containers is coupled to the compound absorption device such that the one or more units of plasma can be transferred from the compound absorption device to the one or more second containers under sterile conditions, e.g., to provide pathogen-inactivated plasma suitable for infusion into a subject. As non-limiting examples, the one or more second containers could include one 600 mL PVC transfer pack or other larger blood bag, or more than one (e.g., three) smaller blood bags (e.g., sized for one AABB unit). In some embodiments, the one or more second containers are suitable for freezing the pathogen-inactivated plasma followed by thawing of the pathogen-inactivated plasma under conditions that provide for the formation of a precipitate and a supernatant.

In some embodiments, a processing set of the present disclosure further includes a third container. In some embodiments, the third container is configured to be coupled to the one or more second containers such that the pathogen-inactivated plasma can be transferred from the one or more second containers to the third container under sterile conditions. In some embodiments, the third container is suitable for freezing the pathogen-inactivated plasma followed by thawing of the pathogen-inactivated plasma under conditions that provide for the formation of a precipitate and a supernatant. In some embodiments, the third container may be e.g., a 600-650 mL bag.

In some embodiments, a processing set of the present disclosure further includes one or more fourth containers. In some embodiments, the one or more fourth containers are configured to be coupled to the one or more second containers as described above or to the third container as described above such that the supernatant can be transferred from the one or more second containers or the third container to the one or more fourth containers under sterile conditions, e.g., to afford a pathogen-inactivated cryosupernatant of the present disclosure contained within the one or more fourth containers and a pathogen-inactivated cryoprecipitate of the present disclosure contained within the one or more second containers or the third container. In some embodiments, the fourth container is suitable for storage of a pathogen-inactivated cryoprecipitate of the present disclosure under conditions in which the pathogen-inactivated cryoprecipitate is frozen. In some embodiments, two or more fourth containers are used. The two or more fourth containers may be configured to be coupled to one another while each of the two or more fourth containers contains pathogen-inactivated cryoprecipitate such that the cryoprecipitate contained within the two or more fourth containers can be combined in one of the two or more fourth containers. In some embodiments, a fourth container may be e.g., a 600-650 mL bag. Non-limiting examples of processing sets of the present disclosure are as follows.

In some embodiments, a processing set includes a first container within which a psoralen can be photoactivated in the presence of one or more units of plasma under sterile conditions; a compound absorption device (CAD) coupled to the first container such that the plasma can be transferred from the first container to the compound absorption device under sterile conditions; one or more second containers, each of which is coupled to the compound absorption device such that the plasma can be transferred from the compound absorption device to the one or more second containers under sterile conditions to provide pathogen-inactivated plasma suitable for infusion into a subject; and a third container, which is configured to be coupled to the one or more second containers such that the pathogen-inactivated plasma can be transferred from the one or more second containers to the third container under sterile conditions. In some embodiments, the one or more second containers are suitable for freezing the pathogen-inactivated plasma followed by thawing of the pathogen-inactivated plasma under conditions that provide for the formation of a precipitate and a supernatant. In some embodiments, the third container is coupled to the one or more second containers such that the supernatant can be transferred from the one or more second containers to the third container under sterile conditions to afford a pathogen-inactivated cryosupernatant contained within the third container and a pathogen-inactivated cryoprecipitate contained within the one or more second containers.

In other embodiments, a processing set includes a first container within which a psoralen can be photoactivated in the presence of one or more units of plasma under sterile conditions; a compound absorption device (CAD) coupled to the first container such that the plasma can be transferred from the first container to the compound absorption device under sterile conditions; one or more second containers, each of which is coupled to the compound absorption device such that the plasma can be transferred from the compound absorption device to the one or more second containers under sterile conditions to provide pathogen-inactivated plasma suitable for infusion into a subject; a third container, which is configured to be coupled to the one or more second containers such that the pathogen-inactivated plasma can be transferred from the one or more second containers to the third container under sterile conditions; and one or more fourth containers, each of which is configured to be coupled to the third container such that the supernatant can be transferred from the third container to the one or more fourth containers under sterile conditions to afford a pathogen-inactivated cryosupernatant contained within the one or more fourth containers and a pathogen-inactivated cryoprecipitate contained within the third container. In some embodiments, the third container is suitable for freezing the pathogen-inactivated plasma followed by thawing of the pathogen-inactivated plasma under conditions that provide for the formation of a precipitate and a supernatant.

Further non-limiting examples of processing sets are illustrated in FIGS. 1A-3B. Exemplary processing set 100 shown in FIG. 1A includes optional plasma bag 102 containing the donor plasma to be pathogen inactivated, container 104 that contains a pathogen inactivation compound (PIC, e.g., a psoralen), and bag 106 for photoactivation of the plasma (e.g., a first container of the present disclosure). Photoactivation bag 106 is coupled to CAD 108 through tubing 110, which allows for the transfer of plasma after photoactivation to the CAD. CAD 108 in turn is coupled to three smaller blood bags 112, 114, and 116 (e.g., second containers of the present disclosure) through tubing 118, which allows the plasma to pass through the CAD (e.g., to remove free photoproducts and/or unreacted pathogen inactivation compound) before being collected in the smaller blood bags. Optional larger bag 122 for freezing the plasma to form cryoprecipitate (e.g., a third container of the present disclosure) and optional larger bag 124 for separating the cryoprecipitate from the cryosupernatant (e.g., a fourth container of the present disclosure), which may be sterile docked (e.g., using sterile connect 126) to the tubing between the CAD 108 and the three-way lead 120 of tubing 118 after collection of the PI plasma in the three bags, are also depicted.

Figure 1B:
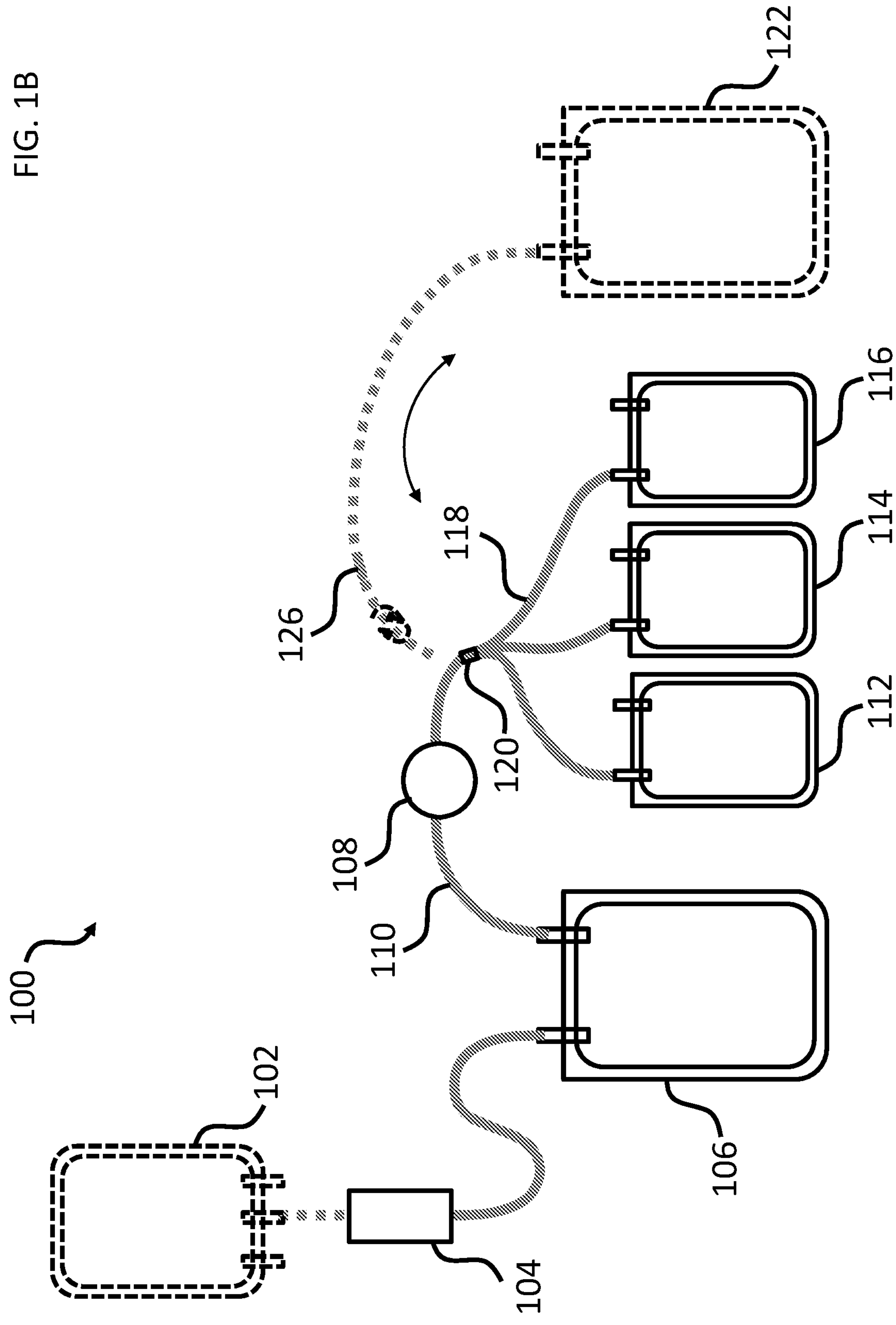
FIG. 1B shows an exemplary processing kit in accordance with some embodiments. Dotted components are optional.

An alternative configuration for processing set 100 is shown in FIG. 1B, where the cryoprecipitate is separated from the cryosupernatant by flowing the cryosupernatant from sterile-docked third container 122 back into the three smaller bags 112, 114, and 116 (e.g., second containers of the present disclosure), rather than into the optional fourth container 124.

In other embodiments, the cryoprecipitate is separated from the cryosupernatant by flowing the cryosupernatant from sterile-docked third container 122 back into smaller bags 112 and 114. The cryoprecipitate in 122 may then be resuspended in a small volume of cryo-poor plasma supernatant (e.g., about 100 mL) and transferred to smaller bag 116, resulting in two smaller bags 112 and 114 containing cryo-poor plasma (CPP) and smaller bag 116 containing resuspended cryoprecipitate.

Figure 1C:
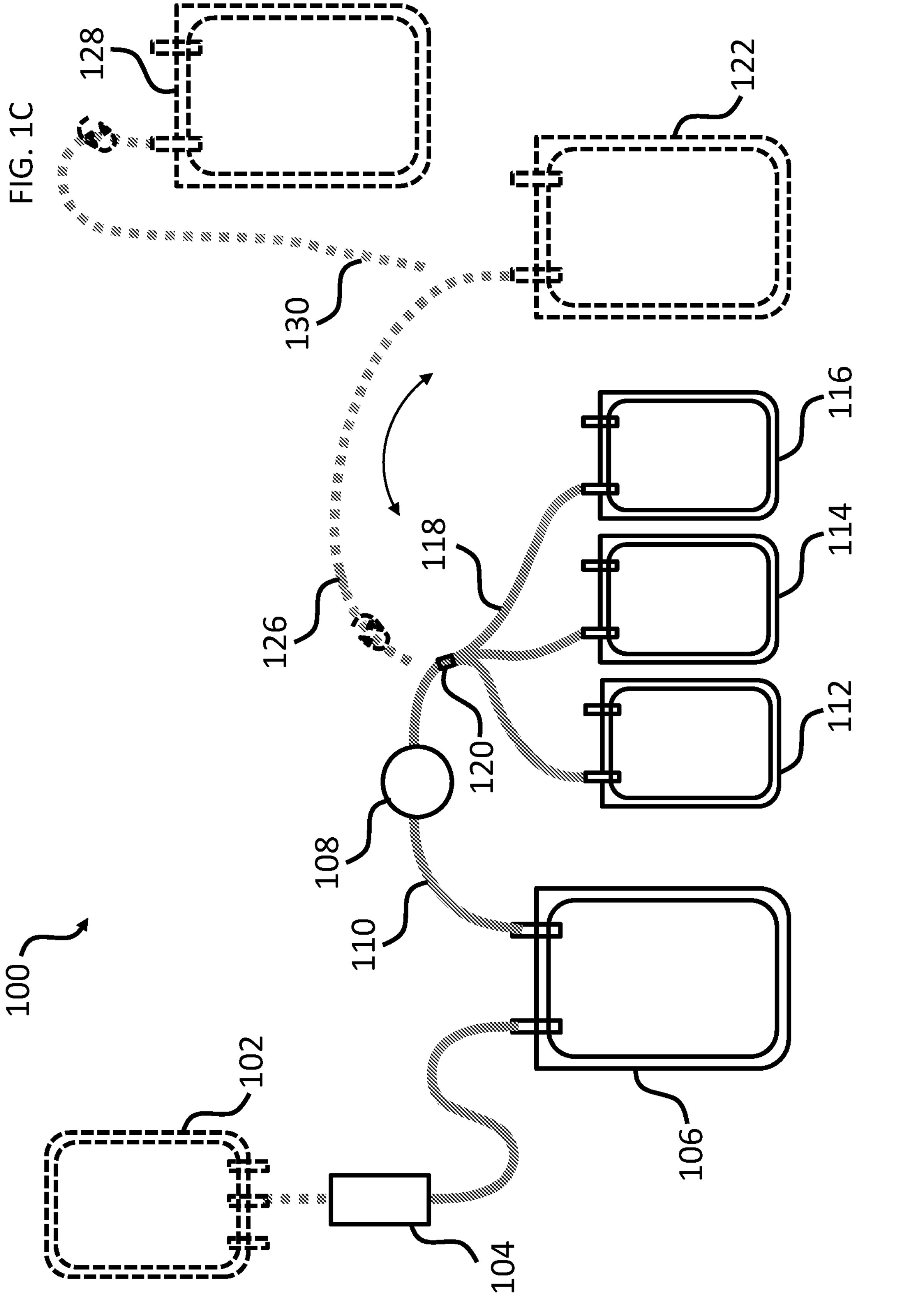
FIG. 1C shows an exemplary processing kit in accordance with some embodiments. Dotted components are optional.

Another alternative configuration for processing set 100 is shown in FIG. 1C. This configuration includes optional container 128 that is sterile connected or docked with third container 122 through sterile connect 130. This configuration allows two cryosupernatant preparations made from pathogen-inactivated plasma (e.g., prepared in 122 and 128) to be combined.

Figure 2A:
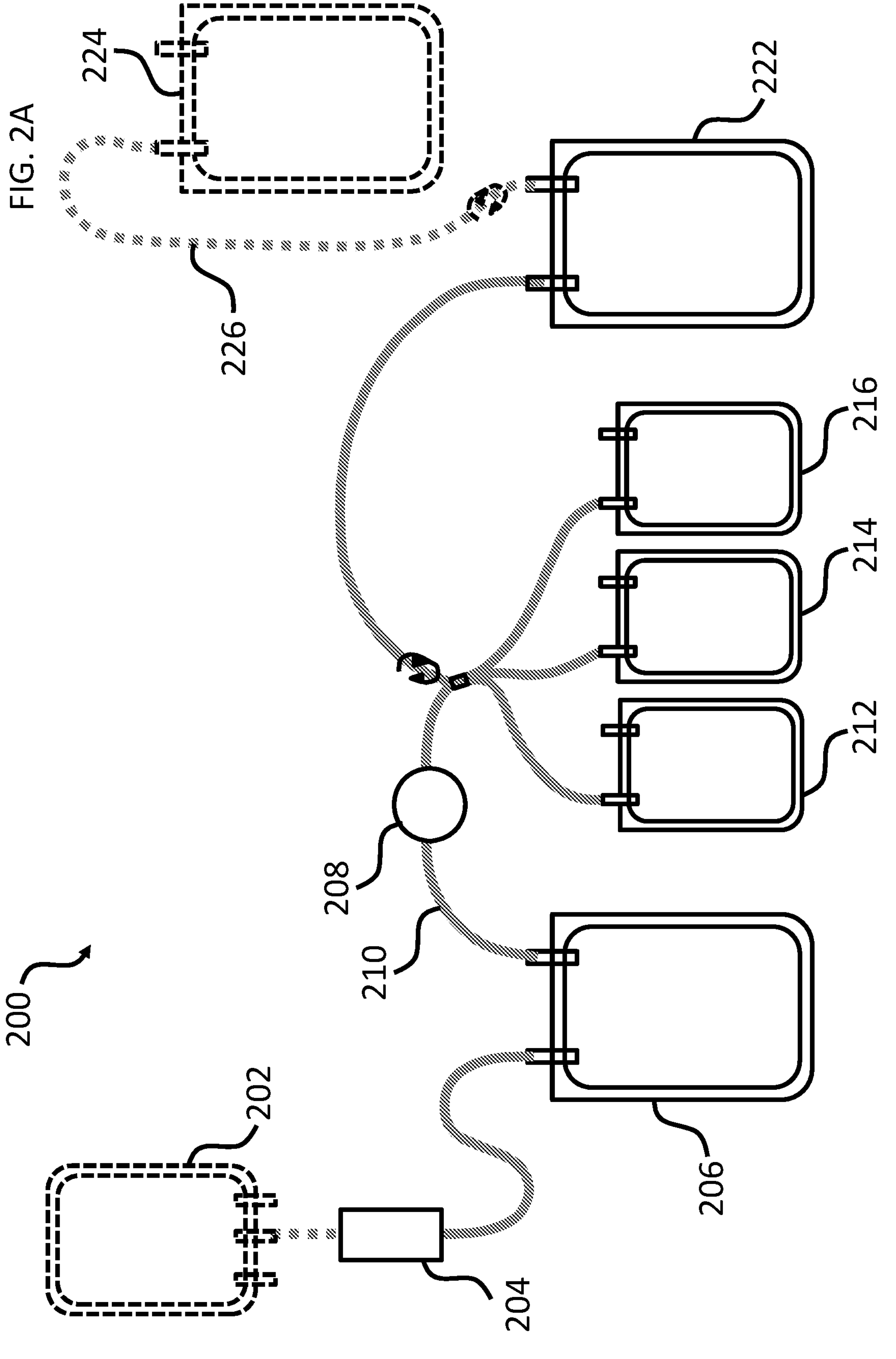
FIG. 2A shows an exemplary processing kit in accordance with some embodiments. Dotted components are optional.
Figure 2B:
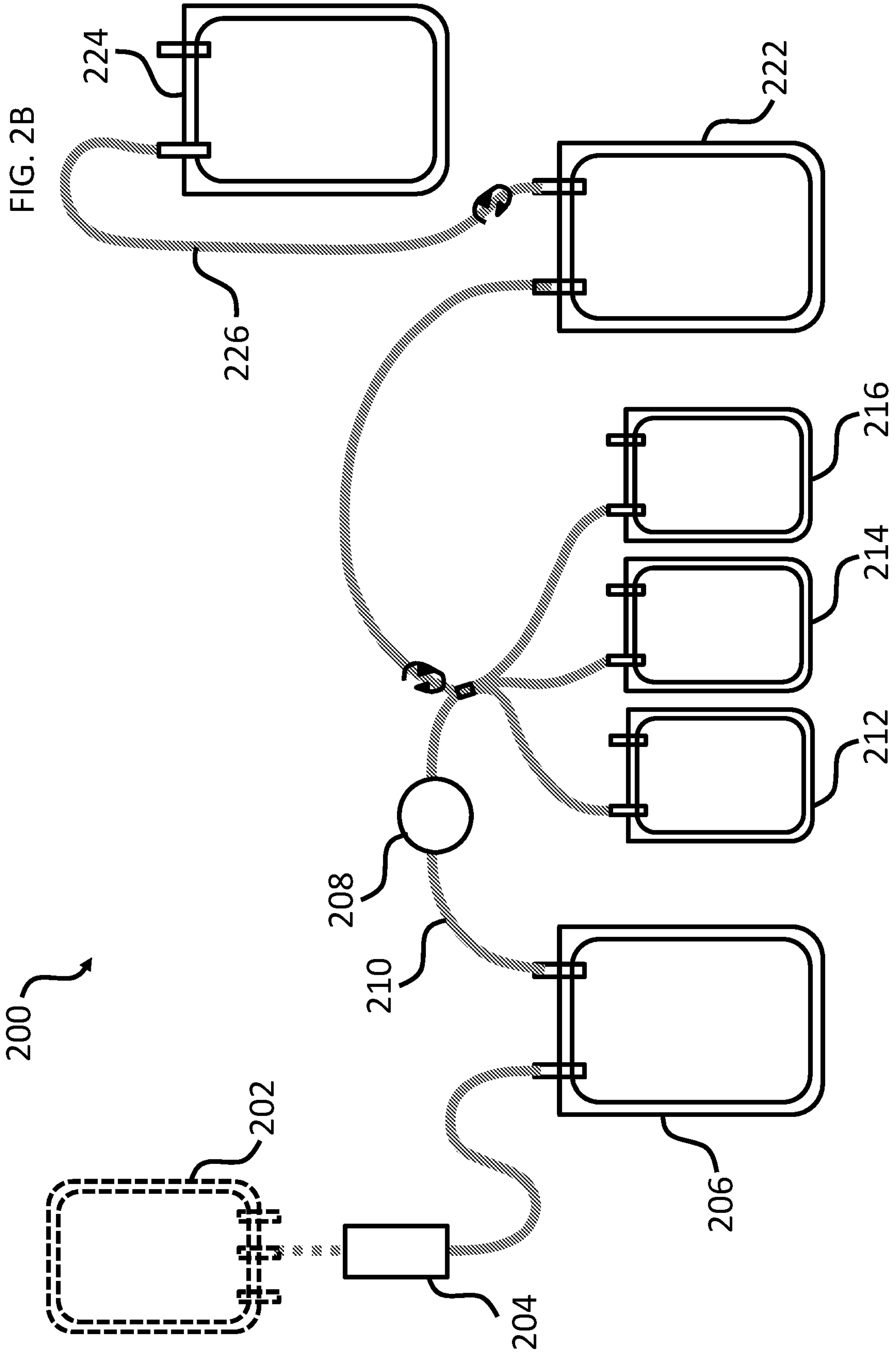
FIG. 2B shows an exemplary processing kit in accordance with some embodiments. Dotted components are optional.
Figure 2C:
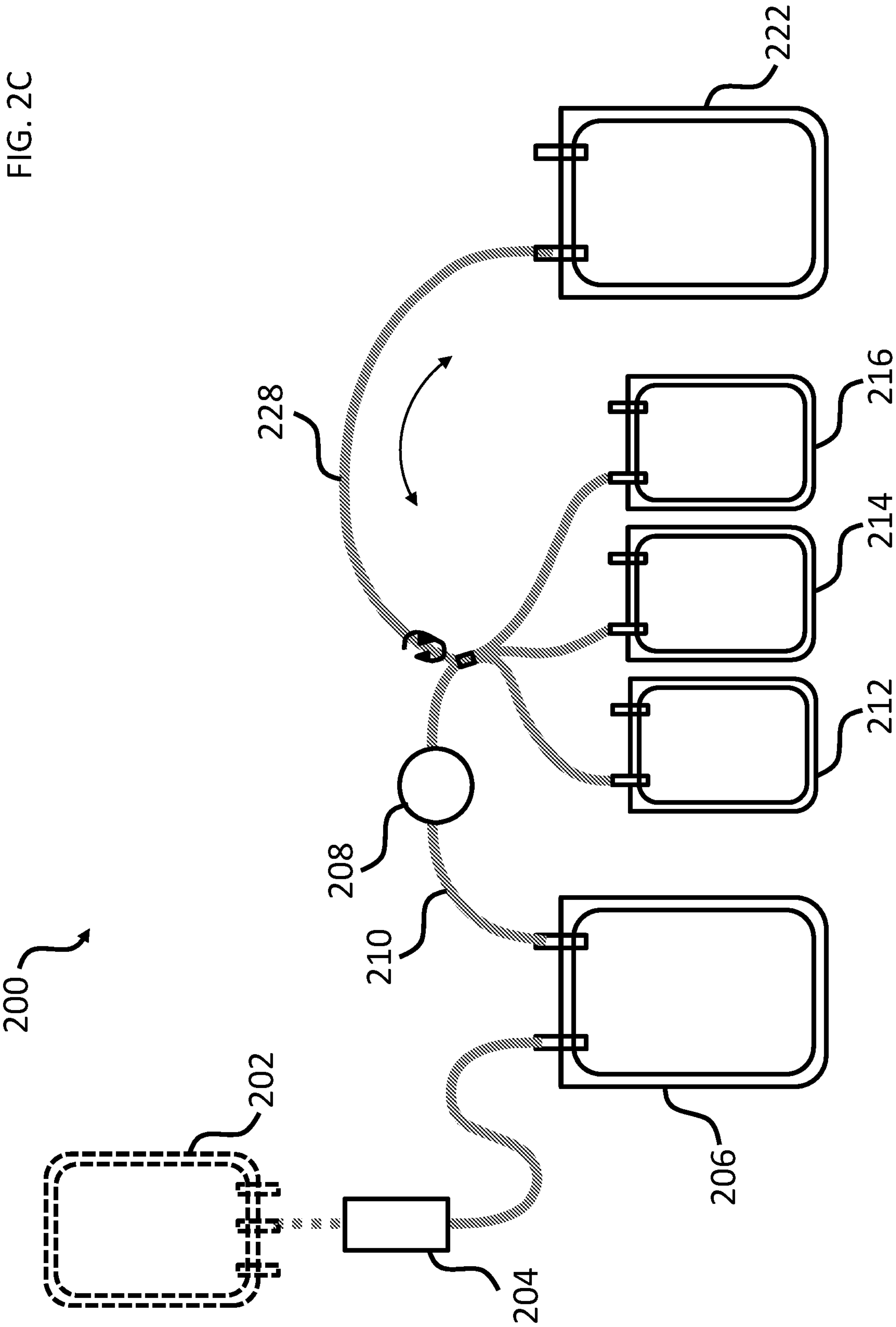
FIG. 2C shows an exemplary processing kit in accordance with some embodiments. Dotted components are optional.

The exemplary processing set 200 shown in FIG. 2A, includes optional plasma bag 202 containing the donor plasma to be pathogen inactivated, container 204 that contains a pathogen inactivation compound (PIC), photoactivation bag 206, and CAD 208 coupled to photoactivation bag 206 with tubing 210 as described above, and additionally a pre-attached (e.g., integrated) third container 222. After collection of the pathogen-inactivated plasma in the three bags 212, 214, and 216, the three units of PI plasma are pooled by transferring into larger bag 222 (e.g., a third container of the present disclosure) for freezing to form cryoprecipitate and for separating cryoprecipitate from the cryosupernatant. As shown in FIG. 2B, cryosupernatant bag 224 (e.g., a fourth container of the present disclosure) may be used to collect the cryosupernatant after freezing (this is depicted as an optional component in FIG. 2A). This cryosupernatant bag may be connected to the larger freezing bag via tubing with common tubing clamp 226. An alternative configuration is shown in FIG. 2C, where the cryoprecipitate is separated from the cryosupernatant by flowing the cryosupernatant back into the three smaller bags 212, 214, and 216 (e.g., second containers of the present disclosure) using tubing 228, rather than into the fourth container 224 shown in FIG. 2B.

Figure 3A:
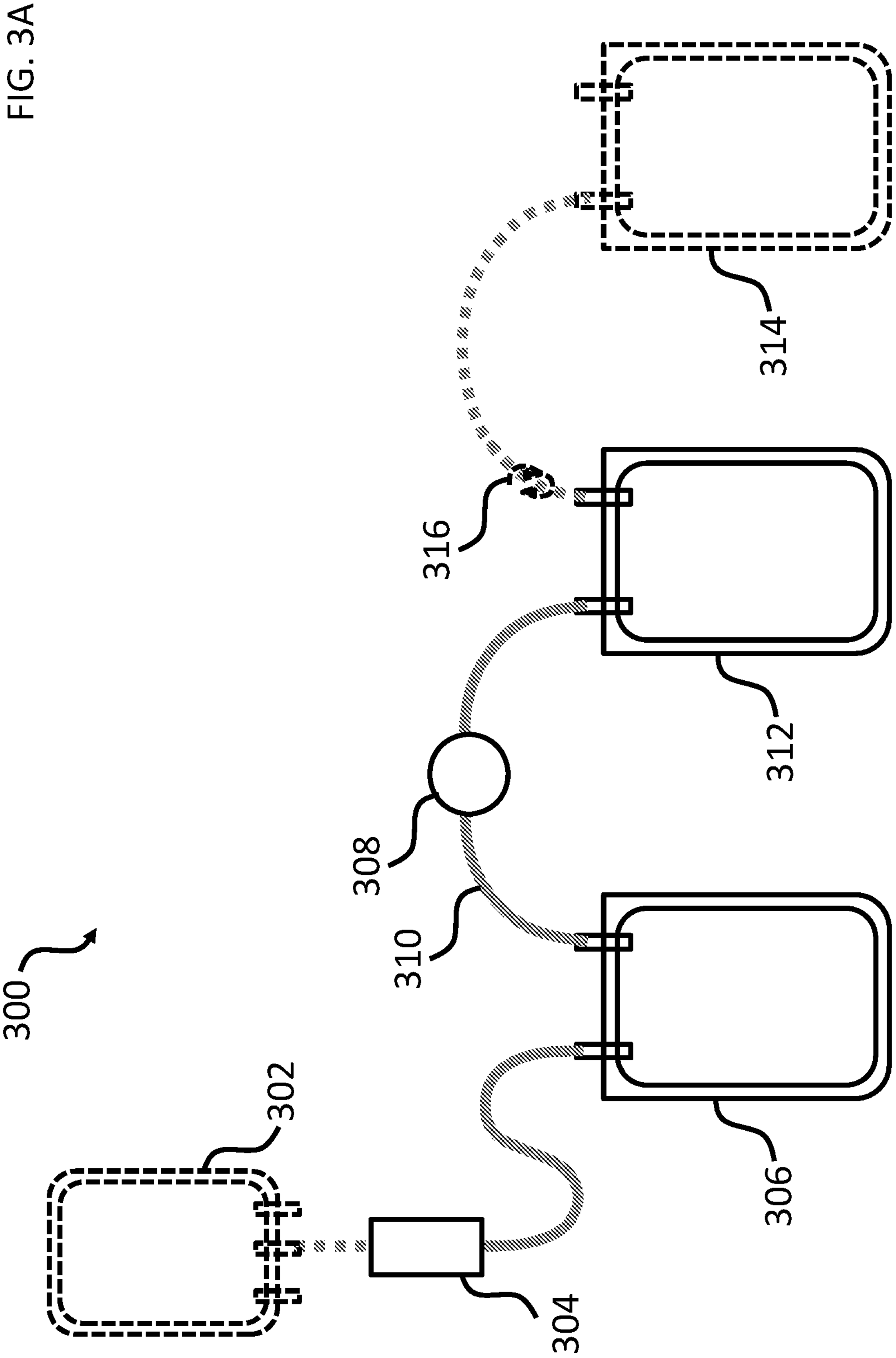
FIG. 3A shows an exemplary processing kit in accordance with some embodiments. Dotted components are optional.
Figure 3B:
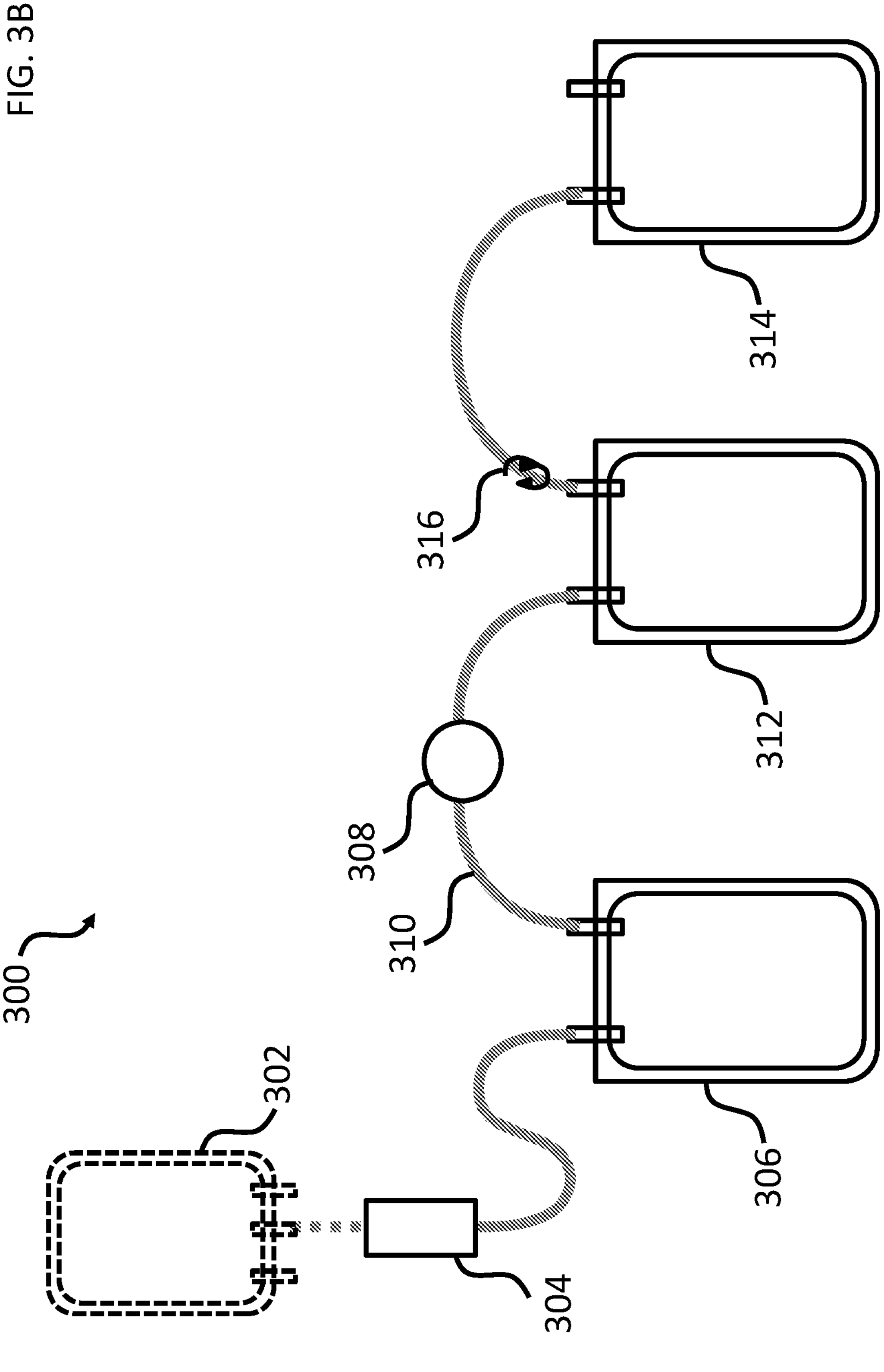
FIG. 3B shows an exemplary processing kit in accordance with some embodiments. Dotted components are optional.

The exemplary processing set 300 shown in FIG. 3A includes optional plasma bag 302 containing the donor plasma to be pathogen inactivated, container 304 that contains a pathogen inactivation compound (PIC), photoactivation bag 306, and CAD 308 coupled to photoactivation bag 306 with tubing 310 as described above. However, in this example, a single, larger (e.g., 800 mL) bag 312 (e.g., a third container of the present disclosure) replaces the three smaller bags (e.g., 212, 214, and 216). This bag 312 may be used for pathogen-inactivated plasma collection after photoactivation, as well as freezing/thawing for production of cryoprecipitate. The optional bag for cryosupernatant (e.g., 314) also depicted could be a pre-attached (e.g., integrated) part of the set with clamp 316 or alternatively sterile docked after PI plasma collection. In FIG. 3B, this cryosupernatant bag 314 (e.g., a fourth container of the present disclosure) is an integral part of set 300 coupled to the cryoprecipitate bag 312 (e.g., via tubing and a tubing clamp 316) and used to collect the cryosupernatant.

In any of the processing sets of the present disclosure, the first container (e.g., 106, 206, and/or 306) and the CAD (e.g., 108, 208, and/or 308) may be separated in a sterile manner from the rest of the components, such as the PI plasma and cryoprecipitate containers (e.g., 112, 114, 116, 212, 214, 216, and/or 312), e.g., before freezing.

Figure 4:
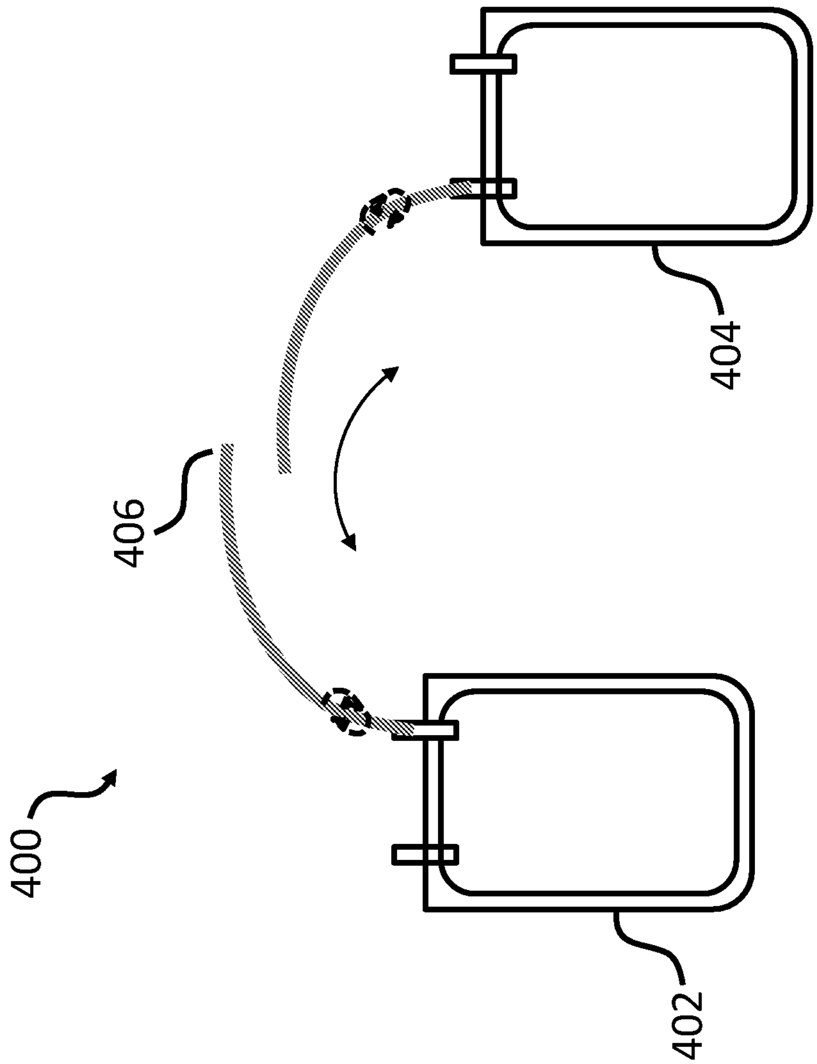
FIG. 4 depicts combining two separate cryoprecipitate preparations in accordance with some embodiments.

As described herein, in some embodiments, two or more cryoprecipitate preparations of the present disclosure can be combined or pooled. Exemplary technique 400 for this pooling is shown in FIG. 4. Containers 402 and 404 contain a first and a second cryoprecipitate preparation, respectively. They are combined in FIG. 4 by sterile docking, e.g., using sterile connect 406. The technique illustrated in FIG. 4 may be applied to any of the cryoprecipitate preparations described herein, e.g., the cryoprecipitate preparations made from pathogen-inactivated plasma contained in containers 122, 222, and/or 312.

Figure 5:
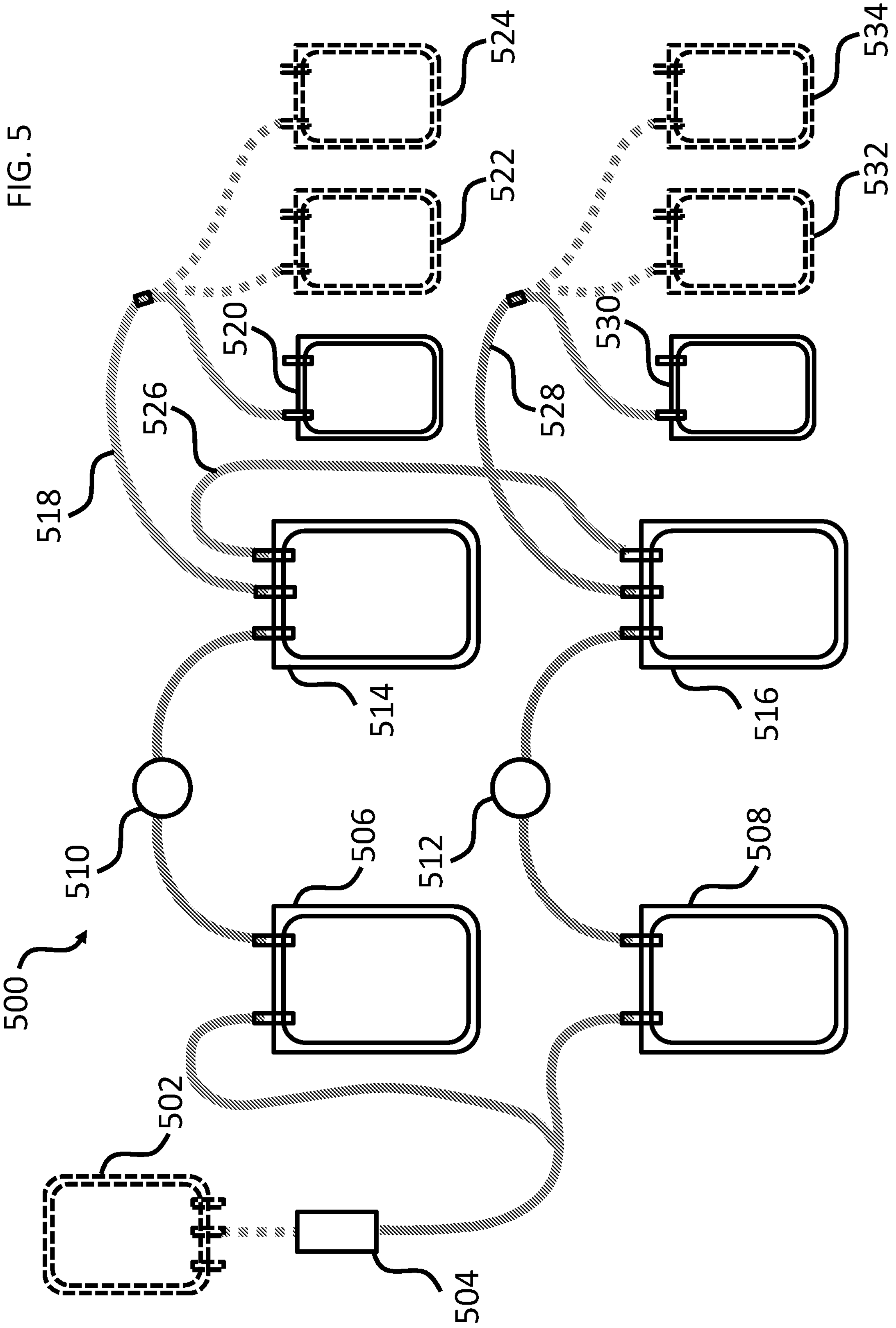
FIG. 5 shows an exemplary processing kit in accordance with some embodiments. Dotted components are optional.

Exemplary processing set 500 is shown in FIG. 5. Integrated processing set 500 allows for the production and combining or pooling of two larger cryoprecipitate preparations, e.g., as described herein. Processing set 500 includes one or more optional plasma containers (e.g., as shown by optional plasma container 502). Container(s) 502 is coupled to container 504, which contains a pathogen inactivation compound (PIC). Pathogen-inactivated plasma is then split into first and second photoactivation bags 506 and 508 (respectively), which in turn are coupled to first and second CADs 510 and 512 (respectively). CADs 510 and 512 are then coupled to first and second bags 514 and 516 (respectively), which are used for pathogen-inactivated plasma collection after photoactivation, as well as freezing/thawing for production of cryoprecipitate. For example, in some embodiments, 514 and/or 516 are larger (e.g., 800 mL) bags (e.g., third containers of the present disclosure), similar to bag 312 described above. Bag 514 is connected (e.g., through tubing 518) to cryosupernatant bags 520, 522, and 524 (e.g., fourth containers of the present disclosure) for collection of cryo-poor plasma. Similarly, bag 516 is connected (e.g., through tubing 528) to cryosupernatant bags 530, 532, and 534 (e.g., fourth containers of the present disclosure) for collection of cryo-poor plasma. In some embodiments, bags 514 and 516 are themselves connected via tubing 526, e.g., to allow the pathogen-inactivated cryoprecipitate preparations contained therein to be combined or pooled.

Figure 6:
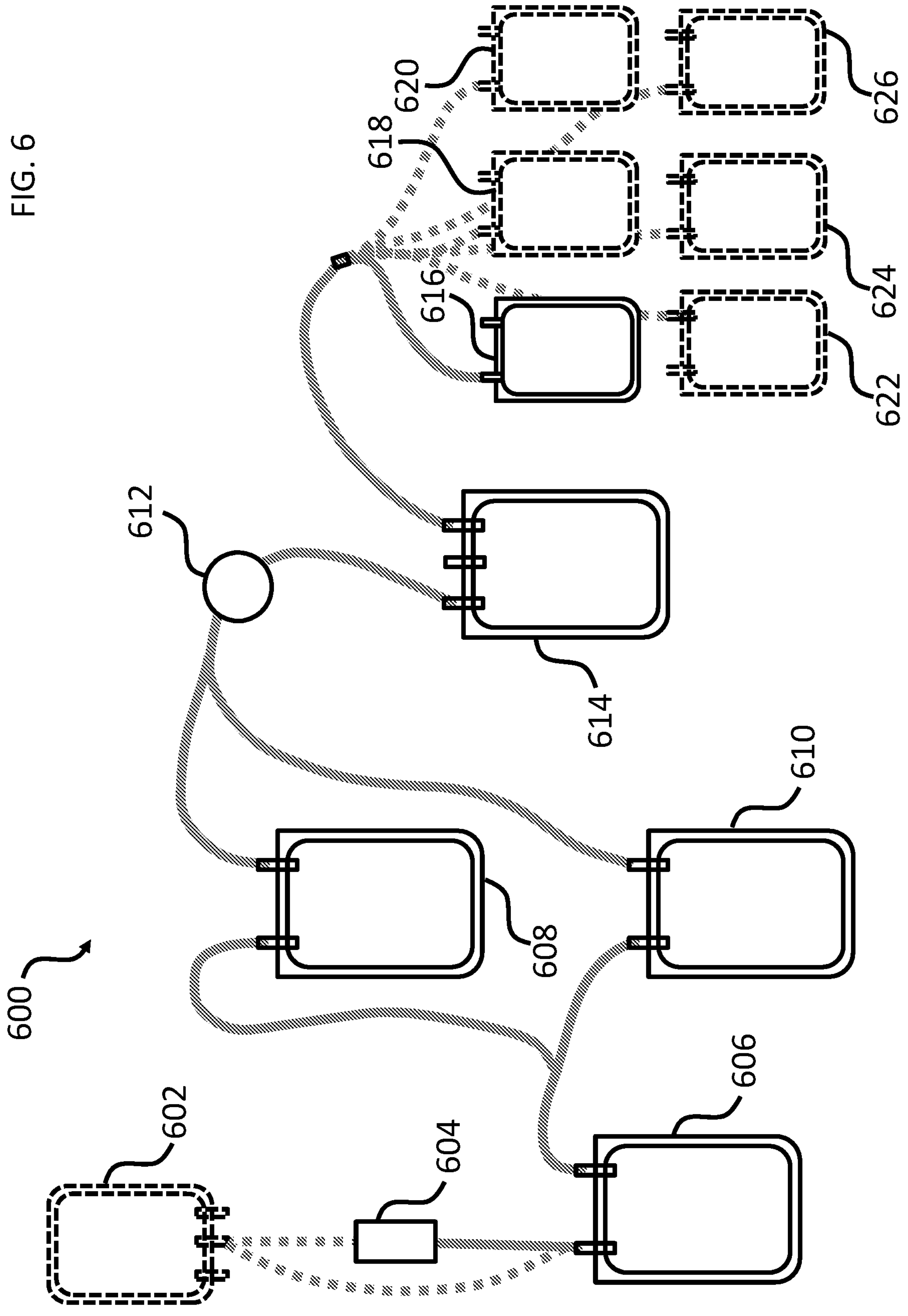
FIG. 6 shows an exemplary processing kit in accordance with some embodiments. Dotted components are optional.

Exemplary processing set 600 is shown in FIG. 6. Integrated processing set 600 represents another configuration that allows for the production and combining or pooling of two larger cryoprecipitate preparations, e.g., as described herein. Processing set 600 includes one or more optional plasma containers (e.g., as shown by optional plasma container 602). Container(s) 602 is coupled to container 604, which contains a pathogen inactivation compound (PIC). Container 604 is then coupled to mixing container 606, which is used to contain the plasma/PIC mixture (optionally, as depicted in FIG. 6, container 602 may be coupled directly to mixing container 606 without 604 as an intermediary). The plasma/PIC mixture is then split into first and second photoactivation bags 608 and 610 (respectively). After photoactivation, the split plasma/PIC mixtures are then passed through CAD 612 and into bag 614, which is used for pathogen-inactivated plasma collection after photoactivation, as well as freezing/thawing for production of cryoprecipitate. In some embodiments, bag 614 is a larger (e.g., 800 mL) bag (e.g., a third container of the present disclosure), similar to bag 312 described above. One or more cryosupernatant bags (e.g., bags 616, 618, 620, 622, 624, and 626) are connected to bag 614 for collection of cryo-poor plasma.

It is to be understood that any of the processing sets of the present disclosure may be used in any of the methods of the present disclosure, or used to contain and/or process any of the plasma compositions, including for example the cryoprecipitates, cryoprecipitate compositions, and/or cryo-poor plasmas (cryosupernatants) of the present disclosure.

The disclosure is illustrated further by the following examples, which are not to be construed as limiting the disclosure in scope or spirit to the specific procedures described in them.

EXAMPLES

Example 1: Preparation of Pathogen Inactivated Cryoprecipitate and Cryo-Poor Plasma Multiple blood group O negative units of liquid plasma units from the day of draw were pooled and split to obtain multiple plasma units for processing, each with a final volume 585 to 650 mL. Pathogen inactivation and preparation of cryoprecipitate and cryo-poor plasma was undertaken with the pooled plasma units. The plasma was subjected to photochemical pathogen inactivation using the commercially available INTERCEPT Blood System for Plasma (Cerus Corporation). In the case of four of the pooled units subjected to INTERCEPT treatment, the pathogen inactivated plasma collected in the 3 storage bags of the INTERCEPT processing set (see e.g., 112, 114, and 116 in FIG. 1B) was transferred to a sterile-docked (sterile-connected), single 1000 mL transfer bag (see e.g., 122 in FIG. 1B) as large volume unit preparations. Two other of the pooled units subjected to INTERCEPT treatment were maintained in the 3 storage bags as smaller volume individual “single unit” preparations. The pathogen inactivated plasma units were then frozen at −30° C. for use in the preparation of cryoprecipitate and cryo-poor plasma.

For preparing cryoprecipitate and cryo-poor plasma, units were thawed in a temperature controlled 4° C. water bath, with a total thaw time of approximately 6 hr 30 minute for the large cryo units and 4 hr 30 min for the single cryo units. The thawed units were centrifuged for 12 minutes at 4° C. at 4200 rcf, with a slow deceleration. The cryo-poor supernatants were removed from the cryoprecipitates by transferring out of the 1000 mL transfer bag, while maintaining a small amount of plasma for re-suspension of the cryoprecipitates. Following resuspension, the cryoprecipitate units were frozen for storage at −30° C.

The frozen, stored cryoprecipitate units were thawed in a Helmer plasma thawer set at 35° C., with the cryoprecipitate full dissolved with no visible particulate matter. Thawed units were stored in a temperature controlled cabinet at 22° C., with samples removed at defined intervals of <2 hr, 6 hr, 24 hr and 5 days for analytical testing. Samples were tested for Factor VIII (FVIII) and Fibrinogen (FIB), with resulting data in Table 1.

TABLE 1

Fibrinogen and Factor VIII in cryoprecipitate preparations.

| | 2 hr | 6 hr | 24 hr | 5 days |
|---|---|---|---|---|
| Large volume (n = 4), 60.2 ± 4.9 mL | | | | |
| Cryo FIB (mg) | 492.7 ± 70.7 | 498.7 ± 74.0 | 501.3 ± 61.46 | 482.9 ± 74.8 |
| Cryo FIB (mg/unit*) | 181.2 ± 24.3 | 183.5 ± 26.6 | 184.4 ± 21.22 | 177.6 ± 26.7 |
| Cryo FVIII (IU) | 182.6 ± 37.9 | 176.3 ± 26.9 | 177.6 ± 73.4 | 145.7 ± 37.5 |
| Cryo FVIII (IU/unit*) | 67.2 ± 13.7 | 64.9 ± 9.6 | 65.2 ± 26.6 | 53.6 ± 13.5 |

TABLE 1-continued

Fibrinogen and Factor VIII in cryoprecipitate preparations.

| | 2 hr | 6 hr | 24 hr | 5 days |
|---|---|---|---|---|
| Single unit (n = 2), 24.1 ± 11.5 mL | | | | |
| Cryo FIB (mg) | 315.4 ± 49.1 | 315.5 ± 38.8 | 301.2 ± 35.4 | 274.2 ± 55.3 |
| Cryo FIB (mg/unit*) | 192.6 ± 4.2 | 183.5 ± 26.6 | 184.4 ± 3.1 | 167.0 ± 11.4 |
| Cryo FVIII (IU) | 94.5 ± 32.5 | 89.2 ± 40.0 | 82.4 ± 33.0 | 69.3 ± 40.0 |
| Cryo FVIII (IU/unit*) | 57.0 ± 12.2 | 53.4 ± 17.3 | 49.5 ± 13.5 | 41.1 ± 19.0 |

*Based on AABB unit volume of 200 mL

Example 2: Preparation of Pathogen Inactivated Cryoprecipitate and Cryo-Poor Plasma Multiple plasma units obtained from blood group A donors were pooled to obtain plasma preparations with volumes of about 650 mL each (e.g., large volume). Pathogen inactivation and preparation of cryoprecipitate and cryo-poor plasma was undertaken with the pooled plasma units. The plasma was subjected to photochemical pathogen inactivation using the commercially available INTERCEPT Blood System for Plasma (Cerus Corporation), to yield three individual pathogen-inactivated plasma (PI plasma) units from each pool. The three PI plasma units (3 containers, see e.g., 112, 114, and 116 in FIG. 1B) generated from each INTERCEPT processing set were combined by transferring into a sterile-docked, single 600 mL transfer bag (see e.g., 122 in FIG. 1B) and frozen at −30° C. for use in the preparation of cryoprecipitate and cryo-poor plasma.

For preparing cryoprecipitate and cryo-poor plasma, pooled units were thawed in a temperature controlled 4° C. water bath, with a total thaw time of approximately 6 hr 15 minutes. The thawed units were centrifuged for 12 minutes at 4° C. at 4200 rcf, with a slow deceleration. The cryo-poor plasma supernatants were removed from the cryoprecipitates by transfer into the three previous containers, 60 mL of the plasma (i.e., cryo-poor plasma) added back to the cryoprecipitate for re-suspension, and the cryoprecipitate units were frozen for storage at −30° C.

The frozen, stored cryoprecipitate units were thawed in a Helmer plasma thawing system at 37° C., with the cryoprecipitate fully dissolved with no visible particulate matter. Thawed units were stored in a temperature controlled cabinet at 22° C., with samples removed at defined intervals at least through day 5 post-thaw for analytical testing of Factor VIII (FVIII) and Fibrinogen (FIB), with resulting data in Table 2:

TABLE 2

Fibrinogen and Factor VIII in cryoprecipitate preparations.

| | <2 hr | 6 hr | 24 hr | 48 hr |
|---|---|---|---|---|
| Cryo FIB (mg) | | | | |
| Cryo prep 1 | 960.5 | 926.5 | 942.0 | 937.8 |
| Cryo prep 2 | 661.4 | 676.0 | 670.0 | 683.3 |
| Cryo FVIII (IU) | | | | |
| Cryo prep 1 | 273.8 | 277.6 | 277.9 | 188.1 |
| Cryo prep 2 | 252.9 | 260.8 | 248.9 | 174.2 |

Example 3: Preparation of PI Cryoprecipitate and Cryo-Poor Plasma

Pathogen inactivated (PI) cryoprecipitate and cryo-poor plasma supernatant were prepared as three large volume (647±2 mL) input pools of 2-3 units of ABO matched whole blood derived plasma in CPD anticoagulant within 8 hr of draw.

The pooled plasma was subjected to photochemical pathogen inactivation using amotosalen and UVA, with the commercially available INTERCEPT Blood System for Plasma. Baseline samples were collected prior to INTERCEPT treatment, and pathogen inactivation was performed according to the manufacturer's package insert. The three PI plasma units (3 containers, see e.g., 112, 114, and 116 in FIG. 1B) generated from each INTERCEPT processing set were combined by sealing above the connection, sterilely connecting a 600 mL transfer bag (see e.g., 122 in FIG. 1B), and transferring by gravity flow. After sampling, pathogen inactivated plasma preparations were subjected to rapid freezing and stored at −30° C. for use in the preparation of cryoprecipitate.

For preparing cryoprecipitate, the frozen plasma was thawed in a 4° C. water bath within approximately 12 hr, and centrifuged at 4,000×g for 12 min to sediment the cryoprecipitate. The cryo-poor plasma was removed using a plasma expressor and transferred back into the three plasma bags of the INTERCEPT processing set, leaving approximately 60 mL of the plasma (i.e., cryo-poor plasma) for resuspension of the cryoprecipitate. The cryoprecipitate bag and CPP bags were separated and sealed using a tubing sealer, and frozen at −30° C. for storage.

For characterization, the frozen cryoprecipitate and cryo-supernatants were thawed at 37° C. in a QuickThaw™ Plasma Thawing System (Helmer, Noblesville, Ind.) and held at room temperature (22° C., 2 units) or refrigerated (4° C., 1 unit) for sterile sampling at times 0 hr, 6 hr, 24 hr, day 3 and day 5 post-thaw for analytical testing. In vitro assays for cryoprecipitate and cryo-poor plasma supernatant characterization included total fibrinogen and Factor VIII, as measured on diluted samples, using an AMAX coagulation analyzer. Table 3 includes total fibrinogen and Factor FVIII content for each of the three cryoprecipitate preparations.

TABLE 3

Fibrinogen and Factor VIII in cryoprecipitate preparations.

| | 0 hr | 6 hr | 24 hr | D3 | D5 |
|---|---|---|---|---|---|
| Cryo FIB (mg) | | | | | |
| Cryo prep 1 (22° C.) | 901 | 857 | 887 | ND | 887 |
| Cryo prep 2 (22° C.) | 788 | 908 | ND | 771 | 995 |
| Cryo prep 3 (4° C.) | 772 | 896 | 969 | ND | 907 |
| Cryo FVIII (IU) | | | | | |
| Cryo prep 1 (22° C.) | 278 | 319 | 280 | ND | 286 |
| Cryo prep 2 (22° C.) | 319 | 347 | ND | 268 | 229 |
| Cryo prep 3 (4° C.) | 316 | 307 | 322 | ND | 218 |

ND: not determined.

Fibrinogen and Factor VIII were also determined for the cryo-poor plasma by the same method. At time 0 hr, fibrinogen content was 772 mg, 746 mg and 736 mg total for preps 1, 2 and 3, respectively. Also, at time 0 hr, FVIII content was 54, 46 and 70 IU total for preps 1, 2 and 3, respectively. Thrombin generation activity was also determined by standard methodologies and found to be at high levels.

Example 4: Preparation of PI Cryoprecipitate and Cryo-Poor Plasma

Pathogen inactivated (PI) cryoprecipitate and cryo-poor plasma supernatant were prepared as large volume (585 to 650 mL) input of whole blood derived FFP, whole blood derived PF24 or apheresis plasma (apheresis FFP) obtained from blood group A, B and/or O donors. Six replicates were prepared from pools of 5 to 6 iso-group units of whole blood derived plasma collected in CP2D anticoagulant to yield approximately 1700 mL. The pooled plasma was split into two components (target 625 mL+25 mL, FFP and PF24) and stored at room temperature for up to 8 hr (FFP) or 24 hr (PF24) prior to subjecting the plasma to photochemical pathogen inactivation using the commercially available INTERCEPT Blood System, and freezing. Two units were maintained as untreated controls without pathogen inactivation (target 215-235 mL, FFP and PF24). Additionally, six replicates of apheresis plasma were collected in ACD anticoagulant from a maximum of two iso-group donors and split into two components: one (target 625+25 mL) which was stored at room temperature for up to 8 hr prior to subjecting the plasma to pathogen inactivation and freezing, and the other maintained as untreated control. Baseline samples were collected prior to INTERCEPT treatment, and pathogen inactivation was performed according to the manufacturer's package insert. The three PI plasma units (3 containers, see e.g., 112, 114, and 116 in FIG. 1B) generated from each INTERCEPT processing set were combined by transferring into a sterile-connected, single 800 mL transfer bag (Terumo) (see e.g., 122 in FIG. 1B) and frozen for use in the preparation of cryoprecipitate. Controls were frozen without pathogen inactivation treatment.

For preparing cryoprecipitate, the combined frozen plasma was thawed in a temperature controlled 2-6° C. refrigerator, with a total thaw time of approximately 24 hr. The thawed plasma was centrifuged to sediment the cryoprecipitate, and the cryo-poor plasma supernatants were removed from the cryoprecipitate using a plasma expressor and transferred into the three previous containers, leaving sufficient plasma (i.e., the cryo-poor plasma) to result in about 60 mL of resuspended cryoprecipitate, the cryoprecipitate bag then was separated from the three cryo-poor plasma bags using a tube sealer, and the cryoprecipitate and CPP units frozen for storage.

For characterization, the frozen cryoprecipitate and CPP cryosupernatants were thawed at 37° C. in a QuickThaw™ Plasma Thawing System (Helmer, Noblesville, Ind.) and held at room temperature (20-24° C.) for sterile sampling at times 0, 24 and 120 hours post-thaw for analytical testing. In vitro assays for cryoprecipitate and/or CPP cryosupernatant include a panel of coagulation parameters (e.g., PT, aPTT, thrombin generation), coagulation factors and hemostatic system proteins (e.g., fibrinogen, Factors II, V, VII, VIII (VIII:C), IX, X, XI, XIII, vWF, ADAMTS-13), and other proteins and markers and/or function (e.g., antithrombin III, Protein C, Protein S, Alpha-2-PI, thrombin-antithrombin complexes, Factor VIIa, NAPTT, C3a, Ig's, ROTEM).

Analysis of FVIII, FXIII and fibrinogen was performed using an AMAX Destiny Plus coagulation analyzer and Stago Diagnostic reagents. The following Tables 4 and 5 include total fibrinogen and FVIII at times 0, 24 and 120 hours post-thaw for containers of cryoprecipitate product prepared from whole blood derived FFP, whole blood derived PF24 and apheresis derived FFP, with ABO blood types as listed, and support an extended post-thaw expiry for cryoprecipitate as disclosed herein.

TABLE 4

Total fibrinogen content (mg) after post-thaw storage.

| Plasma Unit | | t = 0 | t = 24 hr | t = 120 hr |
|---|---|---|---|---|
| WBD FFP Group O | Average | 758 | 786 | 793 |
| | SD | 192.4 | 229.8 | 183.8 |
| WBD FFP Group A | Average | 767 | 827 | 794 |
| | SD | 91.0 | 52.7 | 81.6 |
| WBD FFP All groups | Average | 762 | 806 | 794 |
| | SD | 134.7 | 150.8 | 127.2 |
| PF24 Group O | Average | 762 | 768 | 775 |
| | SD | 150.5 | 183.1 | 196.7 |
| PF24 Group A | Average | 693 | 682 | 695 |
| | SD | 77.0 | 97.3 | 64.5 |
| PF24 All groups | Average | 728 | 725 | 735 |
| | SD | 113.5 | 139.5 | 138.1 |
| Aph FFP Group O | Average | 923 | 914 | 963 |
| | SD | 195.3 | 281.2 | 239.1 |
| Aph FFP Group A and B | Average | 954 | 1041 | 1052 |
| | SD | 17.2 | 93.4 | 100.7 |
| Aph FFP All groups | Average | 942 | 978 | 1008 |
| | SD | 99.9 | 186.1 | 158.3 |

TABLE 5

Total Factor VIII content (IU) after post-thaw storage.

| Plasma Unit | | t = 0 | t = 24 hr | t = 120 hr |
|---|---|---|---|---|
| WBD FFP Group O | Average | 178 | 158 | 138 |
| | SD | 50.7 | 46.8 | 5.1 |
| WBD FFP Group A | Average | 226 | 195 | 204 |
| | SD | 30.7 | 34.9 | 45.5 |
| WBD FFP All groups | Average | 202 | 176 | 171 |
| | SD | 45.7 | 42.2 | 46.2 |
| PF24 Group O | Average | 197 | 175 | 168 |
| | SD | 14.7 | 12.6 | 6.5 |
| PF24 Group A | Average | 197 | 211 | 243 |
| | SD | 14.7 | 14.1 | 32.7 |
| PF24 All groups | Average | 197 | 193 | 206 |
| | SD | 13.2 | 23.3 | 45.9 |
| Aph FFP Group O | Average | 184 | 72 | 67 |
| | SD | 52.4 | 16.8 | 18.8 |
| Aph FFP Group A and B | Average | 269 | 110 | 100 |
| | SD | 65.9 | 48.8 | 29.0 |
| Aph FFP All groups | Average | 235 | 91 | 83 |
| | SD | 70.8 | 37.0 | 27.6 |

Factor V, Factor VII, Factor VIII, Factor IX, Factor X, Factor XI and Fibrinogen content were determined for each of the six cryo-poor plasma supernatants obtained from the apheresis derived FFP, with the following average total content for the six samples: Factor V (464.4 IU; SD 38.1), Factor VII (465.4 IU; SD 55.4), Factor VIII (91.9 IU; SD 32.8), Factor IX (464.7 IU; SD 54.6), Factor X (494.8 IU; SD 10.7), Factor XI (507.8 IU; SD 67.5), and Fibrinogen (975.7 mg; SD 107.6).

For additional CPP preparations, multiple whole blood derived plasma collections were pooled and split into 625 mL components, and subjected to photochemical pathogen inactivation using INTERCEPT Blood System for Plasma. In one study comparing two commercially available transfer bags, the three PI plasma units (3 containers, see e.g., 112, 114, and 116 in FIG. 1B) generated from each INTERCEPT processing set were combined by transferring into a sterile-connected, single 750 mL or 800 mL transfer bags (see e.g., 122 in FIG. 1B) and frozen at −30° C. for use in the preparation of cryoprecipitate.

For preparing cryoprecipitate and CPP, the bags containing frozen pathogen-inactivated plasma were thawed in a 4° C. water bath for approximately 5 hr. The thawed plasma was centrifuged to sediment the cryoprecipitate, and the cryo-poor plasma supernatants were removed from the cryoprecipitate and transferred back into two of the three previous containers (see e.g., bags 112 and 114 in FIG. 1B), leaving approximately 100 mL of plasma (i.e., the cryo-poor plasma) to resuspend the cryoprecipitate, which was then transferred back into the third of the three previous containers (see e.g., bag 116 in FIG. 1B), and the cryoprecipitate and CPP units were frozen for storage.

Subsequent analysis of fibrinogen and Factor VIII levels in the cryo-poor plasma indicated high levels of fibrinogen, but no significant different between materials produced using either of the two transfer bags.

Similarly, additional CPP preparations were prepared from multiple units of whole blood derived plasma that were pooled by combining into a sterile connected 600 mL transfer bag, to obtain pooled plasmas with a volume of 585-650 mL. The pooled plasma was subjected to photochemical pathogen inactivation using INTERCEPT Blood System for Plasma per manufacturer's instructions and as described above. The three resulting PI plasma units (3 containers, see e.g., 112, 114, and 116 in FIG. 1B) generated from each INTERCEPT processing set were combined by transferring into a sterile-connected, single 600 mL transfer bag (see e.g., 122 in FIG. 1B), frozen in a blast freezer and transferred to a storage freezer at ≤−25° C. for use in the preparation of cryoprecipitate.

For preparing cryoprecipitate and CPP, the bags containing frozen pathogen-inactivated plasma were thawed in a 2-6° C. refrigerator for 20-24 hr, and centrifuged to sediment the cryoprecipitate. The cryo-poor plasma supernatants (~550 mL) were removed from the cryoprecipitate and transferred back into two of the three previous containers (see e.g., bags 112 and 114 in FIG. 1B), leaving approximately 50 mL of plasma (i.e., the cryo-poor plasma) to resuspend the cryoprecipitate, which was then transferred back into the third of the three previous containers (see e.g., bag 116 in FIG. 1B). Approximately 50 mL of CPP was transferred back into the 600 mL transfer bag to wash and collect residual cryoprecipitate and then transferred into and combined with the initial cryoprecipitate. This process yielded one container of cryoprecipitate (~100 mL) and two containers of cryo-poor plasma (~250 mL each). The CPP units and cryoprecipitate were frozen for storage. Analysis of five cryo-poor plasma preparations found a fibrinogen content of 288±37 mg and a Factor VIII content of 42±14 IU.

Example 5: PI Cryoprecipitate from Two Cryo Preparations

Pathogen inactivated cryoprecipitate compositions of the present disclosure may be combined to yield a cryoprecipitate composition with higher levels of desired factors, such as for example fibrinogen and Factor VIII. More specifically, a first cryoprecipitate is prepared from a large volume input of approximately 600 mL of FFP (e.g., 2-3 units, pooled) that is subjected to pathogen inactivation (e.g., INTERCEPT Blood System), as described in Example 2 above and illustrated in FIG. 1B. Following sedimentation of the cryoprecipitate, the cryo-poor supernatant is transferred back into the three containers for storage, leaving sufficient plasma for resuspension of the cryoprecipitate in approximately 35 mL. In addition, a second cryoprecipitate is prepared from a large volume input of approximately 600 mL of FFP (e.g., 2-3 units, pooled) of the same ABO type as the first cryoprecipitate and subjected to pathogen inactivation treatment in a similar manner. The container with the second cryoprecipitate is separated from the three cryo-poor plasma bags using a tube sealer, prior to combining with the first cryoprecipitate (FIG. 1C). The second cryoprecipitate (labeled Cryo "freeze" #2) is connected using a sterile connecting device to the container with the first cryoprecipitate, which has also been separated from its corresponding three cryo-poor plasma bags, and the two cryoprecipitate preparations combined by transfer prior to re-freezing or storage at room temperature for use.

Example 6: Pathogen-Inactivated Cryo-Poor Plasma for Guillain-Barré Syndrome

Pathogen-inactivated plasma compositions of the present disclosure may be used for treatment of Guillain-Barré syndrome. More specifically, for example, to evaluate the use of pathogen-inactivated cryo-poor plasma of the present disclosure in therapeutic plasma exchange for treatment of Guillain-Barré syndrome, a randomized, double-blind clinical study is performed, comparing pathogen-inactivated cryo-poor plasma and intravenous immunoglobulin. Study volunteers diagnosed are enrolled within two weeks of the start of symptoms at 100 subjects per group. For the pathogen-inactivated cryo-poor plasma treatment group, subjects receive multiple plasma exchanges (e.g., five) over a two week period, each as a 50 mL/kg exchange. For the IVIG treatment group, subjects receive five daily infusions of IVIG (e.g., GAMMAGARD, Baxter) at 0.4 gm/kg body weight/day.

Subjects are monitored over a period of 12 months for clinical adverse events and the following primary measure of efficacy: Proportion of patients with more than 1 grade improvement in Hughes Functional Grade (FG) at 28 days. Additional secondary measures of efficacy as measured at 28 days and later points (e.g., 6 months) include days required for 1 grade improvement of FG, days required for 2 grade improvement of FG, changes in activity of daily living (ADL), and one or more of hand dynamometer, Visual Analog Pain Scale, McGill Pain Questionnaire-Short Form, Neuromuscular Functional Assessment Index, Jebsen-Taylor Hand Function Test, Minnesota Rate of Manipulation and Manual Dexterity Tests, Walk Test and Center for Epidemiological Studies Depression Scale (CES-D).

Example 7: Pathogen-Inactivated Plasma for CIDP

Pathogen-inactivated plasma compositions of the present disclosure may be used for treatment of chronic inflammatory demyelinating polyneuropathy (CIDP). More specifically, for example, pathogen-inactivated cryo-poor plasma compositions of the present disclosure are used in therapeutic plasma exchange for the treatment of CIDP. Briefly, CIDP is a peripheral nerve disease of presumed autoimmune etiology that may include both humoral and cell-mediated immune responses. CIDP patients receive ten plasma exchange treatments over five weeks with 40-50 mL/kg plasma exchanged. Therapeutic response is measured by improvement or stabilization in neurological symptoms. Clinical outcomes are assessed during and after the treatment period using one or more of the Inflammatory Neuropathy Cause and Treatment (INCAT) score, maximum grip strength, the Medical Research Council (MRC) sum score, the Rasch-built Overall Disability Scale (R-ODS), and/or electrophysiological evaluations (see e.g., Dyck, et al., 1994, Ann. Neurol. 3:838-845).

INCAT Score. The INCAT score and changes in the score from baseline are determined. The INCAT disability score ranges from 0 to 10 and is the sum of arm and leg disability each rated between 0 and 5 (where arm=0 indicates 'no upper limb problems' and arm=5 indicates 'inability to use either arm for any purposeful movement', and leg=0 indicates 'walking not affected', and leg=5 indicates 'restricted to wheelchair, unable to stand and walk a few steps with help'). Thus, a higher INCAT disability score indicates greater disability. Negative values for change in INCAT score indicate improvement, with a more negative value indicating greater improvement compared with the value at baseline. Improvement is defined as an INCAT score decrease by at least 1 point.

Maximum Grip Strength. The mean maximum grip strength of the dominant hand and changes from baseline are determined. Positive values for change in maximum grip strength indicate improvement. Improvement is defined as improvement by at least 8 kPa.

Medical Research Council Sum Scale (MRC). The MRC sum score and changes from baseline are determined. The 80-point MRC sum score is the sum of scores for eight bilateral (left and right side) muscle groups, each rated between 0 (no visible contraction) to 5 (normal movement). A higher MRC sum score indicates greater muscle contraction/limb movement. Positive values for change in MRC sum score indicate improvement, with a more positive value indicating greater muscle contraction/limb movement compared with the value at baseline.

Example 8: Pathogen-Inactivated Plasma for Renal Transplantation

Pathogen-inactivated plasma compositions of the present disclosure may be used in conjunction with solid organ transplantation. For example, pathogen-inactivated cryo-poor plasma compositions are used for a therapeutic plasma exchange regimen in conjunction with ABO-incompatible kidney transplantation to reduce circulating antibody (e.g., IgG) that may contribute to transplant rejection. More specifically, in one example, transplant patients receiving an ABO-incompatible kidney from a living donor are subjected to a preconditioning regimen of multiple therapeutic plasma exchange (TPE) treatments before transplant to reduce ABO antibody (e.g., anti-A, anti-B) titers to a desired level, such as for example to pre-transplant titers of less than 16. TPE treatments are performed daily prior to transplant using accepted plasma exchange methods known in the art and as described herein, with the number of TPE treatments based on the initial ABO antibody titers. For example, in one embodiment, two TPE treatments are used for an initial antibody titer of 16, three TPE treatments for an initial titer of 32, four TPE treatment for an initial titer of 64, five TPE treatments for an initial titer of 128, seven TPE treatments for an initial titer of 256, nine TPE treatments for an initial titer of 512, eleven TPE treatments for an initial titer of 1024, and fifteen or more TPE treatment for an initial titer of >1024. The pathogen-inactivated plasma compositions used for TPE treatment may be obtained from plasma donors seropositive for cytomegalovirus (CMV).

On the day of transplant, high risk patients may be subjected to splenectomy and/or anti-CD20 therapy. Following the kidney transplant procedure, the patients are subjected to one or more additional daily TPE treatments (e.g., two, three) with the pathogen-inactivated plasma to reduce the risk of antibody rebound.

Example 9: Pathogen-Inactivated Plasma for Burn Resuscitation

Pathogen-inactivated plasma compositions of the present disclosure may be used for fluid resuscitation in a subject suffering from burns (e.g., burn shock resuscitation). More specifically, in one example, a subject suffering from major burns representing approximately 25% of total body surface area (TBSA) is infused with ABO-matched pathogen-inactivated cryo-poor plasma prepared as described above. Infusion of the CPP is initiated based on an amount calculated as 3 mL of CPP per kg body weight per % TBSA, with half of the amount infused within the first 8 hours. Resuscitation with the cryo-poor plasma is continued as guided by titration to maintain a urine output of about 1.0 ml/kg/hour.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Wherever an open-ended term is used to describe a feature or element, it is specifically contemplated that a closed-ended term can be used in place of the open-ended term without departing from the spirit and scope of the disclosure. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the description and does not pose a limitation on the scope of the description unless otherwise claimed. No language in the specification should be construed as indicating any non-claimed element as essential to the practice of the compositions, methods, and kits disclosed herein.

Preferred embodiments are described herein. Variations of those preferred embodiments may become apparent to those working in the art upon reading the foregoing description. It is expected that skilled artisans will be able to employ such variations as appropriate, and the practice of the compositions, methods, and kits described herein otherwise than as specifically described herein. Accordingly, the compositions, methods, and kits described herein include all modifications and equivalents of the subject matter recited in the claims appended hereto as permitted by applicable law. Moreover, any combination of the above-described elements in all possible variations thereof is encompassed by the description unless otherwise indicated herein or otherwise clearly contradicted by context.

LIST OF EMBODIMENTS

Embodiment 1

A method of treating a disease or condition indicated for treatment by plasma exchange in a subject in need thereof, comprising administering to the subject a therapeutically effective amount of pathogen-inactivated plasma composition by plasma exchange.

Embodiment 2

The method of embodiment 1, wherein the disease or condition is indicated for treatment with albumin by plasma exchange.

Embodiment 3

The method of embodiment 1 or embodiment 2, wherein the disease or condition is Guillain-Barré syndrome, chronic inflammatory demyelinating polyneuropathy, myasthenia gravis, a paraproteinemic polyneuropathy, Goodpasture's syndrome, or cryoglobulinemia.

Embodiment 4

The method of embodiment 1 or embodiment 2, wherein the disease or condition is other than thrombocytopenic purpura (TTP) or hemolytic-uremic syndrome (HUS).

Embodiment 5

The method of embodiment 1 or embodiment 2, wherein the disease or condition is burn shock resuscitation.

Embodiment 6

The method of any one of embodiments 1-5, wherein the pathogen-inactivated plasma composition comprises pathogen-inactivated frozen plasma.

Embodiment 7

The method of embodiment 6, wherein the pathogen-inactivated plasma composition comprises pathogen-inactivated fresh frozen plasma.

Embodiment 8

The method of any one of embodiments 1-5, wherein the pathogen-inactivated plasma composition comprises pathogen-inactivated cryo-poor plasma.

Embodiment 9

The method of embodiment 8, wherein the disease or condition is thrombocytopenic purpura (TTP) or hemolytic-uremic syndrome (HUS).

Embodiment 10

A method of treating a disease or condition indicated for treatment by infusion with intravenous immunoglobulin in a subject in need thereof, comprising administering to the subject a therapeutically effective amount of pathogen-inactivated plasma composition by plasma exchange.

Embodiment 11

The method of embodiment 10, wherein the disease or condition is Guillain-Barré syndrome, myasthenia gravis, polymyositis, dermatomyositis, or chronic inflammatory demyelinating polyneuropathy.

Embodiment 12

The method of embodiment 10, wherein the disease or condition is other than thrombocytopenic purpura (TTP) or hemolytic-uremic syndrome (HUS).

Embodiment 13

The method of any one of embodiments 10-12, wherein the pathogen-inactivated plasma composition comprises pathogen-inactivated frozen plasma.

Embodiment 14

The method of embodiment 13, wherein the pathogen-inactivated plasma composition comprises pathogen-inactivated fresh frozen plasma.

Embodiment 15

The method of any one of embodiments 10-12, wherein the pathogen-inactivated plasma composition comprises pathogen-inactivated cryo-poor plasma.

Embodiment 16

The method of embodiment 15, wherein the disease or condition is thrombocytopenic purpura (TTP) or hemolytic-uremic syndrome (HUS).

Embodiment 17

A method of treating a disease or condition selected from the group consisting of Guillain-Barré syndrome, myasthenia gravis, polymyositis, dermatomyositis and chronic inflammatory demyelinating polyneuropathy in a subject, comprising administering to a subject in need thereof a therapeutically effective amount of pathogen-inactivated plasma composition by plasma exchange.

Embodiment 18

The method of embodiment 17, wherein the pathogen-inactivated plasma composition comprises pathogen-inactivated frozen plasma.

Embodiment 19

The method of embodiment 18, wherein the pathogen-inactivated plasma composition comprises pathogen-inactivated fresh frozen plasma.

Embodiment 20

The method of embodiment 17, wherein the pathogen-inactivated plasma composition comprises pathogen-inactivated cryo-poor plasma.

Embodiment 21

The method of any one of embodiments 1-20, wherein the pathogen-inactivated plasma composition is administered within 1 day, 2 days, 3 days, 4 days, 5 days, 6 days, or 7 days after thawing.

Embodiment 22

The method of any one of embodiments 1-20, wherein the pathogen-inactivated plasma composition is a lyophilized or freeze-dried plasma composition.

Embodiment 23

The method of embodiment 22, wherein the pathogen-inactivated plasma composition is administered within 1 day, 2 days, 3 days, 4 days, 5 days, 6 days, or 7 days after reconstitution.

Embodiment 24

A method of treating thrombocytopenic purpura (TTP) or hemolytic-uremic syndrome (HUS) in a subject, comprising administering to a subject in need thereof a therapeutically effective amount of a pathogen-inactivated plasma composition by plasma exchange, wherein the pathogen-inactivated plasma composition comprises pathogen-inactivated cryo-poor plasma.

Embodiment 25

A method of treating a solid organ transplant recipient to prevent an immune-mediated solid organ transplant rejection, comprising administering to the transplant recipient a therapeutically effective amount of a pathogen-inactivated plasma composition by plasma exchange, wherein the plasma exchange is prior to the transplant procedure.

Embodiment 26

The method of embodiment 25, wherein the immune-mediated transplant rejection is an antibody-mediated transplant rejection.

Embodiment 27

The method of embodiment 26, wherein the antibody-mediated transplant rejection is an IgG-mediated transplant rejection.

Embodiment 28

The method of any one of embodiments 25-26, wherein the solid organ transplant is an ABO-incompatible solid organ transplant.

Embodiment 29

The method of any one of embodiments 25-26, wherein the solid organ transplant is an HLA-incompatible solid organ transplant.

Embodiment 30

The method of any one of embodiments 25-29, wherein the solid organ transplant is a kidney transplant.

Embodiment 31

The method of embodiment 30, wherein the kidney is obtained from a living donor.

Embodiment 32

The method of any one of embodiments 25-31, wherein the pathogen-inactivated plasma composition comprises pathogen-inactivated frozen plasma.

Embodiment 33

The method of embodiment 32, wherein the pathogen-inactivated plasma composition comprises pathogen-inactivated fresh frozen plasma.

Embodiment 34

The method of any one of embodiments 25-31, wherein the pathogen-inactivated plasma composition comprises pathogen-inactivated cryo-poor plasma.

Embodiment 35

The method of any one of embodiments 25-34, wherein the pathogen-inactivated plasma composition is administered within 1 day, 2 days, 3 days, 4 days, 5 days, 6 days, or 7 days after thawing.

Embodiment 36

The method of any one of embodiments 25-31, wherein the pathogen-inactivated plasma composition is a lyophilized or freeze-dried plasma composition.

Embodiment 37

The method of embodiment 36, wherein the pathogen-inactivated plasma composition is administered within 1 day, 2 days, 3 days, 4 days, 5 days, 6 days, or 7 days after reconstitution.

Embodiment 38

The method of any one of embodiments 1-37, wherein the plasma exchange is achieved with a volume of the plasma composition similar to the subject's plasma volume.

Embodiment 39

The method of any one of embodiments 1-37, wherein the plasma exchange is achieved with a volume of the plasma composition between about 1 times and about 1.5 times the subject's plasma volume.

Embodiment 40

The method of any one of embodiments 1-37, wherein the plasma exchange is achieved with a volume of the plasma composition comprising about 40 mL/kg patient body weight.

Embodiment 41

The method of any one of embodiments 1-37, wherein the plasma exchange is achieved with a volume of the plasma composition comprising about 60 mL/kg patient body weight.

Embodiment 42

The method of any one of embodiments 1-41, wherein the plasma exchange is performed at least two times.

Embodiment 43

The method of embodiment 42, wherein the plasma exchange is performed 2-5 times.

Embodiment 44

The method of embodiment 42 or embodiment 43, wherein the plasma exchange is performed 2-5 times within a period of two weeks.

Embodiment 45

The method of embodiment 42 or embodiment 43, wherein the plasma exchange is performed 2-5 times within a period of one week.

Embodiment 46

The method of any one of embodiments 25-45, wherein the plasma exchange is performed at least two times prior to the transplant procedure.

Embodiment 47

The method of embodiment 46, wherein the plasma exchange is performed 2-15 times prior to the transplant procedure.

Embodiment 48

The method of any one of embodiments 25-47, further comprising administering to the transplant recipient a therapeutically effective amount of pathogen-inactivated plasma composition by plasma exchange after the transplant procedure.

Embodiment 49

The method of embodiment 48, wherein the plasma exchange is performed at least two times after the transplant procedure.

Embodiment 50

A method of fluid resuscitation in a subject suffering from burns, comprising administering to a subject in need thereof a therapeutically effective amount of a pathogen-inactivated plasma composition.

Embodiment 51

The method of embodiment 50, wherein the subject is suffering from major burns comprising at least 20% of total body surface area.

Embodiment 52

The method of embodiment 50 or embodiment 51, wherein the method of fluid resuscitation is a method of burn shock resuscitation.

Embodiment 53

The method of any one of embodiments 50-52, wherein endothelial permeability, endothelial dysfunction and/or vascular hyperpermeability is reduced by administration of the pathogen-inactivated plasma composition.

Embodiment 54

The method of any one of embodiments 50-53, wherein administration of the pathogen-inactivated plasma composition results in decreased subject mortality.

Embodiment 55

The method of any one of embodiments 50-54, wherein the pathogen-inactivated plasma composition comprises pathogen-inactivated frozen plasma.

Embodiment 56

The method of embodiment 55, wherein the pathogen-inactivated plasma composition comprises pathogen-inactivated fresh frozen plasma.

Embodiment 57

The method of any one of embodiments 50-54, wherein the pathogen-inactivated plasma composition comprises pathogen-inactivated cryo-poor plasma.

Embodiment 58

The method of any one of embodiments 50-57, wherein the pathogen-inactivated plasma composition is administered within 1 day, 2 days, 3 days, 4 days, 5 days, 6 days, or 7 days after thawing.

Embodiment 59

The method of any one of embodiments 50-54, wherein the pathogen-inactivated plasma composition is a lyophilized or freeze-dried plasma composition.

Embodiment 60

The method of embodiment 59, wherein the pathogen-inactivated plasma composition is administered within 1 day, 2 days, 3 days, 4 days, 5 days, 6 days, or 7 days after reconstitution.

Embodiment 61

The method of any one of embodiments 50-60, wherein about 1 mL to about 5 mL per kg body weight per % total burn surface area (TBSA) of the pathogen-inactivated plasma composition is administered to the subject.

Embodiment 62

The method of any one of embodiments 50-60, wherein a volume of the pathogen-inactivated plasma composition sufficient to achieve an increase in blood pressure to at least about 50 mmHg is administered to the subject.

Embodiment 63

The method of embodiment 62, wherein a volume of the pathogen-inactivated plasma composition sufficient to achieve an increase in blood pressure to at least about 100 mmHg is administered to the subject.

Embodiment 64

The method of any one of embodiments 50-63, wherein the pathogen-inactivated plasma composition is administered to the subject within about 24 hours, within about 20 hours, within about 16 hours, within about 12 hours, within about 10 hours, within about 8 hours, within about 6 hours, within about 5 hours, within about 4 hours, within about 3 hours, within about 2 hours or within about 1 hours after the onset of burns or medical diagnosis thereof.

Embodiment 65

The method of any one of embodiments 50-64, wherein pathogen-inactivated plasma composition is administered to the subject over a time period of about 24 hours.

Embodiment 66

The method of embodiment 65, wherein pathogen-inactivated plasma composition is administered to the subject in multiple infusions over a time period of about 24 hours Embodiment 67. A method of treating a subject suffering from burns or a trauma, the method comprising: administering to a subject in need thereof a therapeutically effective amount of a pathogen-inactivated plasma composition.

Embodiment 68

The method of embodiment 67, wherein the subject is suffering from burns.

Embodiment 69

The method of embodiment 67, wherein the subject is suffering from blunt trauma.

Embodiment 70

The method of embodiment 67, wherein the subject is suffering from penetrating trauma.

Embodiment 71

The method of any one of embodiments 67-70, wherein the subject is suffering from hemorrhage.

Embodiment 72

The method of embodiment 71, wherein the subject is suffering from internal hemorrhage.

Embodiment 73

The method of any one of embodiments 67-72, wherein the method is a method of fluid resuscitation.

Embodiment 74

The method of any one of embodiments 67-73, wherein the method reduces hemorrhage in the subject.

Embodiment 75

The method of any one of embodiments 67-74, wherein the method reduces hemorrhagic shock in the subject.

Embodiment 76

The method of any one of embodiments 67-74, wherein endothelial permeability is reduced in the subject.

Embodiment 77

The method of any one of embodiments 67-74, wherein the method reduces or prevents trauma-induced endotheliopathy in the subject.

Embodiment 78

The method of any one of embodiments 67-74, wherein the method reduces or prevents traumatic coagulopathy in the subject.

Embodiment 79

The method of any one or embodiments 67-78, wherein the infusion or treatment results in decreased subject mortality.

Embodiment 80

A method of resuscitation from hemorrhagic shock in a subject suffering from burns or a trauma, comprising administering to the subject a therapeutically effective amount of a pathogen-inactivated plasma composition.

Embodiment 81

The method of embodiment 80, wherein the subject is suffering from burns.

Embodiment 82

The method of embodiment 80, wherein the subject is suffering from blunt trauma.

Embodiment 83

The method of embodiment 80, wherein the subject is suffering from penetrating trauma.

Embodiment 84

The method of any one of embodiments 80-83, wherein the subject is suffering from internal hemorrhage.

Embodiment 85

The method of any one of embodiments 80-84, wherein the method reduces hemorrhage in the subject.

Embodiment 86

The method of any one of embodiments 80-85, wherein endothelial permeability is reduced in the subject.

Embodiment 87

The method of any one of embodiments 80-85, wherein the method reduces or prevents trauma-induced endotheliopathy in the subject.

Embodiment 88

The method of any one of embodiments 80-85, wherein the method reduces or prevents traumatic coagulopathy in the subject.

Embodiment 89

The method of any one or embodiments 80-88, wherein the treatment results in decreased subject mortality.

Embodiment 90

The method of any one of embodiments 67-89, wherein the pathogen-inactivated plasma composition comprises pathogen-inactivated frozen plasma.

Embodiment 91

The method of embodiment 90, wherein the pathogen-inactivated plasma composition comprises pathogen-inactivated fresh frozen plasma.

Embodiment 92

The method of any one of embodiments 67-89, wherein the pathogen-inactivated plasma composition comprises pathogen-inactivated cryo-poor plasma.

Embodiment 93

The method of any one of embodiments 67-92, wherein the pathogen-inactivated plasma composition is administered within 1 day, 2 days, 3 days, 4 days, 5 days, 6 days, or 7 days after thawing.

Embodiment 94

The method of any one of embodiments 67-89, wherein the pathogen-inactivated plasma composition is a lyophilized or freeze-dried plasma composition.

Embodiment 95

The method of embodiment 94, wherein the pathogen-inactivated plasma composition is administered within 1 day, 2 days, 3 days, 4 days, 5 days, 6 days, or 7 days after reconstitution.

Embodiment 96

The method of any one of embodiments 67-95, wherein the pathogen-inactivated plasma composition is first administered less than 24 hours after the onset of trauma.

Embodiment 97

The method of any one of embodiments 67-96, wherein administration of the pathogen-inactivated plasma composition is followed by administration of at least one additional intravenous fluid.

Embodiment 98

A method for preparing pathogen-inactivated cryo-poor plasma, the method comprising:

a) photochemically inactivating one or more units of plasma in the presence of a psoralen, wherein the photochemical inactivation is performed under sterile conditions in a first container containing the one or more units of plasma;

b) transferring under sterile conditions the one or more units of plasma from the first container to a compound absorption device (CAD) coupled to the first container;

c) transferring under sterile conditions the one or more units of plasma from the CAD to two or more second containers coupled to the CAD to provide pathogen-inactivated plasma;

d) transferring under sterile conditions the pathogen-inactivated plasma from the two or more second containers to a third container coupled to the two or more second containers;

e) freezing the pathogen-inactivated plasma followed by thawing of the pathogen-inactivated plasma under conditions that provide for the formation of a cryoprecipitate and pathogen-inactivated cryo-poor plasma;

f) transferring the pathogen-inactivated cryo-poor plasma to a at least a first of the two or more second containers; and g) transferring the cryoprecipitate to a second of the two or more second containers.

Embodiment 99

The method of embodiment 98, wherein at least a portion of the pathogen-inactivated cryo-poor plasma is transferred to each of at least two second containers in step f), and wherein the cryoprecipitate is transferred to a third second container in step g).

Embodiment 100

The method of embodiment 98 or embodiment 99, wherein, prior to step g), the cryoprecipitate is resuspended in about 80 mL to about 120 mL of pathogen-inactivated cryo-poor plasma.

Embodiment 101

The method of embodiment 100, wherein, prior to step g), the cryoprecipitate is resuspended in about 100 mL of pathogen-inactivated cryo-poor plasma.

Embodiment 102

A method for infusing pathogen-inactivated cryo-poor plasma into a subject, comprising infusing into a subject in need thereof a therapeutically effective amount of a pathogen-inactivated cryo-poor plasma prepared by the method of any one of embodiments 98-101.

Embodiment 103

The method of embodiment 102, wherein the subject is suffering from one or more of burns, blunt trauma, penetrating trauma, and hemorrhage.

Embodiment 104

The method of embodiment 102 or embodiment 103, wherein the infusion results in fluid resuscitation of the subject.

Embodiment 105

The method of embodiment 102, wherein infusing the pathogen-inactivated cryo-poor plasma into a subject is by therapeutic plasma exchange.

Embodiment 106

The method of embodiment 105, wherein the subject in need thereof is a subject suffering from thrombocytopenic purpura (TTP) or hemolytic-uremic syndrome (HUS).

Embodiment 107

The method of any one of embodiments 102-106, further comprising, prior to the infusion:

1) freezing the pathogen-inactivated cryo-poor plasma; and 2) thawing the pathogen-inactivated cryo-poor plasma.

Embodiment 108

The method of embodiment 107, wherein the pathogen-inactivated cryo-poor plasma is infused into the subject within 1 day, 2 days, 3 days, 4 days, 5 days, 6 days, or 7 days after thawing.

What is claimed is:

1. A method for preparing pathogen-inactivated cryo-poor plasma, the method comprising:

a) photochemically inactivating one or more units of plasma in the presence of a psoralen, wherein the photochemical inactivation is performed under sterile conditions in a first container containing the one or more units of plasma;

b) transferring under sterile conditions the one or more units of plasma from the first container to a compound absorption device (CAD) coupled to the first container;

c) transferring under sterile conditions the one or more units of plasma from the CAD to two or more second containers coupled to the CAD to provide pathogen-inactivated plasma;

d) transferring under sterile conditions the pathogen-inactivated plasma from the two or more second containers to a third container coupled to the two or more second containers;

e) freezing the pathogen-inactivated plasma followed by thawing of the pathogen-inactivated plasma under conditions that provide for the formation of a cryoprecipitate and pathogen-inactivated cryo-poor plasma;

f) transferring the pathogen-inactivated cryo-poor plasma to at least a first of the two or more second containers; and g) transferring the cryoprecipitate to a second of the two or more second containers.

2. The method of claim 1, wherein at least a portion of the pathogen-inactivated cryo-poor plasma is transferred to each of at least two second containers in step f), and wherein the cryoprecipitate is transferred to a third second container in step g).

3. The method of claim 1, wherein step c) comprises transferring the one or more units of plasma from the CAD to three second containers coupled to the CAD to provide pathogen-inactivated plasma.

4. The method of claim 1, wherein the third container is coupled to the two or more second containers by sterile docking to tubing between the CAD and the two or more second containers.

5. The method of claim 1, wherein the one or more units of plasma comprise one or more plasma units from a whole blood donation.

6. The method of claim 1, wherein the one or more units of plasma comprise one or more plasma units from apheresis collected plasma.

7. The method of claim 1, wherein the one or more units of plasma comprise plasma pooled from multiple units.

8. The method of claim 1, wherein the psoralen is amotosalen.

9. The method of claim 1, wherein the pathogen-inactivated cryo-poor plasma is prepared from at least about 550 mL and less than about 650 mL of pathogen-inactivated plasma.

10. The method of claim 1, wherein, prior to step g), the cryoprecipitate is resuspended in about 80 mL to about 120 mL of pathogen-inactivated cryo-poor plasma.

11. A method for infusing pathogen-inactivated cryo-poor plasma into a subject, comprising infusing into a subject in need thereof a therapeutically effective amount of a pathogen-inactivated cryo-poor plasma prepared by the method of claim 1.

12. The method of claim 11, wherein the subject is suffering from one or more of burns, blunt trauma, penetrating trauma, and hemorrhage.

13. The method of claim 11, wherein the infusion results in fluid resuscitation of the subject.

14. The method of claim 11, wherein the pathogen-inactivated cryo-poor plasma is infused into the subject by therapeutic plasma exchange.

15. The method of claim 11, further comprising, prior to the infusion:

1) freezing the pathogen-inactivated cryo-poor plasma; and 2) thawing the pathogen-inactivated cryo-poor plasma.

16. The method of claim 15, wherein the pathogen-inactivated cryo-poor plasma is infused into the subject within 5 days after thawing.

* * * * *